US007582288B2

(12) United States Patent
Gillies et al.

(10) Patent No.: US 7,582,288 B2
(45) Date of Patent: Sep. 1, 2009

(54) METHODS OF TARGETING MULTIPLE CYTOKINES

(75) Inventors: Stephen D. Gillies, Carlisle, MA (US); Kin-Ming Lo, Lexington, MA (US)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 11/603,278

(22) Filed: Nov. 20, 2006

(65) Prior Publication Data

US 2007/0258944 A1 Nov. 8, 2007

Related U.S. Application Data

(63) Continuation of application No. 10/603,064, filed on Jun. 24, 2003, now Pat. No. 7,141,651, which is a continuation of application No. 09/634,368, filed on Aug. 9, 2000, now Pat. No. 6,617,135.

(60) Provisional application No. 60/147,924, filed on Aug. 9, 1999.

(51) Int. Cl.
*A61K 38/19* (2006.01)
*A61K 38/20* (2006.01)

(52) U.S. Cl. .................. 424/85.1; 424/85.2; 424/178.1

(58) Field of Classification Search ....................... None
See application file for complete search history.

(56) References Cited

U.S. PATENT DOCUMENTS 4,196,265 A 4/1980 Koprowski et al. ............. 435/2
4,469,797 A 9/1984 Albarella .................... 436/536
4,676,980 A 6/1987 Segal et al. ................... 424/85
4,703,008 A 10/1987 Lin
4,732,683 A 3/1988 Georgiades et al.
4,737,462 A 4/1988 Mark et al.
4,816,567 A 3/1989 Cabilly et al. ............... 530/387
4,946,778 A 8/1990 Ladner et al. .............. 435/69.6
5,019,368 A 5/1991 Epstein et al.
5,073,627 A 12/1991 Curtis et al. ................ 530/351
5,082,658 A 1/1992 Palladino
5,091,513 A 2/1992 Huston et al.
5,114,711 A 5/1992 Bell et al. .................. 424/85.1
5,116,964 A 5/1992 Capon et al. .................. 536/27
5,199,942 A 4/1993 Gillis ............................ 604/4
5,225,538 A 7/1993 Capon et al. ............. 530/387.3
5,225,539 A 7/1993 Winter .................... 530/387.3
5,258,498 A 11/1993 Huston et al. ............... 530/350
5,314,995 A 5/1994 Fell, Jr. et al. .............. 530/351
5,349,053 A 9/1994 Landolfi ..................... 530/351
5,359,035 A 10/1994 Habermann
5,399,346 A 3/1995 Anderson et al.
5,428,130 A 6/1995 Capon et al.
5,441,868 A 8/1995 Lin
5,457,038 A 10/1995 Trinchieri et al.
5,514,582 A 5/1996 Capon et al. ............. 435/252.3
5,538,866 A 7/1996 Israeli et al.
5,541,087 A 7/1996 Lo et al. ..................... 435/697
5,543,297 A 8/1996 Cromlish et al. .............. 435/25
5,547,933 A 8/1996 Lin
5,552,524 A 9/1996 Basinski et al.
5,585,089 A 12/1996 Queen et al. ............. 424/133.1
5,601,819 A 2/1997 Wong et al.
5,609,846 A 3/1997 Goldenberg ............... 424/1.41
5,618,698 A 4/1997 Lin
5,624,821 A 4/1997 Winter et al.
5,639,725 A 6/1997 O'Reilly et al. ............... 514/12
5,645,835 A 7/1997 Fell, Jr. et al.
5,650,150 A 7/1997 Gillies ..................... 424/134.1
5,650,492 A 7/1997 Gately et al. ................ 530/351
5,667,776 A 9/1997 Zimmerman et al. ........ 424/238
5,679,543 A 10/1997 Lawlis
5,688,679 A 11/1997 Powell
5,691,309 A 11/1997 Basinski et al.
5,709,859 A 1/1998 Aruffo et al.
5,719,266 A 2/1998 DiMarchi et al.
5,723,125 A 3/1998 Chang et al. ............ 424/134.1
5,726,044 A 3/1998 Lo et al. .................... 435/69.7
5,728,552 A 3/1998 Fujisawa et al. ........... 435/69.5
5,733,876 A 3/1998 O'Reilly et al. ............... 514/12
5,756,349 A 5/1998 Lin
5,756,461 A 5/1998 Stephens
5,759,551 A 6/1998 Ladd et al. ............... 424/198.1
5,770,195 A 6/1998 Hudziak et al. .......... 424/130.1
5,795,779 A 8/1998 McCormick (Continued)

FOREIGN PATENT DOCUMENTS

AU 21725/88 3/1989

(Continued)

OTHER PUBLICATIONS

U.S. Appl. No. 07/348,237, filed May 5, 1989, Rosenblum et al.
Harris et al., "Therapeutic Antibodies—the Coming of Age" *Tibtech*, 11:42-44 (Feb. 1993).
Hoogenboom et al., *Biochim. and Biophys. Acta*, 1096:345-354 (1991) (Abstract).
Gillies et al., "Antigen binding and biological activities of engineered mutant chimeric antibodies with human tumor specificities", *Hum. Antibod. Hybridomas*, 1 (No. 1):47-54 (1990).
Shin et al., "Expression and characterization of an antibody binding specificity joined to insulin-like growth factor 1: Potential applications for cellular targeting.", *Proc. Natl. Acad. Sci. USA*, 87:5322-5326 (1990).

(Continued)

*Primary Examiner*—Prema Mertz
(74) *Attorney, Agent, or Firm*—Goodwin Procter LLP

(57) ABSTRACT

The invention relates to protein complexes and fusion proteins including at least two different cytokine molecules. The protein complexes and fusion proteins may further include a targeting moiety such as a region of an immunoglobulin. Methods of using the protein complexes and fusion proteins are also disclosed.

6 Claims, 19 Drawing Sheets

U.S. PATENT DOCUMENTS 5,800,810 A 9/1998 Doyle et al. ............... 424/85.2
5,807,715 A 9/1998 Morrison et al.
5,827,516 A 10/1998 Urban et al. ............. 424/93.21
5,827,703 A 10/1998 Debs et al.
5,837,682 A 11/1998 Folkman et al. ............... 514/12
5,843,423 A 12/1998 Lyman et al. .............. 424/85.1
5,854,205 A 12/1998 O'Reilly et al. ................ 514/2
5,856,298 A 1/1999 Strickland
5,858,347 A 1/1999 Bauer et al. ................ 424/85.2
5,885,795 A 3/1999 O'Reilly et al. ............ 435/69.1
5,886,178 A 3/1999 Allen et al. ................. 544/238
5,888,772 A 3/1999 Okasinski et al.
5,891,680 A 4/1999 Lieschke et al.
5,908,626 A 6/1999 Chang et al. ............. 424/134.1
5,922,685 A 7/1999 Rakhmilevich et al.
5,955,422 A 9/1999 Lin
5,994,104 A 11/1999 Anderson et al.
5,994,126 A 11/1999 Steinman et al. ............ 435/325
6,080,409 A 6/2000 Laus et al. ............... 424/192.1
6,086,875 A 7/2000 Blumberg et al. ........ 424/134.1
6,100,387 A 8/2000 Herrmann et al.
6,169,070 B1 1/2001 Chen et al.
6,171,588 B1 1/2001 Carron et al.
6,231,536 B1 5/2001 Lentz
6,277,375 B1 8/2001 Ward
6,284,536 B1 9/2001 Morrison et al.
6,335,176 B1 1/2002 Inglese et al.
6,340,742 B1 1/2002 Burg et al.
6,348,192 B1 2/2002 Chan et al.
6,406,689 B1 6/2002 Falkenberg et al.
6,429,199 B1 8/2002 Krieg et al.
6,444,792 B1 9/2002 Gray et al.
6,475,717 B1 11/2002 Enssle et al.
6,485,726 B1 11/2002 Blumberg et al.
6,500,641 B1 12/2002 Chen et al.
6,506,405 B1 1/2003 Desai et al.
6,551,592 B2 4/2003 Lindhofer et al.
6,583,272 B1 6/2003 Bailon
6,586,398 B1 7/2003 Kinstler et al.
6,617,135 B1 9/2003 Gillies et al.
6,627,615 B1 9/2003 Debs et al.
6,646,113 B1 11/2003 Dreyfuss et al.
2001/0053539 A1 12/2001 Lauffer et al.
2002/0037558 A1 3/2002 Lo et al.
2002/0081664 A1 6/2002 Lo et al.
2002/0142374 A1 10/2002 Gallo et al.
2002/0146388 A1 10/2002 Gillies
2002/0147311 A1 10/2002 Gillies et al.
2002/0192222 A1 12/2002 Blumberg et al.
2002/0193570 A1 12/2002 Gillies et al.
2003/0003529 A1 1/2003 Bayer
2003/0012789 A1 1/2003 Blumberg et al.
2003/0044423 A1 3/2003 Gillies et al.
2003/0049227 A1 3/2003 Gillies et al.
2003/0105294 A1 6/2003 Gillies et al.
2003/0139365 A1 7/2003 Lo et al.
2003/0139575 A1 7/2003 Gillies
2003/0157054 A1 8/2003 Gillies et al.
2003/0166163 A1 9/2003 Gillies
2003/0166877 A1 9/2003 Gillies et al.
2004/0013640 A1 1/2004 Zardi et al.
2004/0033210 A1 2/2004 Gillies
2004/0043457 A1 3/2004 Schumacher et al.
2004/0053366 A1 3/2004 Lo et al.
2004/0072299 A1 4/2004 Gillies et al.
2004/0082039 A1 4/2004 Gillies et al.
2004/0180035 A1 9/2004 Gillies et al.
2004/0180386 A1 9/2004 Carr et al.
2004/0203100 A1 10/2004 Gillies et al.

FOREIGN PATENT DOCUMENTS

CN 93100115.3 7/1993
DE 37 12985 11/1988
DE 37 12985 A1 11/1988
EP 0 158 198 A1 10/1985
EP 211769 2/1987
EP 0 237 019 9/1987
EP 0 294703 A2 9/1987
EP 256714 2/1988
EP 0 294 703 A2 12/1988
EP 0 308 936 A2 3/1989
EP 0 314 317 A1 5/1989
EP 0 314317 A1 5/1989
EP 319012 6/1989
EP 350230 1/1990
EP 0 375 562 6/1990
EP 0 396 387 A2 11/1990
EP 0 439 095 A2 7/1991
EP 0 511 747 11/1992
EP 0 640 619 A1 3/1995
EP 0 318 554 B1 4/1995
EP 0 668 353 A1 8/1995
EP 0 428 596 B1 4/1996
EP 0 706 799 A3 4/1996
EP 0 790 309 A1 8/1997
EP 0 433 827 B1 3/1998
EP 0 326 120 B1 4/1998
EP 0 601 043 B1 11/1998
EP 1 088 888 A1 4/2001
GB 2292382 A 2/1996
JP 63-267278 11/1988
JP 63-267296 11/1988
JP 87-56676 11/1988
JP 87-56677 11/1988
WO WO86/01533 3/1986
WO WO88/00052 1/1988
WO WO 88/09344 12/1988
WO WO88/09344 12/1988
WO WO 89/02922 4/1989
WO WO89/02922 4/1989
WO WO 89/09620 10/1989
WO WO 90/03801 4/1990
WO WO 91/00360 1/1991
WO WO 91/04329 A1 4/1991
WO WO 91/08298 6/1991
WO WO 91/13166 9/1991
WO WO 91/14438 10/1991
WO WO 92/02240 2/1992
WO WO 92/08801 5/1992
WO WP 92/08495 5/1992
WO WO 92/10755 6/1992
WO WO 92/16562 10/1992
WO WO 93/03157 2/1993
WO WO93/10229 5/1993
WO WO 93/20185 10/1993
WO WO 94/24160 10/1994
WO WO 94/25055 11/1994
WO WO 94/25609 11/1994
WO WO 95/05468 2/1995
WO WO 95/21258 8/1995
WO WO95/28427 10/1995
WO WO 95/31483 11/1995
WO WO 96/04388 2/1996
WO WO 96/05309 2/1996
WO WO 96/08570 3/1996
WO WO 96/18412 6/1996
WO WO 96/31526 10/1996
WO WO 97/00319 1/1997
WO WO 97/33619 1/1997
WO WO 97/15666 5/1997

| | | |
|---|---|---|
| WO | WO 97/20062 | 6/1997 |
| WO | WO97/24137 | 7/1997 |
| WO | WO 97/24440 | 7/1997 |
| WO | WO 97/26335 | 7/1997 |
| WO | WO 97/30089 | 8/1997 |
| WO | WO 97/00317 | 9/1997 |
| WO | WO 97/33617 | 9/1997 |
| WO | WO 97/34631 | 9/1997 |
| WO | WO 97/43316 | 11/1997 |
| WO | WO 98/00127 | 1/1998 |
| WO | WO 98/06752 | 2/1998 |
| WO | WO 98/28427 | 7/1998 |
| WO | WO 98/30706 | 7/1998 |
| WO | WO 98/46257 | 10/1998 |
| WO | WO 98/52976 | 11/1998 |
| WO | WO 98/59244 | 12/1998 |
| WO | WO 99/02709 | 1/1999 |
| WO | WO 99/03887 | 1/1999 |
| WO | WO 99/29732 | 6/1999 |
| WO | WO 99/43713 | 9/1999 |
| WO | WO 99/52562 | 10/1999 |
| WO | WO 99/53958 | 10/1999 |
| WO | WO 99/60128 | 11/1999 |
| WO | WO 99/62944 | 12/1999 |
| WO | WO 99/66054 | 12/1999 |
| WO | WO00/11033 | 3/2000 |
| WO | WO 00/24893 | 5/2000 |
| WO | WO 00/34317 | 6/2000 |
| WO | WO00/40615 | 7/2000 |
| WO | WO 00/68376 | 11/2000 |
| WO | WO 00/78334 | 12/2000 |
| WO | WO 01/07081 A1 | 2/2001 |
| WO | WO 01/10912 | 2/2001 |
| WO | WO 01/36489 | 5/2001 |
| WO | WO 01/58957 | 8/2001 |
| WO | WO 02/02143 | 1/2002 |
| WO | WO 02/066514 | 8/2002 |
| WO | WO 02/072605 | 9/2002 |
| WO | WO 02/074783 | 9/2002 |
| WO | WO 02/079232 | 10/2002 |
| WO | WO 02/079415 | 10/2002 |
| WO | WO 00/69913 A1 | 11/2002 |
| WO | WO 02/090566 | 11/2002 |
| WO | WO 03/015697 | 2/2003 |
| WO | WO 03/048334 | 6/2003 |
| WO | WO 03/077834 | 9/2003 |

OTHER PUBLICATIONS

Capon et al., "Designing CD4 immunoadhesins for AIDS therapy", *Nature*, 337:525-530 (1989).

Gillies et al., "Expression of Human Anti-Tetanus toxoid antibody in Transfected Murine Myeloma Cells.", *Bio/Technology*, 7:799-804 (1989).

Gillies et al., "High-level expression of chimeric antibodies using adapted cDNA variable region cassettes", *J. Immuno. Methods*, 125:191-202 (1989).

Herrmann et al., "Hematopoeitic Responses With Advanced Malignancy Treated With Recombinant Human Granulocyte-Macrophage Colony-Stimulating Factor.", *J. Clin. Oncol.*, 7(2):159-167 (1989).

Pastan et al., "*Pseudomonas* Exotoxin: Chimeric Toxins", *J. Biol. Chem.*, 264 (No. 26):15157-15160 (1989).

Bacha et al., "Interleukin 2 Receptor-Targeted Cytotoxicity Interleukin 2 Receptor-mediated Action of a Diphtheria Toxin-related Interleukin 2 Fusion Protein", *J. Experimental Medicine*, 167:612-622 (1988).

Beutler et al., "Tumor Necrosis, Cachexia, Shock, and Inflammation: A Common Mediator", *Ann. Rev. Biochem.*, 57:505-518 (1988).

Chaudhary et al., "Selective killing of HIV-infected cells by recombinant human CD4-*Pseudomonas* exotoxin hybrid protein", *Nature*, 335:369-372 (1988).

Liu et al., "Hormone Conjugated with Antibody to CD3 Mediates Cytotoxic T Cell Lysis of Human Melanoma Cells", *Science*, 239:395-398 (1988).

Paul et al., (1988), "Lymphotoxin," *Ann. Rev. Immunol.*, 6:407-438.

Till et al., "HIV-Infected Cells are Killed by rCD4-Ricin A Chain", *Science*, 242:1166-1168 (1988).

Williams et al., "Diphtheria toxin receptor binding domain substitution with interleukin-2: genetic construction and properties of a diphtheria toxin-related interleukin-2 fusion protein", *Protein Engineering*, (No. 6):493-498 (1987).

Goeddel et al., "Tumor Necrosis Factors; Gene Structure and Biological Activities", pp. 597-609 (1986).

Jung et al., "Activation of human peripheral blood mononuclear cells by anti-T3: Killing of tumor target cells coated with anti-target-anti-T3 conjugates", *Proc. Natl. Acad. Sci. USA*, 83:4479-4483 (1986).

Murphy et al., "Genetic construction, expression, and melanoma-selective cytotoxicity of a diptheria toxin-related α-melanocyte-stimulating hormone fusion protein", *Proc. Natl. Acad. Sci. USA*, 83:8258-8262 (1986).

Perez et al., "Specific Targeting of Human Peripheral Blood T Cells by Heteroaggregates Containing Anti-T3 Crosslinked to Anti-Target cell antibodies", *J. Experimental Medicine*, 163:166-178 (1986).

Santon et al., "Effects of Epidermal Growth Factor Receptor Concentration on Tumorigenicity of A431 Cells in Nude Mice", *Cancer Research*, 46:4701-4705 (1986).

Shen et al., "Heteroantibody-Mediated Cytotoxicity: Antibody to the High Affinity Fc Receptor for IgG mediates cytotoxicity by Human Monocytes that is enhanced by interferon-λ and is not blocked by human IgG", *J. Immunology 137* (No. 11):3378-3382 (1986).

Henkart, "Mechanism of Lymphocyte-Mediated Cytotoxicity", *Ann. Rev. Immunol.*, 3:31-58 (1985).

Liu et al., "Heteroantibody Duplexes Target Cells for Lysis by Cytotoxic T Lymphocytes", *Proc. Natl. Acad. Sci. USA*, 82:8648-8652 (1985).

Nedwin et al., "Human Lymphotoxin and Tumor Necrosis Factor Genes: Structure, Homology and Chromosomal Localization", *Nucleic Acids Research*, 13 (No. 17):6361-6373 (1985).

Gasson et al., "Purified Human Granuloctye Macrophage Colony-Stimulating Factor: Direct Action on Neutrophils", *Science*, 226:1339-1339-1342 (1984).

Karpovsky et al., "Production of Target-Specific Effector Cells using Hetero-Cross Linked Aggregate Containing Anti-Target Cell and AntiFcλ Receptor Antibodies", *J. Experimental Medicine*, 160:1686-1701 (1984).

Kranz et al., "Attachment of an anti-receptor antibody to non-target cells renders them susceptible to lysis by a clone of cytotoxic T lymphocytes", *Proc. Natl. Acad. Sci. USA*, 81:7922-7926 (1984).

Neuberger, et al., "Recombinant Antibodies Possessing Novel Effector Functions.", *Nature*, 312:604-608 (1984).

Taniguchi et al. (1983) *Macmillan Journals Ltd*. "Structure and expression of a cloned cDNA for human interleukin-2".

Williams et al., Diphtheria Toxin Receptor Binding Domain Substitution with Interleukin-2 (Abstract).

Burgess et al., *J. of Cell Biol.*, 111:2129-2138.

Lazar et al., *Molecular and Cellular Biology*, 8:1247-1252.

Tao et al., *J. of Immunology*, 143:2595-2601.

Grimaldi et al., "The t(5;14) Chromosomal Translocation in a Case of Acute Lymphocytic Leukemia Joins the Interleukin-3 Gene to the Immunoglobulin Heavy Chain Gene," *Blood*, 73:2081-2805 (1989).

Chang et al., *Seminars in Surgical Oncology*, 5:285-90 (1989).

Rosenberg, *Immunology Today*, 9:58-62 (1989).

Schnee et al., *Proc. Natl. Acad. Sci. USA*, 84:6904-6908 (1987).

Chaudhary et al., *Nature*, 339:394-397 (1989).

Williams et al., *Gene*, 43:319-324 (1986).

Murphy, "Immunotoxins", *Kluwer Academic Publishers*, 123-140 (1988).

Bjorn et al., *Cancer Research*, 45:1214-1221 (1985).

Till et al., *Cancer Research*, 48:1119-1123 (1988).

Fell et al., *The J. of Immunology*, 146:2446-2452 (1991).

Hellstrom et al., *Proc. Natl. Acad Sci USA*, 83:7059-7063 (1986).

Senter et al., *Proc. Natl. Acad Sci USA*, 85:4842-4846 (1988).

Abaza et al. Journal of Protein Chemistry, 11(5):433-444, 1992.

Abstract XP-002116766, "Prostaglandins, their inhibitors and cancer" from Prostaglandins, Leukotrienes and Essential Fatty Acids (1996) 54(2):83-94.
Arenberg et al. (1996) "Interferon-γ-inducible Protein 10 (IP-10) Is an Angiostatic Factor That Inhibits Human Non-small Cell Lung Cancer (NSCLC) Tumorigenesis and Spontaneous Metastases," J. Exp. Med. 184:981-992.
Bachelot et al., "Retrovirus-Mediated Gene Transfer of an Angiostatin-Endostatin Fusion protein with Enhanced Anti-Tumor Properties In Vivo", Proceedings of the Annual Meeting of the American Association for Cancer Research, vol. 39, Mar. 1998, p. 271, Abstract #1856.
Barnett et al. (1994) "Purification, characterization and selective inhibition of human prostaglandin G/H synthase 1 and 2 expressed in the baculovirus system," Biochimica et Biophysica Acta, 1209:130-139.
Batova et al., "The Ch 14.18-GM-CSF Fusion Protein Is Effective at Mediating Antibody-dependent Cellular Cytotoxicity and Complement-dependent Cytotoxicity in Vitro," *Clinical Cancer Research*, 5: 4259-4263 (1999).
Becker et al., "Eradication of human hepatic and pulmonary melanoma metastases in SCID mice by antibody-interleukin 2 fusion proteins," *Proc. Natl. Acad. Sci. USA*, 93:2702-2707 (1996).
Boehm et al. (1997) "Antiangiogenic therapy of experimental cancer does not induce acquired drug resistance," Letters to Nature 390:404-407.
Boehm et al. (1998) "Zinc-Binding of Endostatin Is Essential for Its Antiangiogenic Activity," Biochemical and Biophysical Research Communications 252:190-194.
Brooks et al. (1994) "Integrin $\alpha_v\beta_3$ Antagonists Promote Tumor Regression by Inducing Apoptosis of Angiogenic Blood Vessels," Cell 79:1157-1164.
Canfield et al. (1991) "The Binding Affinity of Human IgG for its High Affinity Fc Receptor is Determined by Multiple Amino Acids in the CH2 Domain and Is Modulated by the Hinge Region," J. Exp. Med. 173: 1483-1491.
Cao et al. (1996) "Kringle Domains of Human Angiostatin," The Journal of Biological Chemistry 271 (46):29461-29467.
Cao et al. (1997) "Kringle 5 of Plasminogen is a Novel Inhibitor of Endothelial Cell Growth," The Journal of Biological Chemistry 272(36):22924-22928.
Chan et al. "Induction of Interferon γ Production by Natural Killer Cell Stimulatory Factor: Characterization of the Responder Cells and Synergy with Other Inducers," J. Exp. Med. 173: 869-879 (1991).
Chen et al., "Eradication of Murine Bladder Carcinoma by Intratumor Injection of a Bicistronic Adenoviral Vector Carrying cDNAs for the IL-12 Heterodimer and Its Inhibition by the IL-12 p40 Subunit Homodimer," J. Immunol. 159: 351-358 (1997).
Cheon et al. (1994) "High-affinity binding sites for related fibroblast growth factor ligands reside within different receptor immunoglobulin-like domains," Proc. Natl. Acad. Sci. USA 91: 989-993.
Cohen, S. L. et al., "Human leptin characterization," Nature, vol. 382, p. 589. (Aug. 15, 1996).
Cole et al. (1997) "Human IgG2 Variants of Chimeric Anti-CD3 Are Nonmitgenic to T Cells," J. of Immunology, 3613-3621.
Colombo et al. "Amount of Interleukin 12 Available at the Tumor Site is Critical for Tumor Regression," Cancer Res. 56: 2531-2534 (1996).
D'Amato et al. (1994) "Thalidomide is an inhibitor of angiogenesis," Proc. Natl. Acad. Sci. USA 91:4082-4085.
D'Andrea et al. "Production of Natural Killer Cell Stimulatory Factor (Interleukin 12) by Peripheral Blood Mononuclear Cells," J. Exp. Med. 176: 1387-1398 (1992).
Y-H Ding et al., "Zinc-Dependent Dimers Observed in Crystals of Human Edostatin," Proceedings of the National Academy of Sciences of USA, vol. 95, No. 18, pp. 10443-10448, Sep. 1988.
Earnest et al., "Piroxicam and Other Cyclooxygenase Inhibitors: Potential for Cancer Chemoprevention," J. Cell. Biochem, Supp, 161: 156-166 (1992).
Eisenthal, (1990) "Indomethacin up-regulated the generation of lymphokine-activated killer-cell activity and antibody-dependent cellular cytotoxicity mediated by interleukin-2," Cancer Immunol. Immunotherap. 31:342-348.
Friedman, J. M. et al., "Leptin and the regulation of body weight in mammals," Nature, vol. 395, pp. 763-770. (Oct. 22, 1998).
Gately et al. "The Interleukin-12/Interleukin-12 Receptor system: Role in Normal and Pathologic Immune Responses" Annu. Rev. Immunol. 16:495-521 (1998).
Gillessen et al., "Mouse Interleukin-12 (IL-12) p40 Homodimer: A Potent IL-12 Antagonist" Eur. J. Immunol. 25:200-206 (1995).
Gillies et al. "Antibody-Targeted Interleukin 2 Stimulates T-Cell Killing of Autologous Tumor Cells," Proc. Natl. Acad. Sci. 89: 1428-1432 (1992).
Gillies et al. "Biological Activity and In Vivo Clearance of Antitumor Antibody/Cytokine Fusion Proteins," Bioconj. Chem. 4: 230-235 (1993).
S. Gillies, et al. "Antibody-IL-12 fusion proteins are effective in SCID mouse models of prostrate colon carcinoma matastases," J. Immunol., vol. 160, No. 12, Jun. 15, 1998, pp. 6195-6203.
S.D. Gillies, et al: "Improving the efficacy of antibody-interleukin 2 fusion proteins by reducing their interaction with Fc receptors." Cancer Research. (May 1, 1999) 59 (9) pp. 2159-2166. Journal Code: CNF, ISSN: 0008-5472., XP002107035.
Gillis et al. (1978) "T Cell Growth Factor: Parameters of Production And A Quantitative Microassay for Activity," J. of Immunol. 6:2027-2032.
E.Y. Gren et al., "A New Type of Leukocytic Interferon". 1983. Dokl. Biochem. 269: 91-95.
Guyre et al., "Increased potency of Fc-receptor-targeted antigen," *Cancer Immunol. Immunother*. 45: 146-148 (1997).
E.T. Harvill, et al. "In vivo properties of an IgG3-IL-2 fusion protein: A gneral strategy for immune potentiation." J. Immunol. (Oct. 1, 1996) 157 (7) pp. 3165-3170. Journal Code: IFB. ISSN: 0022-1767., XP002107033.
Hazama et al. "Adjuvant-Independent Enhanced Immune Responses to Recombinant Herpes Simplex Virus Type 1 Glycoprotein D by Fusion with Biologically Active Interleukin-2," Vaccine 11: 629-636 (1993).
He et al. (1998) "Humanization and Pharmacokinetics of Monoclonal Antibody with Specificity for Both E- and P-Selectin," J. Immunol. 1029-1035.
Heinzel et al. "In Vivo Production and Function of IL-12 p40 Homodimers" In Vivo Biology of IL-12 p40 Homodimer, 4381-4388 (1997).
Hohenester et al., "Crystal Structure of the Angiogenesis Inhibitor Endostatin at 1/5 Å Resolution", EMBO Journal, vol. 17, No. 6, pp. 1656-1664, 1998.
Hoogenboom et al., "Construction and expression of antibody-tumor necrosis factor fusion proteins," Molecular Immunology, vol. 28, No. 9, 1027-1037 (1991).
Huck et al. (1986) "Sequence of a human immunoglobulin gamma 3 heavy chain constant region gene: comparison with the other human Cγ genes," Nucleic Acids Research 14:1779-1789.
Huse et al. (1989) "Generation of a Large Combinatorial Library of the Immunoglobulin Repertoire in Phage Lambda," Science 246:1275-1281.
Ingber et al. (1990) "Synthetic analogues of fumagillin that inhibit angiogensis and suppress tumour growth," Nature 348:555-557.
Jones et al., (1986) "Replacing the complementarity-determining regions in a human antibody with those from a mouse," Nature 321:522-525.
Junghans et al. (1996) "The protection receptor of IgG catabolism is the B2-micorgobulin-containing neonatal intestinal transport receptor," Proc. Natl. Acad. Sci. USA 93:5512-5516.
Kang et al. (1991) "Antibody redesign by chain shuffling from random combinatorial immunoglobulin libraries," Proc. Natl. Acad. Sci. USA 88:11120-11123.
Kappel, et al. (1992) Current Opinion in Biotechnology 3:548-553.
Kendra et al., "Pharmacokinetics and stability of the ch 14.18-interleukin-2 fusion protein in mice," *Cancer Immunol. Immunother*., 48: 219-229 (1999).
T. Kim, et al., "An ovalbumin-IL-12 fusion protein is more effective than oval bumin plus free recombinant IL-12 in inducing a T helper cell type 1-dominated immune response and inhibiting antigen-specific IgE production." J. Immunol., vol. 158, No. 9, May 1, 1997, pp. 4137-4144.

LaVallie et al. (1993) "Cloning and Functional Expression of a cDNA Encoding the Catalytic Subunit of Bovine Enterokinase," J. of Biological Chemistry 268:23311-23317.
LeBerthon et al. (1991) "Enhanced Tumor Uptake of Macromolecules Induced by a Novel Vasoactive Interleukin 2 Immunoconjugate" Cancer Research 51:2694-2698.
G. Lieschke, et al.: "Bioactive murine and human interleukin-12 fusion proteins which retain antitumor activity in vivo." Nature Biotechnology, vol. 15, No. 1, Jan. 1997, pp. 35-40.
Linsley et al. (1991) "CTLA-4 is a Second Receptor for B Cell Activation Antigen B7," J. Exp. Med. 174; 561-569.
Lo et al., "High Level Expression and Secretion of Fc-X Fusion Proteins in Mammalian Cells". XP-002143888. (1998). Protein Engineering 1:495-500.
Lode et al. *Amplification of T Cell Mediated Immune Responses by Antibody-Cytokine Fusion Proteins*. Immunological Investigations 2000, vol. 29, No. 2, pp. 117-120.
Lode et al. (1998) "Natural Killer Cell-Mediated Eradication of Neuroblastoma Metastases to Bone Marrow by Targeted Interleukin-2 Therapy," Blood 91:1706-1715.
Lode et al., "Synergy between an antiangiogenic integrin $\alpha_v$ antagonist and an antibody-cytokine fusion protein eradicates spontaneous tumor metastases," Proc. Natl. Acad. Sci. USA 96:1591-1596 (1999).
Lode et al., "Tumor-targeted IL-2 amplifies T cell-mediated immune response induced by gene therapy with single-chain IL-12," 96:8591-8596 (1999).
Maloney et al. (1994) "Phase I Clinical Trial Using Escalating Single-Dose Infusion of Chimeric Anti-CD20 Monoclonal Antibody (IDEC-C2B8) in Patients with Recurrent B-Cell Lymphoma," Blood 84:2457-2466.
Martinotti et al. "CD4 T Cells Inhibit in vivo the CD8-Mediated Immune Response Against Murine Colon Carcinoma Cells Transduced with Interleukin-12 Genes," Eur. J. Immunol. 25: 137-146 (1995).
M. Mark, et al.: "Expression and characterization of hepatocyte growth factor receptor-IgG fusion proteins." J. Biol. Chem., vol. 267, No. 36 Dec. 25, 1992, pp. 26166-26171.
Medesan et al. (1997) "Delineation of the Amino Acid Residues Involved in Transcytosis and Catabolism of Mouse IgG1[1] ," J. Immunol. I2211-2217.
Mestre et al. (1997) "Retinoids Suppress Epidermal Growth Factor-induced Transcription of cyclooxygenase-2 in Human Oral Squamous Carcinoma Cells," Cancer Research 57:2890-2895.
Mosmann and Coffman, "TH1 and TH2 Cells: Different Patterns of Lymphokine Secretion Lead to Different Functional Properties," Ann. Rev. Immunol. 7: 145-173 (1989).
O'Reilly et al. (1994) "Angiostatin: A Novel Angiogenesis Inhibitor That Mediates the Suppression of Metastases by a Lewis Lung Carcinoma," Cell 79:315-328.
O'Reilly et al. (1996) "Angiostatin induces and sustains dormancy of human primary tumors in mice," Nature Medicine 2(6):689-692.
O'Reilly et al. (1997) "Endostatin: An Endogenous Inhibitor of Angiogenesis and Tumor Growth," Cell 88:277-285.
Perez et al. (1989) "Isolation and Characterization of a cDNA Encoding the KS1/4 Epithelial Carcinoma Marker," J. Immunol. 142:3662-3667.
Putzer et al. "Interleukin 12 and B7-1 Costimulatory Molecule Expressed by an Adenovirus Vector Act Synergistically to Facilitate Tumor Regression," Proc. Nat'l Acad. Sci. 94: 10889-10894 (1997).
Reisfeld et al. *Immunocytokines: a new approach to immunotherapy of melanoma*. Melanoma Research 1997, vol. 7. Suppl. 2, pp. S99-S106.
Reisfeld, et al.: "Recombinant antibody fusion proteins for cancer immunotherapy." Current Topics in Microbiology and Immunolgy, (1996) 213 (PT 3) pp. 27-53. Ref: 67 Journal Code; DWQ. ISSN:0070-217X., XP002107034.
Riethmuller et al. (1994) "Randomised trial of monoclonal antibody for adjuvant therapy of resected Dukes' C colorectal carcinoma," The Lancet 343:1177-1183.
Sasaki et al. (1998) "Structure, function and tissue forms of the C-terminal globular domain of collagen XVII containing the angiogenesis inhibitor endostatin," The EMBO Journal 17(15):4249-4256.
Schoenhaut et al. "Cloning and Expression of Murine IL-12," J. Immunol. 148: 3433-3340 (1992).
Shiff et al., "Sulindac Sulfide, an Asprin-like Compound, Inhibits Proliferation, Causes Cell Cycle Quiescence, and Induces Apoptosis in HT-29 Colon Adenocarcinoma Cells," J. Clin. Invest. 96:491-503 (1995).
Sim et al. (1997) "A Recombinant Human Angiostatin Protein Inhibits Experimental Primary and Metastatic Cancer," Cancer Research 57:1329-1334.
Stevenson et al. (1997) "Conjugation of Human Fcγ in Closed-Hinge or Open-Hinge Configuration to Fab'γ and Analogous Ligands," *J. of Immunology*, vol. 158, pp. 2242-2250.
Tao et al. (1993) "Structural Features of Human Immunoglobulin G that Determine Isotype-Differences in Copmlement Activation," J. Exp. Med. 178: 661-667.
Teicher et al., (1994) "Potentiation of Cytotoxic Cancer Therapies by TNP-470 Alone and With Other Anti-Angiogenic Agents", Int. J. Cancer, 57, 920-925.
*The Merck Manual of Diagnosis and Therapy*, 990-993, 1278-1283 ($17^{th}$ ed. 1999).
Trinchieri, "Interleukin-12: A Cytokine Produced by Antigen-Presenting Cells With Immunoregulatory Functions in the Generation of T-Helper Cells Type 1 and Cytotoxic Lymphocytes," Blood 84: 4008-4027 (1994).
Vagliani et al. "Interleukin 12 Potentiates the Curative Effect of a Vaccine Based on Interleukin 2-transduced Tumor Cells," Cancer Res. 56: 467-470 (1996).
Varki et al. (1984) "Antigens Associated with a human lung adenocarcinoma defined by monoclonal antibodies," Cancer Research 44:681-687.
Verhoeyen et al. (1988) "Reshaping Human Antibodies: Grafting an Antilysozyme Activity," Science 239:1534-1536.
Wooley et al. (1993) "Influence of a Recombitant Human Soluble Tumor Necrosis Factor Receptor FC Fusion Protein on Type II Collagen-Induced Arthritis in Mice," J. Immunol. 151: 6602-6607.
Wu et al., "Suppression of Tumor Growth with Recombinant Murine Angiostatin", Biochemical and Biophysical Research Communications, US, Academic Press Inc., vol. 236, No. 3, Jul. 30, 1997, pp. 651-654.
Xiang et al. (1997) "Elimination of Established Murine Colon Carcinoma Metastases by Antibody-Interleukin 2 Fusion Protein Therapy," Cancer Research 57:4948-4955.
Xin Xau Zheng, et al: "Administration of nonstyolytic IL-10/Fc in muring models of lipopolysaccaride-induced septic shock and allogenic islet transplantation." J. Immunol., 1995, 154(10), pp. 5590-5600 CODEN: JOIMA3; ISSN; 0022-1767, XP002082460.
Baselga, et al (1998) "Recombinant Humanized Anti-HER2 Antibody (Herceptin ™) Enhances the Antitumor activity of Paclitazel and Doxorubicin against HER3/*neu* Overexpressing Human Breast Cancer Xenografts." Cancer Research 58:2825-2831.
Holden, et al. (2001) "Augmentation of Anti-Tumor Activity of KS-IL2 Immunoctyokine with Chemotherapeutic Agents." Proceedings of the American Association for Cancer Research, vol. 42, p. 683.
Holden, et al. (2001) "Augmentation of Antitumor activity of an Antibody-Interleukin 2 Immunocytokine with Chemotherapeutic Agents" Clinical Cancer Research; vol. 7, No. 9, pp. 2862-2869.
Kim, et al. (1999) "Cytokine Molecular Adjuvants Modulate Immune Responses Induced by DNA Vaccine Constructs for HIV-1 and SIV" Journal of Interferon and Cytokine Research 19:77-84.
Rozwarski, et al. (1994) "Structural comparisons among the short-chain helical cytokines" Structure 2: 159-173.
Kuo, et al. (2001) "Oligomerization-dependent Regulation of Motility and Morphogenesis by the Collagen XVIII NC1/Endostatin Domain," J. Cell Bio. 152:1233-1246.
Afonso et al., (1994) "The Adjuvant of Interleukin-12 in a Vaccine Against *Leishmania major* ," *Science*, 263:235-237.
Becker et al., (1996) "An Antibody-Interleukin 2 Fusion Protein Overcomes Tumor Heterogeneity by Induction of a Cellular Immune Response," *Proc. Natl. Acad. Sci.*, 93:7826-7831.
Buchli et al., (1993) "Structural and Biologic Properties of a Human Aspartic Acid-126 Interleukin-2 Analog," *Archives of Biochemistry and Biophysics*, 307:411-415.

Chang et al., (1996) "A Point Mutation in Interleukin-2 that Alters Ligand Internalization," *Journal of Biological Chemistry*, 271:13349-13355.

Collins et al., (1988) "Identification of Specific Residues of Human Interleukin 2 that Affect Binding to the 70-kDa Subunit (p70) of the Interleukin 2 Receptor," *Proc. Natl. Acad. Sci*, 85:7709-7713.

Hellström et al., (1986) "Antitumor effects of L6, and IgG2a antibody that reacts with most human carcinomas," *Proc. Natl. Acad. Sci.*, 83:7059-7063.

Hu et al., (1996) "A Chimeric Lym-1/Interleukin 2 Fusion Protein for Increasing Tumor Vascular Permeability and Enhancing Antibody Uptake," *Cancer Research*, 56:4998-5004.

Ju et al., (1987) "Structure-Function Analysis of Human Interleukin-2," *Journal of Biological Chemistry*, 262:5723-5731.

Mott et al., (1995) "The Solution Structure of the F42A Mutant of Human Interleukin 2," *J. Mol. Biol.*, 247:979-994.

Roessler et al., (1994) Cooperative Interactions between the interleukin 2 receptor α and β chains alter the interleukin 2-binding affinity of the receptor subunits, *Proc. Natl. Acad. Sci.*, 91:3344-3347.

Sauve et al., (1991) "Localization in human interleukin 2 of the binding site of the α chain (p55) of the interleukin 2 receptor," *Proc. Natl. Acad. Sci.*, 88:4636-4640.

Senter et al., (1988) "Anti-tumor effects of antibody-alkaline phosphatase conjugates in combination with etoposide phosphate," *Proc. Natl. Acad. Sci.*, 85:4842-4846.

Shanafelt et al., (2000) "A T-cell-selective interleukin 2 mutein exhibits potent antitumor activity and is well tolerated in vivo," *Nature Biotechnology*, 18:1197-1202.

Angal et al., (1993), "A Single Amino Acid Substitution Abolishes the Heterogeneity of Chimeric Mouse/Human (IgG4) Antibody," *Molecular Immunology*, 30(1):105-108.

Batra et al., (1993), "Insertion of Constant Region Domains of Human IgG1 into CD4-PE40 Increases Its Plasma Half-Life," *Molecular Immunology*, 30(4):379-386.

Becker et al., (1996), "Long-lived and Transferable Tumor Immunity in Mice after Targeted Interleukin-2 Therapy," *J. Clin. Invest.*, 98(12):2801-2804.

Becker et al., (1996), "T Cell-mediated Eradication of Murine Metastatic Melanoma Induced by Targeted Interleukin-2 Therapy," *J. Exp. Med.*, 183(50):2361-2366.

Bissery et al., (1997), "The Taxoids," in *Cancer Therapeutics: Experimental and Clinical Agents*, Teicher (ed.), pp. 175-193.

Bitonti et al., (2002), "Transepithelial Absorption of an Erythropoietin-Fc Fusion Protein After Delivery to the Central Airways," *Respiratory Drug Delivery*, 8:309-312.

Boissel et al., (1993), "Erythropoietin Structure-Function Relationships: Mutant Proteins that Test a Model of Tertiary Structure," *The Journal of Biological Chemistry*, 268(21):15983-15993.

Briggs et al., (1974), "Hepatic Clearance of Intact and Desialylated Erythropoietin," *American Journal of Physiology*, 227(6):1385-1388.

Caton et al., (1986) "Structural and Functional Implications of a Restricted Antibody Response to a Defined Antigenic Region on the Influenza Virus Hemagglutinin," *The EMBO Journal*, 5(7):1577-1587.

Chuang et al., (1993), "Effect of New Investigational Drug Taxol on Oncolytic Activity and Stimulation of Human Lymphocytes," *Gynecologic Oncology*, 49:291-298.

Chuang et al., (1994), "Alteration of Lymphoctye Microtubule Assembly, Cytotoxicity, and Activation by the Anticancer Drug Taxol," *Cancer Research*, 54:1286-1291.

Cruse et al., (eds.), (1995), *Illustrated Dictionary of Immunology*, pp. 156-157, CRC Press, NY.

Darling et al., (2002), "Glycosylation of Erythropoietin Affects Receptor Binding Kinetics: Role of Electrostatic Interactions," *Biochemistry*, 41:14524-14531.

Davis et al., (2003), "Immunocytokines: Amplification of Anti-cancer Immunity," *Cancer Immunol. Immunother.*, 52:297-308.

Dolman et al., (1998), "Suppression of Human Prostate Carcinoma Metastases in Severe Combined Immunodeficient Mice by Interleukin 2 Immunoctyokine Therapy," *Clin. Cancer Research.*, 4(10):2551-2557.

Duncan et al., (1998), "The Binding Site for C1q on IgG," *Nature*, 332:738-740.

Egrie et al., (2001), "Development and Characterization of Novel Erythropoiesis Stimulating Protein (NESP)," *Nephrol. Dial. Transplant.*, 16(Supp 3):3-13.

Elliott et al., (1997), "Mapping of the Active Site of Recombinant Human Erythropoietin," *Blood*, 89(2):493-502.

Fell et al., (1992), "Chimeric L6 Anti-tumor Antibody: Genomic Construction, Expression, and Characterization of the Antigen Binding Site," *J. Biological Chemistry*, 267:15552-15558.

Fibi et al., (1995), "N- and O-Glycosylation Muteins of Recombinant Human Erythropoietin Secreted From BHK-21 Cells," *Blood*, 85(5):1229-1236.

Frost et al., (1997), "A Phase I/IB Trial of Murine Monoclonal Anti-GD2 Antibody 14.G2a Plus Interleukin-2 in Children with Refractory Neuroblastoma," *Cancer*, 80(2):317-333.

Gan et al., (1999), "Specific Enzyme-linked Immunosorbent Assays for Quantitation of Antibody-cytokine Fusion Proteins," *Clinical and Diagnostic Laboratory Immunology*, 6(2):236-42.

Gillies et al., (1991), "Expression of Genetically Engineered Immunoconjugates of Lymphotoxin and a Chimeric Anti-ganglioside GD2 Antibody," *Hybridoma.*, 10(3):347-56.

Gillies et al., (2002), "Bi-functional Cytokine Fusion Proteins for Gene Therapy and Antibody-targeted Treatment of Cancer," *Cancer Immunol. Immunother.*, 51(8):449-60.

Gillies et al., (2002), "Improved Circulating Half-life and Efficacy of an Antibody-interleukin 2 Immunocytokine Based on Reduced Intracellular Proteolysis," *Clin. Cancer Research*, 8(1):210-216.

Greene et al., (1975), "Neuronal Properties of Hybrid Neuroblastoma X Sympathetic Ganglion Cells," *Proc. Natl. Acad. Sci. USA*, 72(12):4923-4927.

Griffon-Etienne et al., (1999), "Taxane-induced Apoptosis Decompresses Blood Vessels and Lowers Interstitial Fluid Pressure in Solid Tumors: Clinical Implications," *Cancer Research*, 59:3776-3782.

Hammerling et al., (1996), "In Vitro Bioassay for Human Erythropoietin Based on Proliferative Stimulation of an Erythroid Cell Line and Analysis of Carbohydrate-dependent Microheterogeneity," *Journal of Pharmaceutical and Biomedical Analysis*, 14:1455-1469.

Hank et al., (1996), "Activation of Human Effector Cells by a Tumor Reactive Recombinant Anti-ganglioside GD2 Interleukin-2 Fusion Protein (ch14.18-IL2)," *Clin Cancer Research*, 2(12):1951-1959.

Hank et al., (2003), "Determination of Peak Serum Levels and Immune Response to the Humanized Anti-ganglioside Antibody-interleukin-2 Immunocytokine," in *Methods in Molecular Medicine, vol. 85: Novel Anticancer Drug Protocols*, Buolamwini et al., (eds.), pp. 123-131, Humana Press Inc., Totowana, NJ.

Haraguchi, (1994), "Isolation of GD3 Synthase Gene by Expression Cloning of GM3 α-2,8-sialyltransferase cDNA using anti-GD2 Monoclonal Antibody," *Proc. Natl. Acad. Sci. USA*, 91(22):10455-10459.

Harris, (1995), "Processing of C-terminal Lysine and Arginine Residues of Proteins Isolated from Mammalian Cell Culture," *J. Chromatography A*, 705:129-134.

Harvill et al., (1995), "An IgG3-IL2 Fusion Protein Activates Complement, Binds FcγRI, Generates LAK Activity and Shows Enhanced Binding to the High Affinity IL-2R," *Immunotechnology*, 1:95-105.

Heijnen et al., (1996), "Antigen Targeting to Myeloid-specific Human FcγRI/CD64 Triggers Enhanced Antibody Responses in Transgenic Mice," *J. Clin Invest.*, 97(2):331-338.

Hezareh et al., (2001), "Effector Function Activities of a Panel of Mutants of a Broadly Neutralizing Antibody against Human Immunodeficiency Virus Type 1," *J. Virology*, 75(24):12161-12168.

Hornick et al., (1999), "Pretreatment with a Monoclonal Antibody/Interleukin-2 Fusion Protein Directed Against DNA Enhances the Delivery of Therapeutic Molecules to Solid Tumors," *Clin. Cancer Research*, 5:51-60.

Idusogie et al., (2000), "Mapping of the C1q Binding Site on Rituxan, a Chimeric Antibody with a Human IgG1 Fc," *J. Immunology*, 164(8):4178-4184.

Imboden et al., (2001), "The Level of MHC Class I Expression on Murine Adenocarcinoma Can Change the Antitumor Effector Mechanism of Immunocytokine Therapy," *Cancer Research*, 61(4):1500-7.

Kato et al., (1997), "Mechanism for the Nonlinear Pharmacokinetics of Erythropoietin in Rats," *The Journal of Pharmacology and Experimental Therapeutics*, 283:520-527.

Kato et al., (1998), "Pharmacokinetics of Erythopoietin in Genetically Anemic Mice," *Drug Metabolism and Disposition*, 26(2):126-131.

Kitamura et al., (1989), "Establishment and Characterization of a Unique Human Cell Line that Proliferates Dependently on GM-CSF, IL-3, or Erythropoietin," *Journal of Cellular Physiology*, 140:323-334.

Kushner et al., (2001), "Phase II Trial of the Anti-GD2 Monoclonal Antibody 3F8 and Granulocyte-Macrophage Colony-Stimulating Factor for Neuroblastoma," *J. Clinical Oncology*, 19(22):4189-94.

Liu et al., (1998), "Immunostimulatory CpG Oligodeoxynucleotides Enhance the Immune Response to Vaccine Strategies Involving Granulocyte-Macrophage Colony-Stimulating Factor," *Blood*, 92(10):3730-3736.

Locatelli et al., (2001), "Darbepoetin alfa Amgen," *Current Opinion in Investigational Drugs*, 2:1097-1104.

Lode et al., (1997), "Targeted Interleukin-2 Therapy for Spontaneous Neuroblastoma Metastases to Bone Marrow," *J. Natl. Cancer Inst.*, 89(21):1586-94.

Lode et al., (1998), "Immunocytokines: A Promising Approach to Cancer Immunotherapy," *Pharmacol. Ther.*, 80(3):277-292.

Lode et al., (2000), "What To Do With Targeted IL-2," *Drugs of Today*, 36(5):321-336.

Lode et al., (2000), "Melanoma Immunotherapy by Targeted IL-2 Depends on CD4(+) T-cell Help Mediated by CD40/CD40L Interaction," *J. Clin. Invest.*, 105(11):1623-30.

Macdougall, (2002), "Optimizing the Use of Erythropoietic Agents—Pharmacokinetic and Pharmacodynamic Considerations," *Nephrol. Dial. Transplant.*, 17(Supp 5):66-70.

Metelitsa et al., (2002), "Antidisialoganglioside/granulocyte Macrophage-colony-stimulating Factor Fusion Protein Facilitates Neutrophil Antibody-dependent Cellular Cytotoxicity and Depends on FcγRII (CD32) and Mac-1 (CD11b/CD18) for Enhanced Effector Cell Adhesion and Azurophil Granulate Exocytosis," *Blood*, 99(11):4166-73.

Mueller et al., (1997), "Humanized Porcine VCAM-specific Monoclonal Antibodies with Chimeric IgG2/G4 Constant Regions Block Human Leukocyte Binding to Porcine Endothelial Cells," *Molecular Immunology*, 34(6):441-452.

Mullins et al., (1997), "Taxol-mediated Changes in Fibrosarcoma-induced Immune Cell Function: Modulation of Antitumor Activities," *Cancer Immunol. Immunother*, 45:20-28.

Mullins et al., (1998), "Interleukin-12 Overcomes Paclitaxel-mediated Suppression of T-cell Proliferation," *Immunopharmacol. Immunotoxicol.*, 20(4):473-492.

Naramura et al., (1994), "Mechanisms of Cellular Cytotoxicity Mediated by a Recombinant Antibody-IL2 Fusion Protein Against Human Melanoma Cells," *Immunology Letters*, 39:91-99.

Neal et al., (2003), "NXS2 Murine Neuroblastomas Express Increased Levels of MHC Class I Antigens upon Recurrence Following NK-dependent Immunotherapy," *Cancer Immunol. Immunother.*, 53:41-52.

Netti et al., (1995), "Time-dependent Behavior of Interstitial Fluid Pressure in Solid Tumors Implications for Drug Delivery," *Cancer Research*, 55:5451-5458.

Netti et al., (1999), "Enhancement of Fluid Filtration Across Tumor Vessels: Implication for Delivery of Macromolecules," *Proc. Nat. Acad. Sci. USA*, 96:3137-3142.

Ngo et al., (1994) "Computational Complexity, Protein Structure Prediction, and the Levinthal Paradox," in *The Protein Folding Problem and Tertiary Structure Prediction*, Merz et al. (eds.), pp. 433-440 and 492-495, Birkhauser, Boston, MA.

Niethammer et al., (2002) "An Oral DNA Vaccine Against Human Carcinoembryonic Antigen (CEA) Prevents Growth and Dissemination of Lewis Lung Carcinoma in CEA Transgenic Mice," *Vaccine*, 20:421-429.

Niethammer et al., (2001) "Targeted Interleukin 2 Therapy Enhances Protective Immunity Induced by an Autologous Oral DNA Vaccine against Murine Melanoma, " *Cancer Research*, 61(16):6178-84.

Nimtz et al., (1993), "Structures of Sialylated Oligosaccharides of Human Erythropoietin Epxressed in Recombinant BHK-21 Cells," *Eur. J. Biochem.*, 213:39-56.

Pancook et al., (1996), "Eradication of Established Hepatic Human Neuroblastoma Metastases in Mice with Severe Combined Immunodeficiency by Antibody-targeted Interleukin-2," *Cancer Immunol. Immunother.*, 42(2):88-92.

Park et al., (2000), "Efficiency of Promoter and Cell Line in High-level Expression of Erythropoietin," *Biotechnol. Appl. Biochem.*, 32:167-172.

Polizzi et al., (1999), "A Novel Taxane with Improved Tolerability and Therapeutic Activity in a Panel of Human Tumor Xenografts," *Cancer Research*, 59:1036-1040.

Reisfeld et al., (1996), "Antibody-interleukin 2 Fusion Proteins: A New Approach to Cancer Therapy," *J. Clin. Lab. Anal.*, 10:160-166.

Reisfeld et al., (1996), "Involvement of B Lymphocytes in the Growth Inhibition of Human Pulmonary Melanoma Metastases in Athymic *nu/nu* Mice by an Antibody-lymphotoxin Fusion Protein," *Cancer Research*, 56(8):1707-1712.

Roitt et al., (1993), "The Role of TH Cells in the Selection of Effector Mechanisms Directed Against Target Antigens," *Immunology* 3rd Ed., pp. 8.3-8.4.

Ruehlmann et al., (2001), "MIG (CIXCL9) Chemokine Gene Therapy Combines with Antibody-cytokine Fusion Protein to Suppress Growth and Dissemination of Murine Colon Carcinoma," *Cancer Research*, 61(23):8498-503.

Sabzevari et al., (1994), "A Recombinant Antibody-interleukin 2 Fusion Protein Suppresses Growth of Hepatic Human Severe Combined Immunodeficiency Mice," *Proc. Natl. Acad. Sci. USA*, 91(20):9626-30.

Seidenfeld et al., (2001), "Epoietin Treatment of Anemia Associated with Cancer Therapy: A Systematic Review and Meta-analyis of Controlled Clinical Trials," *Journal of National Cancer Institute*, 93(16):1204-1214.

Sharma et al., (1999), "T cell-derived IL-10 Promotes Lung Cancer Growth by Suppressing Both T cell and APC Function," *Journal of Immunology*, 163:5020-5028.

Shinkawa et al., (2003), "The Absence of Fucose But Not the Presence of Galactose or Bisecting N-Acetylglucosamine of Human IgG1 Complex-type Oligosaccharides Shows the Critical Role of Enhancing Antibody-dependent Cellular Cytotoxicity," *J. Biol. Chem.*, 278:3466-3473.

Spiekermann et al., (2002), "Receptor-mediated Immunoglobulin G Transport Across Mucosal Barriers in Adult Life: Functional Expression of FcRn in the Mammalian Lung," *J. Exp. Med.*, 196:303-310.

Strom et al., (1996), "Therapeutic Approach to Organ Transplantation," Chapter 36, pp. 451-456, in *Therapeutic Immunology*, Austen et al., (eds.), Blackwell Science.

Sulitzeanu, (1993), "Immunosuppressive Factors in Human Cancer," pp. 247-266 in *Advances in Cancer Research, vol. 60*, Vande Woude et al., (eds.), Academic Press, Inc.

Syed et al., (1998), "Efficiency of Signaling Through Ctyokine Receptors Depends Critically on Receptor Orientation," *Nature*, 395:511-516.

Thommesen et al., (2000), "Lysine 322 in the Human IgG3 CH2 Domain is Crucial for Antibody Dependent Complement Activation," *Mol. Immunol.*, 37(16):995-1004.

Villunger et al., (1997), "Constitutive Expression of Fas (Apo-1/CD95) Ligand on Multiple Myeloma Cells: A Potential Mechanism of Tumor-induced Suppression of Immune Surveillance," *Blood*, 90(1):12-20.

Watanabe et al., (1997), "Long-term Depletion of Naive T cells in Patients Treated for Hodgkin's Disease," *Blood*, 90(9):3662-3672.

Wells, (1990), "Additivity of Mutational Effect in Proteins," *Biochemistry*, 29(37):8509-8517.

Wen et al., (1993), "Erythropoietin Structure-Function Relationships: High Degree of Sequence Homology Among Mammals," *Blood*, 82(5):1507-1516.

Xiang et al., (1998), "Induction of Persistent Tumor-protective Immunity of Mice Cured of Established Colon Carcinoma Metastases," *Cancer Research*, 58(17):3918-3925.

Xiang et al., (1999) "T Cell Memory against Colon Carcinoma is Long-lived in the Absence of Antigen," *J. Immunology*, 163(7):3676-83.

Xiang et al., (2001), "A Dual Function DNA Vaccine Encoding Carcinoembryonic Antigen and CD40 Ligand Trimer Induces T Cell-mediated Protective Immunity Against Colon Cancer in Carcinoembryonic Antigen-Transgenic Mice," *J. Immunology*, 167(8):4560-5.

Xiang et al., (2001), "Protective Immunity Against Human Carcinoembryonic Antigen (CEA) Induced by an Oral DNA Vaccine in CEA-transgenic Mice," *Clinical Cancer Research*7(3 Supp):S856-S864.

Xu et al., (1994), "Residue at Position 331 in the IgG1 and IgG4 CH2 Domains Contributes to Their Differential Ability to Bind and Activate Complement," *J. Biol. Chem*., 269(5):3469-3474.

Yu et al., (1998), "Phase I Trial of a Human-Mouse Chimeric Anti-Disaloganglioside Monoclonal Antibody ch14.18 in Patients with Refractory Neuroblastoma and Osteosarcoma," *J. Clinical Oncology*, 16(6):2169-80.

Zagozdzon et al., (1999), "Potentiation of Antitumor Effects of IL-12 in Combination with Paclitaxel in Murine Melanoma Model In Vivo," *International Journal of Molecular Medicine*, 4:645-648.

Chapman et al., (1994), "Mapping Effector Functions of a Monoclonal Antibody to GD3 by Characterization of a Mouse-Human Chimeric Antibody," *Cancer Immuno. Immunother*., 39:198-204.

Conner et al., (2004), "Ex vivo Evaluation of Anti-EpCAM Immunocytokine huKS-IL2 in Ovarian Cancer," *J. Immunotherapy*, 27:211-219.

de la Salle et al., (1996), "FcγR on Human Dendritic Cells," in *Human IgG Receptors*, pp. 39-55, van de Winkel et al. (eds.), R.G. Landes Co.

Dorai et al., (1991), "Aglycosylated Chimeric Mouse/Human IgG1 Antibody Retains Some Effector Function," *Hybridoma*, 10(2):211-217.

Dorai et al., (1992), "Role of Inter-Heavy and Light Chain Disulfide Bonds in the Effector Functions of Human IgG1," *Molecular Immunology*, 29(12):1487-1491.

Elliott et al., (1996), "Fine-Structure Epitope Mapping of Antierythropoietin Monoclonal Antibodies Reveals a Model of Recombinant Human Erythropoietin Structure," *Blood*, 87(7):2702-2713.

Gillies et al., (1991), "Targeting Human Cytotoxic T Lymphocytes to Kill Heterologous Epidermal Growth Factor Receptor-Bearing Tumor Cells: Tumor-Infiltrating Lymphocyte/Hormone Receptor/Recombinant Antibody," *J. Immunology*, 146(3):1067-1071.

Handgretinger et al., (1995), "A Phase I Study of Human/Mouse Chimeric Anti-ganglioside GD2 Antibody ch14.18 in Patients with Neuroblastoma," *European J. Cancer*, 31A(2):261-267.

Hurn et al., (1980), "Production of Reagent Antibodies," *Methods in Enzymology*, 70: 104-142.

Isenman et al., (1975), "The Structure and Function of Immunoglobulin Domains: II. The Importance of Interchain Disulfide Bonds and the Possible Role of Molecular Flexibility in the Interaction between Immunoglobulin G and Complement," *J. Immunology*, 114(6):1726-1729.

Ko et al., (2004), "Safety, Pharmacokinetics, and Biological Pharmacodynamics of the Immunocytokine EMD 273066 (huKS-IL2)," *J. Immunotherapy*, 27:232-239.

Lo et al., (1992), "Expression and Secretion of an Assembled Tetrameric CH2-deleted Antibody in *E. coli*.," *Hum. Antibod. Hybridomas*, 3:123-128.

Maecker et al., (1997), "DNA Vaccination with Cytokine Fusion Constructs Biases the Immune Reponse to Ovalbumin," *Vaccine*, 15(15):1687-1696.

Mueller et al., (1990), "Enhancement of Antibody-Dependent Cytotoxicity With A Chimeric Anti-GD2 Antibody," *J. Immunology*144(4):1382-1386.

Mueller et al., (1990), "Serum Half-Life and Tumor Localization of a Chimeric Antibody Deleted of the CH2 Domain and Directed Against the Disialoganglioside GD2," *Proc. Natl. Acad. Sci. USA*., 87:5702-5705.

Naramura et al., (1993), "Therapeutic Potential of Chimeric and Murine Anti-(Epidermal Growth Factor Receptor) Antibodies in a Metastasis Model for Human Melanoma," *Cancer Immuno. Immunother*., 37:343-349.

Pertl et al., (2003), "Immunotherapy with a Posttranscriptionally Modified DNA Vaccine Induces Complete Protection Against Metastatic Neuroblastoma," *Blood*, 101(2):649-654.

Reisfeld et al., (1994), "Potential of Genetically Engineered Anti-Ganglioside GD2 Antibodies for Cancer Immunotherapy," *Prog. Brain Res*., 101:201-212.

Saleh et al., (1992), "Phase I Trial of the Chimeric Anti-GD2 Monoclonal Antibody ch14.18 in Patients With Malignant Melanoma," *Hum. Antiob. Hybridomas*, 3:19-24.

Sallusto et al., (1994), "Efficient Presentation of Soluble Antigen by Cultured Human Dendritic Cells Is Maintained by Granulocyte/Macrophage Colony-stimulating Factor Plus Interleukin 4 and Downregulated by Tumor Necrosis Factor α," *J. Exp. Med*., 179:1109-1118.

Schlom (1991), "Monoclonal Antibodies: They're More and Less Than You Think," in *Molecular Foundations of Oncology*, pp. 95-133.

Weber et al., (2001), "Phase I Trial of huKS-IL2 Immunoctyokine in Patients with Prostate Carcinoma: Clinical, PK, and Biological PD Results (Abstract)," *American Society of Clinical Oncology Program/Proceedings*, 20(Part 1):259a.

Wen et al., (1994), "Erythropoietin Structure-Function Relationships: Identification of Functionally Important Domains," *J. Biological Chemistry*, 269(36):22839-22846.

Anderson et al., (1994), "Effects of Route and Formulation on Clinical Pharmacokinetics of Interleukin-2," Clin. Pharmacokinet., 27(1):19-31.

Barbulescu et al., (1998), "IL-12 and IL-18 Differentially Regulate the Transcriptional Activity of the Human IFN-γ Promoter in Primary CD4+ T Lymphocytes," *J. Immunol*., 160:3642-7.

Benacerraf et al., (1959), "The Clearance of Antigen Antibody Complexes from the Blood by the Reticulo-Endothelial System," *J. Immunol*., 82:131-7.

Boulianne et al., (1984), "Production of Functional Chimaeric Mouse/Human Antibody," *Nature*, 312:643-6.

Bubenik et al., (1995), "Interleukin-2 Gene Therapy of Residual EL-4 Leukaemia Potentiates the Effect of Cyclophosphamide Pretreatment," *J. Cancer Res. Clin. Oncol*., 121:39-43.

Chan et al., (1992), "Mechanisms of IFN-γ Induction by Natural Killer Cell Stimulatory Factor (NKSF/IL-12). Role of Transcription and mRNA Stability in the Synergistic Interaction Between NKSF and IL-2," *J. Immunol*., 148:92-98.

Cohen et al., (1998), "An Artificial Cell-Cycle Inhibitor Isolated from a Combinatorial Library," *Proc. Natl. Acad. Sci. USA*, 95:14272-7.

Connor et al., (2004), "Ex vivo Evaluation of Anti-EpCAM Immunocytokine huKS-IL2 in Ovarian Cancer," *J. Immunotherapy*, 27:211-219.

Desai et al., (1992), "IL-12 Receptor. II. Distribution and Regulation of Receptor Expression," *J. Immunol*., 148:3125-32.

Farner et al., (1995), "Distinction Between $\gamma_c$ C Detection and Function in YT Lymphoid Cells and in the Granuloctye-Macrophage Colony-Stimulating Factor-Responsive Human Myeloid Cell Line, TF-1," *Blood*, 86:4568-78.

Gurewich et al., (1988), "Characterization of the Intrinsic Fibrinolytic Properties of Pro-Urokinase Through a Study of Plasmin-Resistant Mutant Forms Produced by Site-Specific Mutagenesis of Lysine," *J. Clin. Invest*., 82:1956-1962.

Hashimoto et al., (1999), "Differential Antitumor Effects of Administration of Recombinant IL-18 or Recombinant IL-12 are Mediated Primarily by Fas-Fas Ligand- and Perforin-Induced Tumor Apoptosis, Respectively," *J. Immunol*., 163:583-9.

Hori et al., (1987), "Establishment of an Interleukin 2-Dependent Human T Cell Line from a Patient with T Cell Chronic Lymphocytic Leukemia Who is Not Infected with Human T Cell Leukemia/Lymphoma Virus," *Blood*, 70:1069-72.

Karpusas et al., (1997), "The Crystal Structure of Human Interferon β at 2.2-A Resolution," Proc. Natl. Acad. Sci. USA, 94:11813-11818.
Kelner et al., (1994), "Lymphotactin: A Cytokine that Represents a New Class of Chemokine," *Science*, 266:1395-9.
Kirkman et al., (1989), "Prolongation of Cardiac Allograft Survival in Murine Recipients Treated with a Diphtheria Toxin-Related Interleukin-2 Fusion Protein," *Transplantation*, 47(2):327-330.
Lawn et al., (1981), "DNA Sequence of a Major Human Leukocyte Interferon Gene," *Proc. Natl. Acad. Sci. USA*, 78:5435-9.
Lode et al., (1998), "Gene Therapy with a Single Chain Interleukin 12 Fusion Protein Induces T Cell-Dependent Protective Immunity in a Syngeneic Model of Murine Neuroblastoma," *Proc. Natl. Acad. Sci. USA*, 95:2475-80.
Lotze et al., (1996), "Cytokine Gene Therapy of Cancer Using Interleukin-12: Murine and Clinical Trials," *Ann. NY Acad. Sci.*, 795:440-54.
MacLean et al., (1996), "Enhancing the Effect of Theratope STn-KLH Cancer Vaccine in Patients with Metastatic Breast Cancer by Pretreatment with Low-Dose Intravenous Cyclophosphamide," J. Immunother., 19(4):309-316.
Maghazachi et al., (1997), "Interferon-Inducible Protein-10 and Lymphotactin Induce the Chemotaxis and Mobilization of Intracellular Calcium in Natural Killer Cells through Pertussis Toxin-Sensitive and -Insensitive Heterotrimeric G-Proteins," *FASEB J.*, 11:765-74.
McMahan et al., (1991), "A Novel IL-1 Receptor, Cloned From B-Cells by Mammalian Expression is Expressed in Many Cell Types," *EMBO J.*, 10:2821-32.
Mehrotra et al., (1993), "Effects of IL-12 on the Generation of Cytotoxic Activity in Human CD8+ T Lymphocytes," *J. Immunol.*, 151:2444-52.
Miyake et al., (1988), "Synthesis of Recombinant Human Single-Chain Urokinase-Type Plasminogen Activator Variants Resistant to Plasmin and Thrombin," *J. Biochem.*, 104:643-647.
Nastala et al., (1994), "Recombinant IL-12 Administration Induces Tumor Regression in Association with IFN-γ Production," *J. Immunol.*, 153:1697-706.
Nelles et al., (1987), "Characterization of Recombinant Human Single Chain Urokinase-Type Plaminogen Activtor Mutants Produced by Site-Specific Mutagenesis of Lysine 158," *J. Biol. Chem.*, 262(12):5682-5689.
Palucka et al., (1998), "Dendritic Cells as the Terminal Stage of Monocyte Differentiation," *J. Immunol.*, 160:4587-95.
Perussia et al., (1992), "Natural Killer (NK) Cell Stimulatory Factor or IL-12 Has Differential Effects on the Proliferation of TCR-αβ+, TCR-γδ+ T Lymphocytes, and NK Cells," *J. Immunol.*, 149:3495-502.
Radhakrishnan et al., (1996), "Zinc Mediated Dimer of Human Interferon-$\alpha_{2b}$ Revealed by X-Ray Crystallography," *Structure* 4(12):1453-63.
Robinson et al., (1998), "Optimizing the Stability of Single-Chain Proteins by Linker Length and Composition Mutagenesis," *Proc. Natl. Acad. Sci. USA*, 95:5929-34.
Runkel et al., (1998), "Structural and Functional Differences Between Glycosylated and Non-Glycosylated Forms of Human Interferon-β (IFN-β)," *Pharmaceutical Res.*, 15:641-649.
Sharp et al., (1988), "Codon Usage Patterns in *Escherichia coli, Bacillus subtilis, Saccharomyces cerevisiae, Schizosaccharomyces pombe, Drosophila melanogaster* and *Homo sapiens*; a Review of the Considerable Within-Species Diversity," *Nucleic Acids Res.*, 16(17):8207-8211.
Taniguchi et al., (1980), "Expression of the Human Fibroblast Interferon Gene in *Escherichia coli*," *Proc. Natl. Acad. Sci. USA*, 77:5230-5233.
Thurner, (1999), "Generation of Large Numbers of Fully Mature and Stable Dendritic Cells from Leukapheresis Products for Clinical Application," *J. Immunol. Methods*, 223:1-15.
Tiruppathi et al., (1996), "Isolation and Characterization of a Cell Surface Albumin-Binding Protein from Vascular Endothelial Cells," *Proc. Nat. Acad. Sci. USA*, 93:250-4.
Voest et al., (1995), "Inhibition of Angiogenesis in Vivo by Interleukin 12," *J. Natl. Canc. Inst.*, 87:581-6.
Weitkamp et al., (1973), "Additional Data on the Population Distribution of Human Serum Albumin Genes; Three New Variants," *Ann. Hum. Genet.*, 37:219-26.
Wysocka et al., (1995), "Interleukin-12 is Required for Interferon-γ Production and Lethality in Lipopolysaccharide-Induced Shock in Mice," *Eur. J. Immunol.*, 25:672-6.
Yeh et al., (1992), "Design of Yeast-Secreted Albumin Derivatives for Human Therapy: Biological and Antiviral Properties of a Serum Albumin-CD4 Genetic Conjugate," *Proc. Natl. Acad. Sci. USA*, 89:1904-8.

SEQUENCE LISTING

<160> NUMBER OF SEQ ID NOS: 32

<210> SEQ ID NO 1
<211> LENGTH: 582
<212> TYPE: DNA
<213> ORGANISM: Mus musculus
<220> FEATURE:
<223> OTHER INFORMATION: Description of Artificial Sequence: murine p35 coding sequence for mature protein

<400> SEQUENCE: 1
agggtcattc cagtctctgg acctgccagg tgtcttagcc agtcccgaaa cctgctgaag 60
accacagatg acatggtgaa gacggccaga gaaaaactga aacattattc ctgcactgct 120
gaagacatcg atcatgaaga catcacacgg gaccaaacca gcacattgaa gacctgttta 180
ccactggaac tacacaagaa cgagagttgc ctggctacta gagagacttc ttccacaaca 240
agagggagct gcctgccccc acagaagacg tctttgatga tgaccctgtg ccttggtagc 300
atctatgagg acttgaagat gtaccagaca gagttccagg ccatcaacgc agcacttcag 360
aatcacaacc atcagcagat cattctagac aagggcatgc tggtggccat cgatgagctg 420
atgcagtctc tgaatcataa tggcgagact ctgcgccaga aacctcctgt gggagaagca 480
gacccttaca gagtgaaaat gaagctctgc atcctgcttc acgccttcag cacccgcgtc 540
gtgaccatca acagggtgat gggctatctg agctccgcct ga 582

<210> SEQ ID NO 2
<211> LENGTH: 1472
<212> TYPE: DNA
<213> ORGANISM: Artificial Sequence
<220> FEATURE:
<223> OTHER INFORMATION: Description of Artificial Sequence: murine p40-IL-2 fusion protein coding sequence

<400> SEQUENCE: 2
atgtgtcctc agaagctaac atgtgtcctc agaagctaac catctcctgg tttgccatcg 60

```
ttttgctggt gtctccactc atggccatgt gggagctgga gaaagacgtt tatgttgtag    120

aggtggactg gactcccgat gcccctggag aaacagtgaa cctcacctgt gacacgcctg    180

aagaagatga catcacctgg acctcagacc agagacatgg agtcataggc tctggaaaga    240

ccctgaccat cactgtcaaa gagtttctag atgctggcca gtacacctgc cacaaaggag    300

gcgagactct gagccactca catctgctgc tccacaagaa ggaaaatgga atttggtcca    360

ctgaaatttt aaaaaatttc aaaaacaaga ctttcctgaa gtgtgaagca ccaaattact    420

ccggacggtt cacgtgctca tggctggtgc aaagaaacat ggacttgaag ttcaacatca    480

agagcagtag cagttcccct gactctcggg cagtgacatg tggaatggcg tctctgtctg    540

cagagaaggt cacactggac caaagggact atgagaagta ttcagtgtcc tgccaggagg    600

atgtcacctg cccaactgcc gaggagaccc tgcccattga actggcgttg gaagcacggc    660

agcagaataa atatgagaac tacagcacca gcttcttcat cagggacatc atcaaaccag    720

acccgcccaa gaacttgcag atgaagcctt tgaagaactc acaggtggag gtcagctggg    780

agtaccctga ctcctggagc actccccatt cctacttctc cctcaagttc tttgttcgaa    840

tccagcgcaa gaaagaaaag atgaaggaga cagaggaggg gtgtaaccag aaaggtgcgt    900

tcctcgtaga gaagacatct accgaagtcc aatgcaaagg cgggaatgtc tgcgtgcaag    960

ctcaggatcg ctattacaat tcctcatgca gcaagtgggc atgtgttccc tgcagggtcc   1020

gatccccggg taaagcaccc acttcaagct ctacagcgga agcacagcag cagcagcagc   1080

agcagcagca gcagcagcag cacctggagc agctgttgat ggacctacag gagctcctga   1140

gcaggatgga gaattacagg aacctgaaac tccccaggat gctcaccttc aaattttact   1200

tgcccaagca ggccacagaa ttgaaagatc ttcagtgcct agaagatgaa cttggacctc   1260

tgcggcatgt tctggatttg actcaaagca aaagctttca attggaagat gctgagaatt   1320

tcatcagcaa tatcagagta actgttgtaa aactaaaggg ctctgacaac acatttgagt   1380

gccaattcga tgatgagtca gcaactgtgg tggactttct gaggagatgg atagccttct   1440

gtcaaagcat catctcaaca agccctcaat aa                                  1472
```

```
<210> SEQ ID NO 3
<211> LENGTH: 1409
<212> TYPE: DNA
<213> ORGANISM: Artificial Sequence
<220> FEATURE:
<223> OTHER INFORMATION: Description of Artificial Sequence: murine
      p40-GM-CSF fusion protein coding sequence

<400> SEQUENCE: 3
```

```
atgtgtcctc agaagctaac atgtgtcctc agaagctaac catctcctgg tttgccatcg     60

ttttgctggt gtctccactc atggccatgt gggagctgga gaaagacgtt tatgttgtag    120

aggtggactg gactcccgat gcccctggag aaacagtgaa cctcacctgt gacacgcctg    180

aagaagatga catcacctgg acctcagacc agagacatgg agtcataggc tctggaaaga    240

ccctgaccat cactgtcaaa gagtttctag atgctggcca gtacacctgc cacaaaggag    300

gcgagactct gagccactca catctgctgc tccacaagaa ggaaaatgga atttggtcca    360

ctgaaatttt aaaaaatttc aaaaacaaga ctttcctgaa gtgtgaagca ccaaattact    420

ccggacggtt cacgtgctca tggctggtgc aaagaaacat ggacttgaag ttcaacatca    480

agagcagtag cagttcccct gactctcggg cagtgacatg tggaatggcg tctctgtctg    540

cagagaaggt cacactggac caaagggact atgagaagta ttcagtgtcc tgccaggagg    600
```

-continued

```
atgtcacctg cccaactgcc gaggagaccc tgcccattga actggcgttg gaagcacggc    660

agcagaataa atatgagaac tacagcacca gcttcttcat cagggacatc atcaaaccag    720

acccgcccaa gaacttgcag atgaagcctt tgaagaactc acaggtggag gtcagctggg    780

agtaccctga ctcctggagc actccccatt cctacttctc cctcaagttc tttgttcgaa    840

tccagcgcaa gaaagaaaag atgaaggaga cagaggaggg gtgtaaccag aaaggtgcgt    900

tcctcgtaga gaagacatct accgaagtcc aatgcaaagg cgggaatgtc tgcgtgcaag    960

ctcaggatcg ctattacaat tcctcatgca gcaagtgggc atgtgttccc tgcagggtcc   1020

gatccccggg aaaagcaccc gcccgctcac ccataattgt tacccggcct tggaagcatg   1080

tagaggccat caaagaagcc ctaaacctcc tggatgacat gcctgtcacg ttgaatgaag   1140

aggtagaagt cgtctctaac gagttctcct tcaagaagct aacatgtgtg cagacccgcc   1200

tgaagatatt cgagcagggt ctacggggca atttcaccaa actcaagggc gccttgaaca   1260

tgacagccag ctactaccag acatactgcc ccccaactcc ggaaacggac tgtgaaacac   1320

aagttaccac ctatgcggat ttcatagaca gccttaaaac ctttctgact gatatcccct   1380

ttgaatgcaa aaaaccaagc caaaaatga                                     1409
```

<210> SEQ ID NO 4
<211> LENGTH: 1389
<212> TYPE: DNA
<213> ORGANISM: Artificial Sequence
<220> FEATURE:
<223> OTHER INFORMATION: Description of Artificial Sequence: human p40-IL-2 fusion protein coding sequence

<400> SEQUENCE: 4

```
atgtgtcacc agcagttggt catctcttgg ttttccctgg tttttctggc atctcccctc     60

gtggccatat gggaactgaa gaaagatgtt tatgtcgtag aattggattg gtatccggat    120

gcccctggag aaatggtggt cctcacctgt gacacccctg aagaagatgg tatcacctgg    180

accttggacc agagcagtga ggtcttaggc tctggcaaaa ccctgaccat ccaagtcaaa    240

gagtttggag atgctggcca gtacacctgt cacaaaggag gcgaggttct aagccattcg    300

ctcctgctgc ttcacaaaaa ggaagatgga atttggtcca ctgatatttt aaaggaccag    360

aaagaaccca aaaataagac ctttctaaga tgcgaggcca agaattattc tggacgtttc    420

acctgctggt ggctgacgac aatcagtact gatttgacat tcagtgtcaa aagcagcaga    480

ggctcttctg acccccaagg ggtgacgtgc ggagctgcta cactctctgc agagagagtc    540

agaggggaca acaaggagta tgagtactca gtggagtgcc aggaggacag tgcctgccca    600

gctgctgagg agagtctgcc cattgaggtc atggtggatg ccgttcacaa gctcaagtat    660

gaaaactaca ccagcagctt cttcatcagg gacatcatca aacctgaccc acccaagaac    720

ttgcagctga agccattaaa gaattctcgg caggtggagg tcagctggga gtaccctgac    780

acctggagta ctccacattc ctacttctcc ctgacattct gcgttcaggt ccagggcaag    840

agcaagagag aaaagaaaga tagagtcttc acggacaaga cctcagccac ggtcatctgc    900

cgcaaaaatg ccagcattag cgtgcgggcc caggaccgct actatagctc atcttggagc    960

gaatgggcat ctgtgccctg cagtgcacct acttcaagtt ctacaaagaa aacacagcta   1020

caactggagc atttactgct ggatttacag atgattttga atggaattaa taattacaag   1080

aatcccaaac tcaccaggat gctcacattt aagttttaca tgcccaagaa ggccacagaa   1140

ctgaaacatc ttcagtgtct agaagaagaa ctcaaacctc tggaggaagt gctaaattta   1200
```

```
gctcaaagca aaaactttca cttaagaccc agggacttaa tcagcaatat caacgtaata   1260

gttctggaac taaagggatc tgaaacaaca ttcatgtgtg aatatgctga tgagacagca   1320

accattgtag aatttctgaa cagatggatt accttttgtc aaagcatcat ctcaacacta   1380

acttgataa                                                           1389
```

<210> SEQ ID NO 5
<211> LENGTH: 1278
<212> TYPE: DNA
<213> ORGANISM: Artificial Sequence
<220> FEATURE:
<223> OTHER INFORMATION: Description of Artificial Sequence: murine Fc-p35 fusion protein coding sequence

<400> SEQUENCE: 5

```
gagcccagag ggcccacaat caagccctgt cctccatgca aatgcccagc acctaacctc     60

ttgggtggac catccgtctt catcttccct ccaaagatca aggatgtact catgatctcc    120

ctgagcccca tagtcacatg tgtggtggtg gatgtgagcg aggatgaccc agatgtccag    180

atcagctggt ttgtgaacaa cgtggaagta cacacagctc agacacaaac ccatagagag    240

gattacaaca gtactctccg ggtggtcagt gccctcccca tccagcacca ggactggatg    300

agtggcaagg agttcaaatg caaggtcaac aacaaagacc tcccagcgcc catcgagaga    360

accatctcaa aacccaaagg gtcagtaaga gctccacagg tatatgtctt gcctccacca    420

gaagaagaga tgactaagaa acaggtcact ctgacctgca tggtcacaga cttcatgcct    480

gaagacattt acgtggagtg gaccaacaac gggaaaacag agctaaacta caagaacact    540

gaaccagtcc tggactctga tggttcttac ttcatgtaca gcaagctgag agtggaaaag    600

aagaactggg tggaaagaaa tagctactcc tgttcagtgg tccacgaggg tctgcacaat    660

caccacacga ctaagagctt ctcccggacc ccgggtaggg tcattccagt ctctggacct    720

gccaggtgtc ttagccagtc ccgaaacctg ctgaagacca cagatgacat ggtgaagacg    780

gccagagaaa aactgaaaca ttattcctgc actgctgaag acatcgatca tgaagacatc    840

acacgggacc aaaccagcac attgaagacc tgtttaccac tggaactaca caagaacgag    900

agttgcctgg ctactagaga gacttcttcc acaacaagag ggagctgcct gcccccacag    960

aagacgtctt tgatgatgac cctgtgcctt ggtagcatct atgaggactt gaagatgtac   1020

cagacagagt tccaggccat caacgcagca cttcagaatc acaaccatca gcagatcatt   1080

ctagacaagg gcatgctggt ggccatcgat gagctgatgc agtctctgaa tcataatggc   1140

gagactctgc gccagaaacc tcctgtggga gaagcagacc cttacagagt gaaaatgaag   1200

ctctgcatcc tgcttcacgc cttcagcacc cgcgtcgtga ccatcaacag ggtgatgggc   1260

tatctgagct ccgcctga                                                 1278
```

<210> SEQ ID NO 6
<211> LENGTH: 1287
<212> TYPE: DNA
<213> ORGANISM: Artificial Sequence
<220> FEATURE:
<223> OTHER INFORMATION: Description of Artificial Sequence: human Fc-p35 fusion protein coding sequence

<400> SEQUENCE: 6

```
gagcccaaat cttgtgacaa aactcacaca tgcccaccgt gcccagcacc tgaactcctg     60

gggggaccgt cagtcttcct cttcccccca aaacccaagg acaccctcat gatctcccgg    120
```

-continued

```
acccctgagg tcacatgcgt ggtggtggac gtgagccacg aagaccctga ggtcaagttc    180

aactggtacg tggacggcgt ggaggtgcat aatgccaaga caaagccgcg ggaggagcag    240

tacaacagca cgtaccgtgt ggtcagcgtc ctcaccgtcc tgcaccagga ctggctgaat    300

ggcaaggagt acaagtgcaa ggtctccaac aaagccctcc cagcccccat cgagaaaacc    360

atctccaaag ccaaagggca gccccgagaa ccacaggtgt acaccctgcc cccatcacgg    420

gaggagatga ccaagaacca ggtcagcctg acctgcctgg tcaaaggctt ctatcccagc    480

gacatcgccg tggagtggga gagcaatggg cagccggaga acaactacaa gaccacgcct    540

cccgtgctgg actccgacgg ctccttcttc ctctatagca agctcaccgt ggacaagagc    600

aggtggcagc aggggaacgt cttctcatgc tccgtgatgc atgaggctct gcacaaccac    660

tacacgcaga agagcctctc cctgtccccg ggaagaaacc tccccgtggc cactccagac    720

ccaggaatgt tcccatgcct tcaccactcc caaaacctgc tgagggccgt cagcaacatg    780

ctccagaagg ccagacaaac tctagaattt tacccttgca cttctgaaga gattgatcat    840

gaagatatca caaaagataa aaccagcaca gtggaggcct gtttaccatt ggaattaacc    900

aagaatgaga gttgcctaaa ttccagagag acctctttca taactaatgg gagttgcctg    960

gcctccagaa agacctcttt tatgatggcc ctgtgcctta gtagtattta tgaagacttg   1020

aagatgtacc aggtggagtt caagaccatg aatgcaaagc ttctgatgga tcctaagagg   1080

cagatctttc tagatcaaaa catgctggca gttattgatg agctgatgca ggccctgaat   1140

ttcaacagtg agactgtgcc acaaaaatcc tcccttgaag aaccggattt ttataaaact   1200

aaaatcaagc tctgcatact tcttcatgct ttcagaattc gggcagtgac tattgacaga   1260

gtgacgagct atctgaatgc ttcctaa                                       1287


<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence: forward
      primer for construction of murine p40-IL-2 fusion
      protein
<220> FEATURE:
<221> NAME/KEY: misc_feature
<222> LOCATION: (12)..(14)
<223> OTHER INFORMATION: translation initiation codon

<400> SEQUENCE: 7

aagctagcac catgtgtcct cagaagctaa cc                                   32


<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: reverse
      primer for construction of murine p40-IL-2 fusion
      protein
<220> FEATURE:
<221> NAME/KEY: misc_feature
<222> LOCATION: Complement((7)..(9))
<223> OTHER INFORMATION: translation stop codon

<400> SEQUENCE: 8

ctcgagctag gatcggaccc tgcaggg                                        27


<210> SEQ ID NO 9
<211> LENGTH: 31
```

<212> TYPE: DNA
<213> ORGANISM: Artificial Sequence
<220> FEATURE:
<223> OTHER INFORMATION: Description of Artificial Sequence: DNA sequence at the junction of murine p40-IL-2 fusion protein
<220> FEATURE:
<221> NAME/KEY: misc_feature
<222> LOCATION: (14)..(16)
<223> OTHER INFORMATION: encodes the C-terminal amino acid residue of murine p40
<220> FEATURE:
<221> NAME/KEY: misc_feature
<222> LOCATION: (26)..(28)
<223> OTHER INFORMATION: encodes the N-terminal amino acid residue of mature murine IL-2

<400> SEQUENCE: 9

```
ctgcagggtc cgatccccgg gtaaagcacc c                                 31
```

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence: DNA sequence at the junction of single-chain murine IL12 and GMCSF
<220> FEATURE:
<221> NAME/KEY: misc_feature
<222> LOCATION: (14)..(16)
<223> OTHER INFORMATION: encodes the C-terminal amino acid residue of murine p40
<220> FEATURE:
<221> NAME/KEY: misc_feature
<222> LOCATION: (26)..(28)
<223> OTHER INFORMATION: encodes the N-terminal amino acid residue of mature murine GMCSF

<400> SEQUENCE: 10

```
ctgcagggtc cgatccccgg gaaaagca                                     28
```

<210> SEQ ID NO 11
<211> LENGTH: 2013
<212> TYPE: DNA
<213> ORGANISM: Artificial Sequence
<220> FEATURE:
<223> OTHER INFORMATION: Description of Artificial Sequence: murine p35-linker-p40-IL-2 fusion protein coding sequence

<400> SEQUENCE: 11

```
agggtcattc cagtctctgg acctgccagg tgtcttagcc agtcccgaaa cctgctgaag     60

accacagatg acatggtgaa gacggccaga gaaaaactga aacattattc ctgcactgct    120

gaagacatcg atcatgaaga catcacacgg gaccaaacca gcacattgaa gacctgttta    180

ccactggaac tacacaagaa cgagagttgc ctggctacta gagagacttc ttccacaaca    240

agagggagct gcctgccccc acagaagacg tctttgatga tgaccctgtg ccttggtagc    300

atctatgagg acttgaagat gtaccagaca gagttccagg ccatcaacgc agcacttcag    360

aatcacaacc atcagcagat cattctagac aagggcatgc tggtggccat cgatgagctg    420

atgcagtctc tgaatcataa tggcgagact ctgcgccaga aacctcctgt gggagaagca    480

gacccttaca gagtgaaaat gaagctctgc atcctgcttc acgccttcag cacccgcgtc    540

gtgaccatca acagggtgat gggctatctg agctccgcgt cgagcggggg cagcgggggc    600

ggaggcagcg gcgggggcgg atccgccatg tgggtgctgg agaaagacgt ttatgttgta    660

gaggtggact ggactcccga tgcccctgga gaaacagtga acctcacctg tgacacgcct    720
```

-continued

```
gaagaagatg acatcacctg gacctcagac cagagacatg gagtcatagg ctctggaaag    780

accctgacca tcactgtcaa agagtttcta gatgctggcc agtacacctg ccacaaagga    840

ggcgagactc tgagccactc acatctgctg ctccacaaga aggaaaatgg aatttggtcc    900

actgaaattt taaaaaattt caaaaacaag actttcctga agtgtgaagc accaaattac    960

tccggacggt tcacgtgctc atggctggtg caaagaaaca tggacttgaa gttcaacatc   1020

aagagcagta gcagttcccc tgactctcgg gcagtgacat gtggaatggc gtctctgtct   1080

gcagagaagg tcacactgga ccaaagggac tatgagaagt attcagtgtc ctgccaggag   1140

gatgtcacct gcccaactgc cgaggagacc ctgcccattg aactggcgtt ggaagcacgg   1200

cagcagaata aatatgagaa ctacagcacc agcttcttca tcagggacat catcaaacca   1260

gacccgccca agaacttgca gatgaagcct ttgaagaact cacaggtgga ggtcagctgg   1320

gagtaccctg actcctggag cactccccat tcctacttct ccctcaagtt ctttgttcga   1380

atccagcgca agaaagaaaa gatgaaggag acagaggagg ggtgtaacca gaaaggtgcg   1440

ttcctcgtag agaagacatc taccgaagtc caatgcaaag gcgggaatgt ctgcgtgcaa   1500

gctcaggatc gctattacaa ttcctcatgc agcaagtggg catgtgttcc ctgcagggtc   1560

cgatccccgg gtaaagcacc cacttcaagc tctacagcgg aagcacagca gcagcagcag   1620

cagcagcagc agcagcagca gcacctggag cagctgttga tggacctaca ggagctcctg   1680

agcaggatgg agaattacag gaacctgaaa ctccccagga tgctcacctt caaattttac   1740

ttgcccaagc aggccacaga attgaaagat cttcagtgcc tagaagatga acttggacct   1800

ctgcggcatg ttctggattt gactcaaagc aaaagctttc aattggaaga tgctgagaat   1860

ttcatcagca atatcagagt aactgttgta aaactaaagg gctctgacaa cacatttgag   1920

tgccaattcg atgatgagtc agcaactgtg gtggactttc tgaggagatg gatagccttc   1980

tgtcaaagca tcatctcaac aagccctcaa taa                                2013
```

```
<210> SEQ ID NO 12
<211> LENGTH: 1569
<212> TYPE: DNA
<213> ORGANISM: Artificial Sequence
<220> FEATURE:
<223> OTHER INFORMATION: Description of Artificial Sequence: murine
      p35-linker-p40 fusion protein coding sequence

<400> SEQUENCE: 12

agggtcattc cagtctctgg acctgccagg tgtcttagcc agtcccgaaa cctgctgaag     60

accacagatg acatggtgaa gacggccaga gaaaaactga aacattattc ctgcactgct    120

gaagacatcg atcatgaaga catcacacgg gaccaaacca gcacattgaa gacctgttta    180

ccactggaac tacacaagaa cgagagttgc ctggctacta gagagacttc ttccacaaca    240

agagggagct gcctgccccc acagaagacg tctttgatga tgaccctgtg ccttggtagc    300

atctatgagg acttgaagat gtaccagaca gagttccagg ccatcaacgc agcacttcag    360

aatcacaacc atcagcagat cattctagac aagggcatgc tggtggccat cgatgagctg    420

atgcagtctc tgaatcataa tggcgagact ctgcgccaga aacctcctgt gggagaagca    480

gacccttaca gagtgaaaat gaagctctgc atcctgcttc acgccttcag cacccgcgtc    540

gtgaccatca acagggtgat gggctatctg agctccgcgt cgagcggggg cagcgggggc    600

ggaggcagcg gcgggggcgg atccgccatg tgggtgctgg agaaagacgt ttatgttgta    660

gaggtggact ggactcccga tgcccctgga gaaacagtga acctcacctg tgacacgcct    720
```

-continued

```
gaagaagatg acatcacctg gacctcagac cagagacatg gagtcatagg ctctggaaag    780

accctgacca tcactgtcaa agagtttcta gatgctggcc agtacacctg ccacaaagga    840

ggcgagactc tgagccactc acatctgctg ctccacaaga aggaaaatgg aatttggtcc    900

actgaaattt taaaaaattt caaaaacaag actttcctga agtgtgaagc accaaattac    960

tccggacggt tcacgtgctc atggctggtg caaagaaaca tggacttgaa gttcaacatc   1020

aagagcagta gcagttcccc tgactctcgg gcagtgacat gtggaatggc gtctctgtct   1080

gcagagaagg tcacactgga ccaaagggac tatgagaagt attcagtgtc ctgccaggag   1140

gatgtcacct gcccaactgc cgaggagacc ctgcccattg aactggcgtt ggaagcacgg   1200

cagcagaata aatatgagaa ctacagcacc agcttcttca tcagggacat catcaaacca   1260

gacccgccca agaacttgca gatgaagcct ttgaagaact cacaggtgga ggtcagctgg   1320

gagtaccctg actcctggag cactccccat tcctacttct ccctcaagtt ctttgttcga   1380

atccagcgca agaaagaaaa gatgaaggag acagaggagg ggtgtaacca gaaaggtgcg   1440

ttcctcgtag agaagacatc taccgaagtc caatgcaaag gcgggaatgt ctgcgtgcaa   1500

gctcaggatc gctattacaa ttcctcatgc agcaagtggg catgtgttcc ctgcagggtc   1560

cgatcctag                                                           1569


<210> SEQ ID NO 13
<211> LENGTH: 2709
<212> TYPE: DNA
<213> ORGANISM: Artificial Sequence
<220> FEATURE:
<223> OTHER INFORMATION: Description of Artificial Sequence: murine
      Fc-p35-linker-p40-IL-2 fusion protein coding
      sequence

<400> SEQUENCE: 13

gagcccagag ggcccacaat caagccctgt cctccatgca aatgcccagc acctaacctc     60

ttgggtggac catccgtctt catcttccct ccaaagatca aggatgtact catgatctcc    120

ctgagcccca tagtcacatg tgtggtggtg gatgtgagcg aggatgaccc agatgtccag    180

atcagctggt ttgtgaacaa cgtggaagta cacacagctc agacacaaac ccatagagag    240

gattacaaca gtactctccg ggtggtcagt gccctcccca tccagcacca ggactggatg    300

agtggcaagg agttcaaatg caaggtcaac aacaaagacc tcccagcgcc catcgagaga    360

accatctcaa aacccaaagg gtcagtaaga gctccacagg tatatgtctt gcctccacca    420

gaagaagaga tgactaagaa acaggtcact ctgacctgca tggtcacaga cttcatgcct    480

gaagacattt acgtggagtg gaccaacaac gggaaaacag agctaaacta caagaacact    540

gaaccagtcc tggactctga tggttcttac ttcatgtaca gcaagctgag agtggaaaag    600

aagaactggg tggaaagaaa tagctactcc tgttcagtgg tccacgaggg tctgcacaat    660

caccacacga ctaagagctt ctcccggacc ccgggtaggg tcattccagt ctctggacct    720

gccaggtgtc ttagccagtc ccgaaacctg ctgaagacca cagatgacat ggtgaagacg    780

gccagagaaa aactgaaaca ttattcctgc actgctgaag acatcgatca tgaagacatc    840

acacgggacc aaaccagcac attgaagacc tgtttaccac tggaactaca caagaacgag    900

agttgcctgg ctactagaga gacttcttcc acaacaagag ggagctgcct gcccccacag    960

aagacgtctt tgatgatgac cctgtgcctt ggtagcatct atgaggactt gaagatgtac   1020

cagacagagt tccaggccat caacgcagca cttcagaatc acaaccatca gcagatcatt   1080

ctagacaagg gcatgctggt ggccatcgat gagctgatgc agtctctgaa tcataatggc   1140
```

gagactctgc gccagaaacc tcctgtggga gaagcagacc cttacagagt gaaaatgaag 1200
ctctgcatcc tgcttcacgc cttcagcacc cgcgtcgtga ccatcaacag ggtgatgggc 1260
tatctgagct ccgcgtcgag cgggggcagc gggggcggag gcagcggcgg gggcggatcc 1320
gccatgtggg tgctggagaa agacgtttat gttgtagagg tggactggac tcccgatgcc 1380
cctggagaaa cagtgaacct cacctgtgac acgcctgaag aagatgacat cacctggacc 1440
tcagaccaga gacatggagt cataggctct ggaaagaccc tgaccatcac tgtcaaagag 1500
tttctagatg ctggccagta cacctgccac aaaggaggcg agactctgag ccactcacat 1560
ctgctgctcc acaagaagga aaatggaatt tggtccactg aaattttaaa aaatttcaaa 1620
aacaagactt tcctgaagtg tgaagcacca aattactccg gacggttcac gtgctcatgg 1680
ctggtgcaaa gaaacatgga cttgaagttc aacatcaaga gcagtagcag ttcccctgac 1740
tctcgggcag tgacatgtgg aatggcgtct ctgtctgcag agaaggtcac actggaccaa 1800
agggactatg agaagtattc agtgtcctgc caggaggatg tcacctgccc aactgccgag 1860
gagaccctgc ccattgaact ggcgttggaa gcacggcagc agaataaata tgagaactac 1920
agcaccagct tcttcatcag ggacatcatc aaaccagacc cgcccaagaa cttgcagatg 1980
aagcctttga agaactcaca ggtggaggtc agctgggagt accctgactc ctggagcact 2040
ccccattcct acttctccct caagttcttt gttcgaatcc agcgcaagaa agaaaagatg 2100
aaggagacag aggaggggtg taaccagaaa ggtgcgttcc tcgtagagaa gacatctacc 2160
gaagtccaat gcaaaggcgg gaatgtctgc gtgcaagctc aggatcgcta ttacaattcc 2220
tcatgcagca agtgggcatg tgttccctgc agggtccgat ccccgggtaa agcacccact 2280
tcaagctcta cagcggaagc acagcagcag cagcagcagc agcagcagca gcagcagcac 2340
ctggagcagc tgttgatgga cctacaggag ctcctgagca ggatggagaa ttacaggaac 2400
ctgaaactcc ccaggatgct caccttcaaa ttttacttgc ccaagcaggc cacagaattg 2460
aaagatcttc agtgcctaga agatgaactt ggacctctgc ggcatgttct ggatttgact 2520
caaagcaaaa gctttcaatt ggaagatgct gagaatttca tcagcaatat cagagtaact 2580
gttgtaaaac taaagggctc tgacaacaca tttgagtgcc aattcgatga tgagtcagca 2640
actgtggtgg actttctgag gagatggata gccttctgtc aaagcatcat ctcaacaagc 2700
cctcaataa 2709

<210> SEQ ID NO 14
<211> LENGTH: 33
<212> TYPE: DNA
<213> ORGANISM: Artificial Sequence
<220> FEATURE:
<223> OTHER INFORMATION: Description of Artificial Sequence: forward primer for PCR amplification of murine p35 subunit of IL-12
<220> FEATURE:
<221> NAME/KEY: misc_feature
<222> LOCATION: (16)..(18)
<223> OTHER INFORMATION: translation initiation codon

<400> SEQUENCE: 14
aagcttgcta gcagcatgtg tcaatcacgc tac 33

<210> SEQ ID NO 15
<211> LENGTH: 30
<212> TYPE: DNA
<213> ORGANISM: Artificial Sequence
<220> FEATURE:

-continued

```
<223> OTHER INFORMATION: Description of Artificial Sequence: reverse
      primer for PCR amplification of murine p35 subunit of
      IL-12
<220> FEATURE:
<221> NAME/KEY: misc_feature
<222> LOCATION: Complement((10)..(12))
<223> OTHER INFORMATION: translation stop codon

<400> SEQUENCE: 15

ctcgagcttt caggcggagc tcagatagcc                                      30


<210> SEQ ID NO 16
<211> LENGTH: 61
<212> TYPE: DNA
<213> ORGANISM: Artificial Sequence
<220> FEATURE:
<223> OTHER INFORMATION: Description of Artificial Sequence: coding
      sequence at the junction between p35 and p40 that
      comprise the murine single-chain IL-12
<220> FEATURE:
<221> NAME/KEY: misc_feature
<222> LOCATION: (8)..(10)
<223> OTHER INFORMATION: encodes the C-terminal amino acid residue of
      murine p35
<220> FEATURE:
<221> NAME/KEY: misc_feature
<222> LOCATION: (59)..(61)
<223> OTHER INFORMATION: encodes the N-terminal amino acid residue of
      mature murine p40

<400> SEQUENCE: 16

gagctccgcg tcgagcgggg gcagcggggg cggaggcagc ggcgggggcg gatccgccat     60

g                                                                     61


<210> SEQ ID NO 17
<211> LENGTH: 16
<212> TYPE: PRT
<213> ORGANISM: Artificial Sequence
<220> FEATURE:
<223> OTHER INFORMATION: Description of Artificial Sequence: Protein
      sequence at the junction between p35 and p40 that
      comprise the murine single-chain IL-12

<400> SEQUENCE: 17

Ser Ser Gly Gly Ser Gly Gly Gly Gly Ser Gly Gly Gly Gly Ser Ala
  1               5                  10                  15


<210> SEQ ID NO 18
<211> LENGTH: 73
<212> TYPE: DNA
<213> ORGANISM: Artificial Sequence
<220> FEATURE:
<223> OTHER INFORMATION: Description of Artificial Sequence: coding
      sequence at the junction between murine p40 and
      the mature N-terminus of KS heavy chain
<220> FEATURE:
<221> NAME/KEY: misc_feature
<222> LOCATION: (14)..(16)
<223> OTHER INFORMATION: encodes the C-terminal amino acid residue of
      murine p40
<220> FEATURE:
<221> NAME/KEY: misc_feature
<222> LOCATION: (71)..(73)
<223> OTHER INFORMATION: encodes the N-terminal residue of mature KS
      heavy chain

<400> SEQUENCE: 18

ctgcagggtc cgatccccgg gatccggagg ttcagggggc ggaggtagcg gcggaggggg     60

ctccttaagc cag                                                        73
```

<210> SEQ ID NO 19
<211> LENGTH: 18
<212> TYPE: PRT
<213> ORGANISM: Artificial Sequence
<220> FEATURE:
<223> OTHER INFORMATION: Description of Artificial Sequence: protein sequence at the junction between murine p40 and the mature N-terminus of KS heavy chain

<400> SEQUENCE: 19

```
Pro Gly Ser Gly Gly Ser Gly Gly Gly Gly Ser Gly Gly Gly Gly Ser
  1               5                  10                  15

Leu Ser
```

<210> SEQ ID NO 20
<211> LENGTH: 64
<212> TYPE: DNA
<213> ORGANISM: Artificial Sequence
<220> FEATURE:
<223> OTHER INFORMATION: Description of Artificial Sequence: coding sequence at the junction between murine p35 and the KS light chain
<220> FEATURE:
<221> NAME/KEY: misc_feature
<222> LOCATION: (8)..(10)
<223> OTHER INFORMATION: encodes the C-terminal amino acid residue of murine p35
<220> FEATURE:
<221> NAME/KEY: misc_feature
<222> LOCATION: (62)..(64)
<223> OTHER INFORMATION: encodes the N-terminal amino acid residue of the light chain

<400> SEQUENCE: 20

```
gagctccgcg tcgagcgggg gcagcggggg cggaggcagc ggcgggggcg gatccttaag     60

cgag                                                                  64
```

<210> SEQ ID NO 21
<211> LENGTH: 17
<212> TYPE: PRT
<213> ORGANISM: Artificial Sequence
<220> FEATURE:
<223> OTHER INFORMATION: Description of Artificial Sequence: protein sequence at the junction between murine p35 and the KS light chain

<400> SEQUENCE: 21

```
Ser Ser Gly Gly Ser Gly Gly Gly Gly Ser Gly Gly Gly Gly Ser Leu
  1               5                  10                  15

Ser
```

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence: forward primer for the PCR amplification of murine IL-4
<220> FEATURE:
<221> NAME/KEY: misc_feature
<222> LOCATION: (9)..(11)
<223> OTHER INFORMATION: translation initiation codon

<400> SEQUENCE: 22

```
tctagaccat gggtctcaac ccccagc                                         27
```

<210> SEQ ID NO 23

```
<211> LENGTH: 47
<212> TYPE: DNA
<213> ORGANISM: Artificial Sequence
<220> FEATURE:
<223> OTHER INFORMATION: Description of Artificial Sequence: reverse
      primer for the PCR amplification of murine IL-4
<220> FEATURE:
<221> NAME/KEY: misc_feature
<222> LOCATION: Complement((8)..(10))
<223> OTHER INFORMATION: encodes the C-terminal amino acid residue of
      murine IL-4

<400> SEQUENCE: 23

cggatcccga gtaatccatt tgcatgatgc tctttaggct ttccagg                47


<210> SEQ ID NO 24
<211> LENGTH: 57
<212> TYPE: DNA
<213> ORGANISM: Artificial Sequence
<220> FEATURE:
<223> OTHER INFORMATION: Description of Artificial Sequence: coding
      sequence at the junction of murine IL-4 and the
      mature KS-1/4 light chain
<220> FEATURE:
<221> NAME/KEY: misc_feature
<222> LOCATION: (1)..(3)
<223> OTHER INFORMATION: encodes the C-terminal serine residue of murine
      IL-4
<220> FEATURE:
<221> NAME/KEY: misc_feature
<222> LOCATION: (55)..(57)
<223> OTHER INFORMATION: encodes the N-terminal amino acid residue of
      the mature KS-1/4 light chain

<400> SEQUENCE: 24

tcgggatccg gaggttcagg gggcggaggt agcggcggag ggggctcctt aagcgag     57


<210> SEQ ID NO 25
<211> LENGTH: 19
<212> TYPE: PRT
<213> ORGANISM: Artificial Sequence
<220> FEATURE:
<223> OTHER INFORMATION: Description of Artificial Sequence: protein
      sequence at the junction of murine IL-4 and the
      mature KS-1/4 light chain

<400> SEQUENCE: 25

Ser Gly Ser Gly Gly Ser Gly Gly Gly Gly Ser Gly Gly Gly Gly Ser
  1               5                  10                  15

Leu Ser Glu


<210> SEQ ID NO 26
<211> LENGTH: 27
<212> TYPE: DNA
<213> ORGANISM: Artificial Sequence
<220> FEATURE:
<223> OTHER INFORMATION: Description of Artificial Sequence: forward
      primer for the PCR amplification of murine IL-4
<220> FEATURE:
<221> NAME/KEY: misc_feature
<222> LOCATION: (9)..(11)
<223> OTHER INFORMATION: translation initiation codon

<400> SEQUENCE: 26

tctagaccat gggtctcaac ccccagc                                      27


<210> SEQ ID NO 27
<211> LENGTH: 52
<212> TYPE: DNA
<213> ORGANISM: Artificial Sequence
```

<220> FEATURE:
<223> OTHER INFORMATION: Description of Artificial Sequence: reverse primer for the PCR amplification of murine IL-4
<220> FEATURE:
<221> NAME/KEY: misc_feature
<222> LOCATION: Complement((13)..(15))
<223> OTHER INFORMATION: encodes the C-terminal amino acid residue of murine IL-4

<400> SEQUENCE: 27
cgatatcccg gacgagtaat ccatttgcat gatgctcttt aggctttcca gg 52

<210> SEQ ID NO 28
<211> LENGTH: 39
<212> TYPE: DNA
<213> ORGANISM: Artificial Sequence
<220> FEATURE:
<223> OTHER INFORMATION: Description of Artificial Sequence: coding sequence at the junction between murine IL-4 and murine GM-CSF
<220> FEATURE:
<221> NAME/KEY: misc_feature
<222> LOCATION: (1)..(12)
<223> OTHER INFORMATION: encodes the C-terminal sequence of muIL4
<220> FEATURE:
<221> NAME/KEY: misc_feature
<222> LOCATION: (28)..(39)
<223> OTHER INFORMATION: encodes the N-terminal sequence of muGM-CSF

<400> SEQUENCE: 28
atggattact cgtccgggat gggaaaagca cccgcccgc 39

<210> SEQ ID NO 29
<211> LENGTH: 32
<212> TYPE: DNA
<213> ORGANISM: Artificial Sequence
<220> FEATURE:
<223> OTHER INFORMATION: Description of Artificial Sequence: forward primer for the PCR amplification of murine lymphotactin
<220> FEATURE:
<221> NAME/KEY: misc_feature
<222> LOCATION: (13)..(15)
<223> OTHER INFORMATION: translation initiation codon

<400> SEQUENCE: 29
tctagagcca ccatgagact tctcctcctg ac 32

<210> SEQ ID NO 30
<211> LENGTH: 26
<212> TYPE: DNA
<213> ORGANISM: Artificial Sequence
<220> FEATURE:
<223> OTHER INFORMATION: Description of Artificial Sequence: reverse primer for the PCR amplification of murine lymphotactin
<220> FEATURE:
<221> NAME/KEY: misc_feature
<222> LOCATION: Complement((7)..(9))
<223> OTHER INFORMATION: encodes the C-terminal amino acid residue of murine lymphotactin

<400> SEQUENCE: 30
ggatccccca gtcagggtta ctgctg 26

<210> SEQ ID NO 31
<211> LENGTH: 57
<212> TYPE: DNA
<213> ORGANISM: Artificial Sequence
<220> FEATURE:
<223> OTHER INFORMATION: Description of Artificial Sequence: coding sequence at the junction between murine lymphotactin and KS-IL2 heavy chain -continued

```
<220> FEATURE:
<221> NAME/KEY: misc_feature
<222> LOCATION: (1)..(3)
<223> OTHER INFORMATION: encodes the C-terminal amino acid residue of
      murine lymphotactin
<220> FEATURE:
<221> NAME/KEY: misc_feature
<222> LOCATION: (55)..(57)
<223> OTHER INFORMATION: encodes the N-terminal amino acid residue of
      the KS-IL2 heavy chain

<400> SEQUENCE: 31

cccggatccg gaggttcagg gggcggaggt agcggcggag ggggctcctt aagccag        57


<210> SEQ ID NO 32
<211> LENGTH: 17
<212> TYPE: PRT
<213> ORGANISM: Artificial Sequence
<220> FEATURE:
<223> OTHER INFORMATION: Description of Artificial Sequence: protein
      sequence at the junction between murine
      lymphotactin and KS-IL2 heavy chain

<400> SEQUENCE: 32

Gly Ser Gly Gly Ser Gly Gly Gly Gly Ser Gly Gly Gly Gly Ser Leu
  1               5                  10                  15

Ser
```

METHODS OF TARGETING MULTIPLE CYTOKINES

REFERENCE TO RELATED APPLICATIONS

This application is a continuation of U.S. application Ser. No. 10/603,064, filed Jun. 24, 2003, now U.S. Pat. No. 7,141, 651 which is a continuation of U.S. application Ser. No. 09/634,368, filed Aug. 9, 2000, now U.S. Pat. No. 6,617,135, which claims the benefit of U.S. Application No. 60/147,924, filed Aug. 9, 1999, the disclosures of which are hereby incorporated by reference herein in their entireties for all purposes.

FIELD OF THE INVENTION

The present invention relates to methods for the construction and expression of multiple cytokine protein complexes and their compositions. More specifically, the invention relates to fusion proteins composed of multiple cytokines and a targeting component, and methods of using the same for the treatment of diseases such as cancer and viral infection.

BACKGROUND OF THE INVENTION

The regulatory networks controlling the immune system rely on secreted protein signaling molecules termed cytokines to turn on and off the functions of immune cells as well regulate their proliferation. These responses generally involve multiple cytokines that act in concert to achieve the desired biological effect. Certain cytokines such as interleukin-2 (IL-2) can induce immune cell proliferation by themselves and can activate other functions including secondary cytokine secretion. Another cytokine, interleukin-12 (IL-12) [reviewed by Trinchieri, 1994, Blood 84:4008-4027], can induce proliferation of certain immune cells and induce another key immune modulator, interferon-γ (IFN-γ). This induction of IFN-γ is a key activity of IL-12, although IL-12 has other important activities that are IFN-γ independent. Since IL-12 itself is induced at an early stage in infectious disease situations, it is thought to link the innate and acquired immune systems.

Many in vitro studies with both mouse and human immune cells have shown the importance of cytokine combinations in the development of optimal immune responses. For example, most T cells do not express IL-12 receptors (IL-12R) until they have been activated with mitogens or cultured in high concentrations of IL-2 [Desai et al. (1992), J. Immunol. 148: 3125-3132]. Once the receptors are expressed, the cells become far more responsive to IL-12. Furthermore, IL-12 induces IFN-γ transcription, but IFN-γ mRNA is degraded shortly thereafter. In the presence of IL-2, the mRNA is stabilized, resulting in a dramatic increase in the amount of IFN-γ produced [Chan et al. (1992) J. Immunol. 148:92-98]. In other studies, it was found that the cytokine combinations IL-3 plus IL-11 or IL-3 plus Steel Factor had a synergistic effect with IL-12 on the proliferation of early hematopoietic progenitor cells [Trinchieri, 1994; cited above]. The combination of interleukin-4 and GM-CSF is particularly useful in stimulating dendritic cells (Palucka et al. [1998] J. Immunology 160:4587-4595). For stimulation of the cell-mediated immune response, it is also useful to combine IL-12 with IL-18, a recently discovered Th1-promoting cytokine with some activities that are complementary to IL-12 (Hashimoto et al. [1999] J. Immunology 163:583-589; Barbulescu et al. [1998] J. Immunology 160:3642-3647). In addition, IL-2 and interferon-γ are synergistic in certain circumstances [Palladino, M. A., U.S. Pat. No. 5,082,658].

In many of these synergy studies it was found that the relative level of each cytokine was very important. Whereas the addition of IL-12 in the presence of suboptimal amounts of IL-2 led to synergy in the induction of proliferation, cytolytic activity and IFN-γ induction, combinations of IL-2 and IL-12 using a high dose of one cytokine were found to be antagonistic [Perussia et al., J. Immunol. 149:3495-3502 (1992); Mehrotra et al., J. Immunol. 151:2444-2452 (1993)]. A similar situation also exists in combinations of IL-12 and IL-7.

Synergy studies between IL-12 and other cytokines for the generation of anti-tumor responses in mice have also shown mixed results. In some models synergy was seen at suboptimal doses of each cytokine and higher doses led to enhanced toxicity, while in other models, combinations of IL-12 and IL-2 showed little or no synergy [see, for example, Nastala et al., J. Immunol. 153:1697-1706. (1994)]. These results may reflect the inherent difficulty of combining two potentially synergistic agents in vivo, especially when there is the need to maintain a fixed ratio of activities of two agents with different pharmacological properties, such as different circulating half-life and biodistribution.

In in vitro cell culture experiments, it is straightforward to control cytokine levels, but many factors can affect the relative biodistribution and localization of cytokines in vivo, thus affecting their immunostimulatory capacity. The most important of these factors is the half-life. The half-life of IL-2 in the circulation after bolus injection is approximately 10 minutes. In striking contrast to these pharmacokinetic properties, the circulating half-life of IL-12 has been reported to be >3 hr in mice [Wysocka et al (1995) Eur. J. Immunol. 25:672] and from 5-10 hr in humans [Lotze et al. (1996) Ann NY Acad Sci 795:440-454].

This difference is thought to be due to the relatively small sizes of both IL-2 and GM-CSF (15-25 kD vs. 75 kD for IL-12), allowing IL-2 and GM-CSF to be cleared by renal filtration. Proteins with a molecular weight of less than about 50 kD are cleared by renal filtration. Almost all cytokines are smaller than 50 kD and undergo similar, rapid clearance by renal filtration. When treatment with two such small, rapidly cleared cytokines is desired, it is sufficient to simply co-administer the cytokines. However, co-administration is not optimal for cytokines with significantly different half-lives.

The systemic administration of cytokines is difficult due to their deleterious side effects. For example, high levels of Interferon-alpha result in significant side effects, including skin, neurologic, immune and endocrine toxicities. It is expected that multiple cytokine fusions might show particularly serious side effects.

To reduce side effects of systemic administration of cytokines, one strategy is to fuse a cytokine to a second molecule with targeting capability. Fusions in which an Fc region is placed at the N-terminus of a another protein (termed 'immunofusins' or 'Fc-X' fusions, where X is a ligand such as Interferon-alpha) have a number of distinctive, advantageous biological properties [Lo et al., U.S. Pat. Nos. 5,726,044 and 5,541,087; Lo et al., Protein Engineering 11:495]. In particular, such fusion proteins can still bind to the relevant Fc receptors on cell surfaces. However, when the ligand binds to its receptor on a cell surface, the orientation of the Fc region is altered and the sequences that mediate antibody-dependent cell-mediated cytotoxicity (ADCC) and complement fixation appear to be occluded. As a result, the Fc region in an Fc-X molecule does not mediate ADCC or complement fixation effectively. The cytotoxic effect due to the fusion of an N-terminal cytokine and a C-terminal Fc region is well known. For example, fusion of IL-2 to the N-terminus of an Fc region creates a molecule that is able to bind to cells bearing the IL-2 receptor, fix complement, and lyse the cells as a result [Landolfi, N. F. (1993) U.S. Pat. No. 5,349,053]. In contrast, Fc-IL-2 fusion proteins do not have this property. Thus, Fc-X fusions are expected to have the virtues of increased serum half-life and relative concentration in the liver, without the deleterious effects of ADCC and complement fixation.

It has been demonstrated that many different proteins with short serum half-lives can be fused to an Fc region in an Fc-X configuration, and the resulting fusions have much longer serum half-lives. However, the serum half-lives of two different Fc fusions will not generally be identical. Thus, when delivery of two different X moieties is desired, co-administration of two different Fc-X proteins will not generally be optimal.

Under some circumstances, a better approach is to target the effect of the cytokine to a cell surface antigen by fusing it to an antibody (or fragment derived therefrom) having specificity and affinity for that antigen (Gillies, U.S. Pat. No. 5,650,150; Gillies et al., Proc. Natl. Acad. Sci. 89:1428) or by linking a protein antigen and stimulatory cytokine via a peptide linkage in the form of a fusion protein (Hazama et al, Vaccine 11:629). While antibodies themselves can increase the half-life of a fused cytokine, there are still differences between different cytokine fusions with the same antibody [see, for example, Gillies et al., Bioconjugate Chem. 4:230-235 (1993); Gillies et al., J. Immunol. 160:6195-6203] that would make co-localization at a target site difficult. As discussed above, this could lead to an imbalance in cytokine activities and decrease the desired synergistic effects. In addition, the use of two different fusion proteins requires testing each fusion separately for its safety and effectiveness profile, and then further testing as mixtures.

SUMMARY OF THE INVENTION

The present invention provides complexes or fusions between two or more different cytokines, which are useful for general as well as targeted immune therapy. These complexes or fusions optionally include other protein moieties. One feature of such complexes or fusions is that they provide the activities of the component cytokines in a fixed ratio.

Generally, the invention relates to a protein complex containing at least two different cytokines. The cytokines could be in the same polypeptide chain or connected by a covalent bond such as a disulfide bond or a bond formed by chemical crosslinking. Alternatively, the cytokines could be in a stable, non-covalent association. In some preferred embodiments, the protein complex comprises a targeting moiety, such as an antibody or antibody fragment, that targets the complex to a locus in a mammal.

In a preferred embodiment, the invention provides a protein complex combining the bioactivity of a two-chain cytokine, such as IL-12, with that of a second cytokine. The cytokines may be covalently bonded (e.g. fused) to each other. The cytokines may also be associated through other moieties. For example, the polypeptide chain containing the second cytokine could include a binding moiety that specifically binds IL-12, such as an antibody to IL-12 or a receptor to IL-12. Alternatively, the binding moiety could interact with a second moiety that is associated with the IL-12. For example, if a polypeptide chain encoding a subunit of IL-12 also includes avidin, the polypeptide containing the second cytokine may include biotin as a targeting moiety. In one preferred embodiment, the second cytokine is IL-2.

The invention provides methods for the production of fusion proteins of IL-12 that maintain both IL-12 activity and that of the second cytokine, while providing a longer, single pharmacokinetic behavior, similar to that of IL-12 itself, that increases the duration of the activity of the second cytokine and maintains the balance of activities of the two cytokines after injection into an animal.

In another embodiment of the invention, the fusion proteins comprise a heterodimeric form of IL-12 in which the p35 and p40 subunits of IL-12 are linked by a disulfide bond and covalently bonded to a second cytokine at either the amino or carboxyl terminus of the p35 or p40 subunit of IL-12 with the general formula IL-12-X or X-IL-12, where X is a second cytokine.

In another embodiment of the invention, the fusion proteins comprise a second cytokine covalently bonded at either the amino or carboxyl terminus to a single-chain (sc) form of IL-12 comprising the two polypeptide subunits joined via a flexible peptide linker with the general formula scIL-12-X or X-scIL-12.

In yet another embodiment, two cytokines are further fused to a protein capable of forming a dimeric or multimeric structure, at either the amino or carboxyl terminus of said protein chain. In a preferred form of this embodiment, one of the fusion protein forms of IL-12 with a second cytokine is further fused to a portion of an immunoglobulin (Ig) chain, such as the Fc region, that is capable of dimerization. Further embodiments include fusion of at least one polypeptide chain of IL-12 at either terminus of a portion of an Ig chain and a second cytokine fused at the other terminus.

In another embodiment, two or more cytokines are fused to a protein with targeting capability by virtue of binding to a specific receptor. For example, an Fc region is capable of binding to Fc receptors, which are abundant in the liver. Fusions of an Fc region with multiple cytokines illustrate the advantages of both dimerization and targeting, but in some circumstances it is useful to construct fusions of multiple cytokines that have only multimerization or targeting capability, but not both capabilities.

In yet another embodiment, a fusion protein comprising multiple cytokines is further fused at either the amino or carboxyl terminus to a member of a class of molecules with diverse targeting capability, such as an antibody or a peptide aptamer with or without a scaffold (Colas et al. [1998] Proc Natl Acad Sci USA. 95:14272-7). A particular embodiment is the fusion of multiple cytokines to at least a portion of an antibody capable of binding an antigen, such as an intact antibody, a single-chain antibody, or a single-chain Fv region. Further embodiments include fusions of at least one polypeptide chain of IL-12 at either terminus of at least a portion of an antibody chain that is capable of binding an antigen, and a second cytokine fused at the other terminus.

According to the above descriptions, it is generally preferred to construct multiple cytokine fusion proteins and multiple cytokine-antibody fusion proteins by genetic engineering techniques, such that the component proteins are linked by covalent bonds such as amide bonds or disulfide bonds. However, it is also useful to use chemical cross-linkers to construct such protein complexes. Such methods are well established in the art of protein chemistry. Alternatively, it is sometimes sufficient to generate protein complexes by fusing different cytokines with partner proteins that form stable non-covalent complexes. For example, a non-covalent heterodimer support protein is used: a first cytokine is fused to one subunit of the heterodimer, a second cytokine is fused to a second subunit of the heterodimer, and the two fusion proteins are mixed under appropriate conditions. For example, nucleic acids encoding the two subunit-cytokine fusion proteins are expressed in the same cell. In this way, a multiple cytokine protein complex may be constructed in which the component cytokines are not covalently linked, directly or indirectly. To achieve the purpose of the invention, it is necessary that such a complex is stable enough to be maintained upon administration of an animal and achieve a biological effect.

The invention also provides nucleic acids that encode fusion proteins comprising two or more cytokines, where one of the cytokines is preferably IL-12 and the fusion protein encoded by the nucleic acid optionally includes other protein moieties. Preferred embodiments include nucleic acids that encode fusions of two or more cytokines to a dimerizing protein, such as an Fc portion of an antibody chain. Another set of preferred embodiments are nucleic acids that encode fusions of two or more cytokines to a protein with targeting capability, such as an antibody.

The invention also provides methods for construction of fusions of two or more cytokines, as well as methods for expression of such fusion proteins.

The invention also provides methods for treatment of diseases and other medical conditions, in which treatment involves the useful combination of the activity of two or more proteins. In one embodiment, at least one of the proteins has a short (e.g. less than 20 minutes) or only moderately long (e.g. less than 40 minutes) serum half-life. The proteins are fused by genetic engineering or other techniques and administered to a human or animal. In this way, the activities of the two proteins are present in a fixed ratio, and separate administrations on different dosing schedules of the two proteins are not required. In addition, the serum half-life of the fusion protein will generally be more similar to that of the protein component with the longer serum half-life, thus lengthening the effective half-life of the protein or proteins with the shorter serum half-life.

More specifically, the invention provides methods of immune-therapeutic treatment of diseases, such as cancer or infections or other diseases, that might be usefully treated with a two-chain cytokine such as IL-12 in combination with a second cytokine. In a preferred embodiment, IL-12 is fused with IL-2 or GM-CSF and administered to an animal or human. In other preferred embodiments, GM-CSF is fused to IL-4 and administered to an animal or a human. In another embodiment, IL-12 is fused to IL-18 and administered to an animal or a human. Such treatments can be used in combination with other disease treatments. In addition, the invention provides methods of vaccination against diverse antigens, which can be used to prevent or treat various diseases.

In other embodiments of these methods, two different cytokines are fused to a dimeric protein moiety, such as the Fc region of an antibody, and are administered to an animal or human. In a preferred form of these methods, the cytokine IL-12 is fused to the Fc region along with a second cytokine that is more preferably IL-2 or GM-CSF.

In yet other embodiments of these methods, two different cytokines are fused to an intact antibody, and are administered to an animal or human. In a preferred form of these methods, the cytokine IL-12 is fused to the antibody moiety along with a second cytokine that is more preferably IL-2 or GM-CSF. The invention also discloses mixtures of antibody-cytokine fusion proteins that are useful in treating diseases. In one embodiment, a mixture of an antibody-IL-2 fusion protein and an antibody-IL-12 fusion protein is used to treat disease. For example, cancer, viral infection, or bacterial infection is treated.

BRIEF DESCRIPTION OF THE DRAWINGS

The preceding and other objects of the present invention, and the various features thereof, may be more fully understood from the following descriptions, when read together with the accompanying drawings. Throughout the drawings, like numbers refer to like structures.

FIG. 1 shows how a second cytokine may be fused to a single chain version of IL-12. Specifically, single chain IL-12 molecules may have p35 N-terminal to p40, with the second cytokine at the C-terminus (FIG. 1F) or the N-terminus (FIG. 1G). Alternatively, single chain IL-12 molecules may have p40 N-terminal to p35, with the second cytokine at the C-terminus (FIG. 1H) or the N-terminus (FIG. 1I).

In FIG. 6A, cells were treated with human IL-12 before (squares) or after phytohemagglutinin activation (X's), or with IL-12-IL-2 fusion protein before (diamonds) or after phytohemagglutinin activation (triangles). FIG. 6B shows an experiment in which cells were treated with a mixture of IL-12 plus IL-2 added in a 1:1 molar ratio (black diamonds), human Fc-IL-12-IL-2 fusion protein (gray squares), and human antibody-IL-12-IL-2 fusion protein (light gray triangles). The X axis indicates the concentration of IL-12 in pg/ml, whether present as an intact protein or as a fusion protein. The y-axis indicates IFN-γ concentration (in ng/ml), which was assayed by ELISA.

In FIG. 17A, four sets of mice are compared: C57BL/6 mice injected s. c. with $1\times10^6$ LLC tumor cells (black diamonds); C57BL/6 mice injected s. c. with $5\times10^6$ LLC tumor cells (white diamonds); C57BL/6 mice injected s. c. with $1\times10^6$ LLC tumor cells expressing scIL-12 (black triangles); and C57BL/6 mice injected s. c. with $5\times10^6$ LLC tumor cells expressing scIL-12 (white triangles). FIG. 17B compares C57BL/6 mice injected s. c. with $1\times10^6$ LLC tumor cells (black diamonds); C57BL/6 mice injected s. c. with $5\times10^6$ LLC tumor cells (white diamonds); C57BL/6 mice injected s. c. with $1\times10^6$ LLC tumor cells expressing scIL-12-IL-2 (X's); and C57BL/6 mice injected s. c. with $5\times10^6$ LLC tumor cells expressing scIL-12 (white circles). The x-axis indicates number of days after injection of the tumor cells. The y-axis indicates the tumor volume in cubic millimeters.

DETAILED DESCRIPTION OF THE INVENTION

Figure 1A:
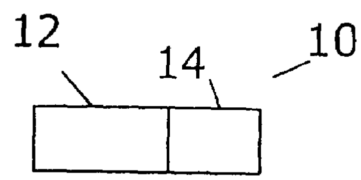
FIG. 1A schematically illustrates the fusion of two cytokines in its simplest form: one cytokine is fused to a second cytokine, optionally through a linker.
Figure 1B:
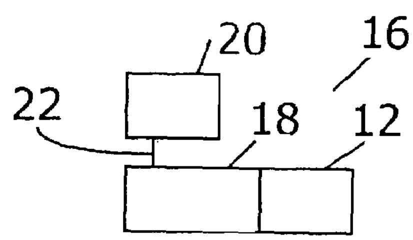
FIGS. 1B-1I show various ways in which a second cytokine (labeled 'cyt') may be attached to the heterodimeric cytokine IL-12. Specifically, the second cytokine can be fused to the C-terminus of p40 (FIG. 1B), the N-terminus of p40 (FIG. 1C), the C-terminus of p35 (FIG. 1D) or the N-terminus of p35 (FIG. 1E). In addition.
Figure 1C:
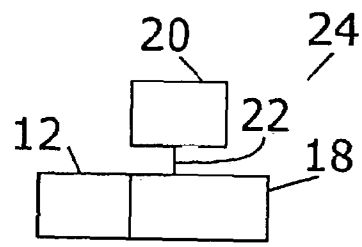

The invention provides protein molecules in which two or more distinct cytokines are fused or complexed. The protein complexes or fusion proteins may optionally include additional protein moieties, including moieties capable of multimerization and targeting such as antibody Fc regions and antibody regions that include antigen combining sites. The invention also provides nucleic acids encoding multiple-cytokine fusion proteins. The invention also provides methods for the construction of nucleic acids encoding multiple-cytokine fusion proteins, methods for production of multiple-cytokine fusion proteins, and methods for use of multiple-cytokine fusion proteins in treatment of diseases and medical conditions.

As used herein, "cytokine" refers to a secreted protein or active fragment or mutant thereof that modulates the activity of cells of the immune system. Examples of cytokines include the interleukins, interferons, chemokines, tumor necrosis factors, colony-stimulating factors for immune cell precursors, and so on.

As used herein, "heterodimeric cytokine" refers to a cytokine consisting of two distinct protein subunits. At present, IL-12 is the only naturally occuring heterodimeric cytokine that is known. However, artificial heterodimeric cytokines can be constructed. For example, IL-6 and a soluble fragment of IL-6R can be combined to form a heterodimeric cytokine, as can CNTF and CNTF-R alpha [Trinchieri (1994) Blood 84:4008].

As used herein, "interleukin-12" (IL-12) refers to the two-subunit cytokine consisting of a p35 and p40 subunit, or an active single-chain fusion of p35 and p40, or a species variant, fragment, or derivative thereof.

As used herein, "interleukin-2" (IL-2) refers to any mammalian IL-2, such as human IL-2, mouse IL-2, or an active species or allelic variant, fragment or derivative thereof.

As used herein, "GM-CSF" refers to a mammalian Granulocyte/Monocyte-Colony Stimulating Factor cytokine protein, such as human GM-CSF, mouse GM-CSF, or an active species or allelic variant, fragment or derivative thereof.

As used herein, "immunoglobulin Fc region" means the carboxyl-terminal portion of an immunoglobulin heavy chain constant region, or an analog or portion thereof. For example, an immunoglobulin Fc region of IgG may comprise at least a portion of a hinge region, a CH2 domain, and a CH3 domain. In a preferred embodiment the Fc region includes at least a portion of a hinge region and a CH3 domain. In another preferred embodiment, the Fc region includes at least a CH2 domain and more preferably also includes at least a portion of a hinge region.

As used herein, "peptide linker" means one or more peptides used to couple two proteins together (e.g. a protein and an Fc region). The peptide linker often is a series of amino acids such as. e.g., predominantly glycine and/or serine. Preferably, the peptide linker is a mixed series of predominantly glycine and serine residues and is about 10-15 amino acids in length.

As used herein, the term "multimeric" refers to the stable association of two or more protein subunits through covalent or non-covalent interaction, e.g. disulphide bonding.

As used herein, the term "dimeric" refers to a specific multimeric molecule where two protein subunits are associated stably through covalent or non-covalent interactions. A stable complex is a complex with a dissociation rate, or off-rate, of at least several minutes (such that the complex would be stable long enough during in vivo use to reach a target tissue and have a biological effect. The Fc fragment itself typically forms a dimer of the heavy chain fragments comprising a portion of the hinge region, CH2 domain and/or CH3 domain. However, many protein ligands are known to bind to their receptors as a dimer. If a cytokine X dimerizes naturally, the X moiety in an Fc-X molecule will dimerize to a much greater extent, since the dimerization process is concentration dependent. The physical proximity of the two X moieties connected by Fc would make the dimerization an intramolecular process, greatly shifting the equilibrium in favor of the dimer and enhancing its binding to the receptor.

As used herein, "vector" means any nucleic acid comprising a nucleotide sequence competent to be incorporated into a host cell and to be recombined with and integrated into the host cell genome, or to replicate autonomously as an episome. Such vectors include linear nucleic acids, plasmids, phagemids, cosmids, RNA vectors, viral vectors and the like. Non-limiting examples of a viral vector include a retrovirus, an adenovirus and an adeno-associated virus.

As used herein, "gene expression" or "expression of a protein" is understood to mean the transcription of the DNA sequence, translation of the mRNA transcript, and either secretion of a protein product or production of the protein product in an isolatable form.

As used herein, an "immunocytokine" is a fusion protein comprising an antibody and a cytokine, as disclosed in U.S. Pat. No. 5,650,150.

As used herein, a "leader sequence" is a protein sequence that is attached, usually at the N-terminus, to a second protein sequence, and that directs the second protein sequence to be secreted from a cell. The leader sequence is usually cleaved and removed from the second protein sequence, which becomes the mature protein. The term "leader sequence" is generally synonymous with "signal sequence".

As used herein, "EpCAM" refers to epithelial cell adhesion molecule (Cirulli et al. [1998] 140:1519-1534), and is synonymous with "KSA," meaning the antigen bound by the monoclonal antibody KS-1/4. EpCAM is a cell surface protein that is abundantly expressed on cancer cells derived from epithelial cells.

As used herein, "KS-1/4" refers to a particular monoclonal antibody that binds to EpCAM.

As used herein, "KS-IL2," "KS-IL12," and "KS-IL12-IL2" (and the like) refer to antibody-cytokine fusion proteins consisting of KS-1/4 with interleukin-2, KS-1/4 with interleukin-12, and KS-1/4 with both interleukin-12 and interleukin-2, respectively. Analogously named fusion protein constructs are also used herein. Because it is possible to fuse cytokines at several positions on an antibody molecule, a description such as "KS-IL12-IL2" refers to the class of proteins comprising KS-1/4 with both interleukin-12 and interleukin-2 fused at any possible position, unless explicitly stated otherwise.

As used herein, "14.18" refers to a particular monoclonal antibody that binds to the tumor-specific antigen GD2.

Several illustrative embodiments of protein constructs embodying the invention are illustrated in FIGS. 1-5. Parts of the molecules diagrammed in FIGS. 2-5 are labeled 1A-1I, referring to the fusion proteins shown in FIGS. 1A-1I and illustrating that any of the fusion proteins from FIG. 1 can be further fused to other proteins as indicated. Cytokines are shown as rectangles, constant regions of antibodies are shown as ovals, and the heavy chain variable region and light chain variable region are shown as labeled ovals.

The present invention describes protein complexes containing two different cytokines and optionally including additional protein moieties. A homodimeric cytokine (e.g. interferon alpha, interferon beta, interferon gamma, IL-5, IL-8, or the like), although it contains multiple subunits, is nevertheless a single cytokine. Similarly, a heterodimeric cytokine such as IL-12, although it contains subunits that are different, is a single cytokine. Furthermore, a heterodimeric form of normally homodimeric cytokines, such as a MCP-1/MCP-2 heterodimer, or of two alleles of a normally homodimeric cytokine (e.g., Zhang, *J. Biol. Chem. [*1994] 269:15918-24) is a single cytokine. The complexes of the present invention contain two different cytokines, each of which (e.g. IL-2 and IL-12; IL-4 and GM-CSF; MCP-1 and eotaxin; etc.) is capable of modulating an activity of a cell of the immune system.

FIG. 1A depicts a preferred embodiment of the invention: in fusion protein 10, the C-terminus of a first cytokine 12 is fused to the N-terminus of a second cytokine 14, optionally through a linker region (not shown). In some embodiments of the invention, the protein complex of the invention contains at least two cytokines with significantly different serum half-lives. For example, using a small and a large protein will often result in a fusion protein with a circulating half-life characteristic of the larger protein. Therefore, in situations where the combined effects of IL-12 and a second cytokine are desired, it would be advantageous to express the two cytokines as a fusion protein of the general formula: IL-12-X or X-IL-12, where X is a second cytokine. Two particular advantages are seen. First, the serum half-life of the more rapidly cleared cytokine is extended. Second, the serum half-lives of both cytokines become very similar to each other.

Figure 1D:
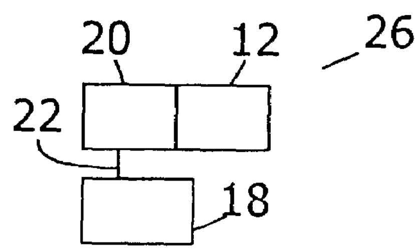
Figure 1E:
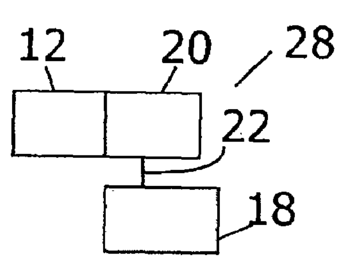
Figure 1F:
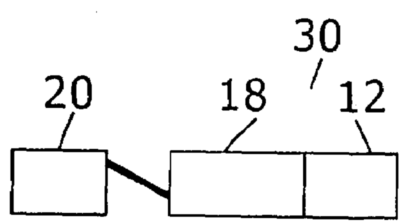
Figure 1G:
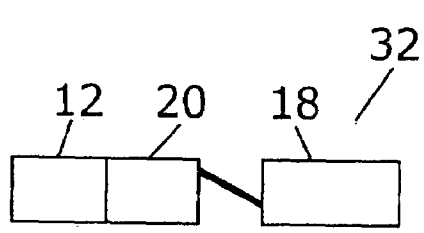

A two-chain cytokine such as IL-12 can be fused to another cytokine at the N- or C-terminus of either the chain of the two-chain cytokine. In one embodiment, a second cytokine is fused at either the N-terminus or C-terminus of either the p35 or p40 subunit of IL-12 (FIGS. 1B-1E). In fusion protein 16 of FIG. 1B, the N-terminus of a first cytokine 12 is fused to the C-terminus of the IL-12 subunit p40 18. Subunit p40 18 is connected to IL-12 subunit p35 20 by a covalent bond 22. In fusion protein 24 of FIG. 1C, the N-terminus of p40 subunit 18 is fused to the C-terminus of first cytokine 12 and is connected to p35 subunit 20 by a covalent bond 22. FIG. 1D depicts fusion protein 26 in which the N-terminus of first cytokine 12 is fused to the C-terminus of p35 subunit 20, which is connected by covalent bond 22 to p40 subunit 18. In FIG. 1E, fusion protein 28 includes p35 subunit 20, fused at its N-terminus to the C-terminus of first cytokine 12 and connected by covalent bond 22 to p40 subunit 18.

Figure 1H:
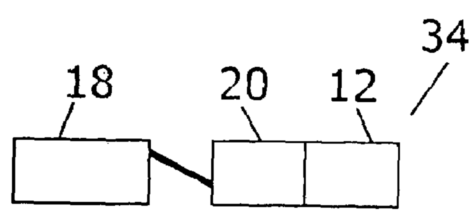
Figure 1I:
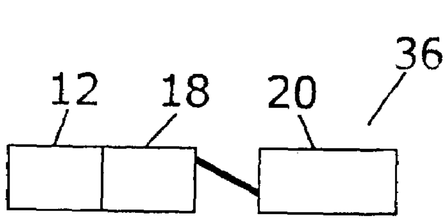

In a second embodiment, the subunits of IL-12 may be fused to form a single-chain protein, scIL-12, with either the p35 subunit or the p40 subunit at the N-terminal position; the second cytokine may be attached to the N- or C-terminus of the resulting scIL-12 (FIGS. 1F-1I). Thus, in a preferred embodiment depicted in FIG. 1F, fusion protein 30 contains single-chain IL-12, in which the N-terminus of p40 subunit 18 is fused to the C-terminus of p35 subunit 20, optionally through a peptide linker. In this embodiment the N-terminus of cytokine 12 is fused to the C-terminus of p40 subunit 18. In the embodiment shown in FIG. 1G, the N-terminus of p35 subunit 20 is fused to the C-terminus of cytokine 12, optionally through a peptide linker. FIGS. 1H and 1I show fusion proteins 34 and 36 containing another single-chain version of IL-12 in which the N-terminus of the p35 subunit is fused to the C-terminus of the p40 subunit, optionally through a peptide linker. In fusion protein 34, shown in FIG. 1H, the N-terminus of cytokine 12 is fused to the C-terminus of p35 subunit 20. In fusion protein 36, shown in FIG. 1I, the N-terminus of p40 subunit 18 is fused to the C-terminus of cytokine 12. In a highly preferred embodiment, IL-12 is fused to IL-2.

The production of such molecules is further illustrated in the examples.

It is often convenient to express heteromultimeric molecules, such as IL-12 or an antibody, as single-chain molecules in which the non-identical subunits are connected by short amino acid linkers [Huston et al (1988) Proc. Nat. Acad. Sci. 85: 5879; Lieschke et al. (1997) Nat Biotechnol. 15:35; Lieschke; G. J. and Mulligan; R. C., U.S. Pat. No. 5,891,680]. A gene fusion is constructed, and then the desired protein can be expressed in cells containing a single recombinant DNA construct. Such single-chain versions of a heteromultimeric cytokine can be further fused to a second cytokine, which still allows a fusion protein with the desired activities to be expressed from a single recombinant DNA construct. The expression of such molecules is illustrated in the examples.

The invention also describes a fusion protein comprising IL-4 and GM-CSF. This combination is particularly useful in functionally stimulating antigen presentation by dendritic cells. Another useful fusion comprises IL-12 and IL-18. These cytokines both promote the Th1 response, but have somewhat different, complementary activities.

The invention also describes fusion proteins in which multiple distinct, fused cytokines are further fused to a protein capable of forming multimers, such as homodimers or heterodimers. The advantage of such a molecule is that the potency of one or more of the cytokines may be enhanced by dimerization. In some cases, enhancement of potency by dimerization can occur because the cytokine binds to its receptor as a dimer. In one embodiment, multiple cytokines are fused to a portion of an antibody molecule, such as an Fc region (FIG. 2). In another embodiment, IL-12 and a second cytokine are fused to the homodimerizing protein moiety. In a preferred embodiment, the second cytokine is IL-2 or GM-CSF. The fusion proteins may be created in a variety of ways, reflecting all the various orderings of several distinct protein moieties from the N- to C-termini in a fusion protein. For example when interleukin-12 and a second cytokine are fused to an Fc region, the two cytokines may be both fused in any order to the N- or C-terminus of the Fc region, or one cytokine may be fused at the N-terminus and the other at the C-terminus.

Figure 2A:
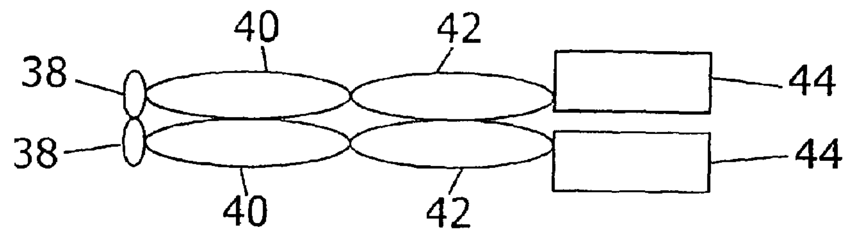
FIGS. 2A-2C schematically show how multiple-cytokine fusions (boxed) depicted in FIG. 1 may be further fused to an Fc region of an antibody, shown here as a hinge (H), a CH2 domain and a CH3 domain (ovals). Specifically, any of the eight molecules of FIG. 1 may be fused to either the C-terminus (FIG. 2A) or N-terminus (FIG. 2B) of the Fc region. In addition, the first cytokine and second cytokine (each boxed) need not be directly attached to each other, but can be connected through the Fc moiety (FIG. 2C).
Figure 2B:
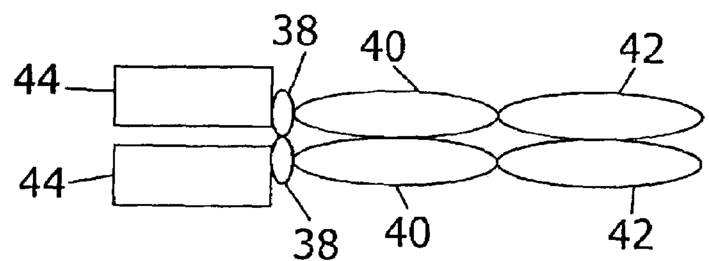
Figure 2C:
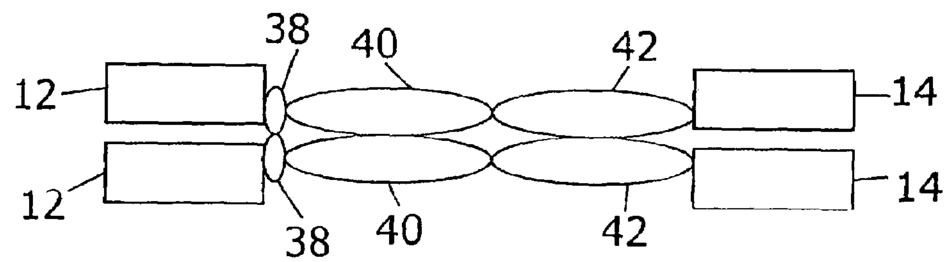

Some of these permutations are illustrated in FIG. 2. For example, in the embodiment shown in FIG. 2A, a fusion protein 44 of the invention is fused to the C-terminus of an Fc region containing hinge region 38, CH2 region 40 and CH3 region 42. Fusion protein 44 could have a variety of structures, including, for example, the structures of fusion proteins 10, 16, 24, 26, 28, 30, 32, 34, or 36 depicted in FIGS. 1A-1I. If fusion protein 44 has more than one N-terminus and C-terminus, as in fusion proteins 16, 24, 26, and 28, the Fc region could be fused to either N-terminus of fusion protein 44. As shown in FIG. 2B, fusion protein 44 could be fused to the N-terminus of an Fc region. In the embodiment shown in FIG. 2C, a first cytokine 12 could be fused to the N-terminus of an Fc region, and a second cytokine 14 could be fused to the C-terminus of the Fc region.

Structural Considerations

It is important to note that cytokines, as a class of proteins, are similar in size and in general folding properties. Thus, the specific examples disclosed herein illustrate how to construct multiple cytokine fusion proteins for the family of cytokine proteins. For example, many cytokines fall into a protein folding class termed the "four-helix bundle". Four helix bundle proteins include granulocyte-colony stimulating factor (G-CSF), interleukin 6 (IL-6), leukemia inhibitory factor (LIF), growth hormone, ciliary neurotrophic factor (CNTF), leptin, erythropoietin, granulocyte-macrophage colony stimulating factor (GM-CSF), interleukin-5 (IL-5), macrophage colony-stimulating factor (M-CSF), IL-2, IL-4, interleukin-3 (IL-3), IL-10, interferon-beta, the interferon alphas and the closely related inteferon tau, and interferon gamma (IFN-gamma).

With the exception of IL-5 and IFN-gamma, all of these proteins fold as monomers with four roughly parallel alpha helices and two crossover connections. In each case except IL-5 and IFN-gamma, the N-terminus and the C-terminus are on the same face of the protein. Because the four-helix bundle proteins, except IL-5 and IFN-gamma, have the same folding pattern, the methods described herein for IL-2, IL-4 and GM-CSF also apply to other four-helix bundle proteins and other small cytokine proteins that fold as monomers.

Chemokines are a specific class of cytokines that are thought to form extracellular gradients and mediate the chemotaxis of specific classes of immune cells. For example, MCP-1 is a chemoattractant for monocytes, macrophages, and activated T cells; eotaxin is a chemoattractant for eosinophils; and interleukin-8 is a chemoattractant for neutrophils. In addition to their chemoattractant function, chemokines, like other cytokines, are able to induce the expression of specific genes in specific target cells. For example, MCP-1 is thought to induce the expression of Tissue Factor in vascular smooth muscle cells (Schecter et al., J Biol Chem. [1997] 272:28568-73).

The invention discloses cytokine-cytokine fusions and antibody-cytokine-cytokine fusions in which one or more cytokines is a chemokine. The invention also discloses protein constructs with three or more cytokines, in which one or more cytokine is a chemokine. For example, the chemokines IP-10, RANTES, MIP-1alpha, MIP-1beta, macrophage chemoattractant proteins, eotaxin, lymphotactin, BLC, can be fused to a second cytokine with or without other moieties such as an antibody moiety.

The human genome, for example, encodes at least 50 chemokines. Known chemokines generally share a similar three-dimensional monomer structure and protein folding pattern. Accordingly, the general types of protein constructs and construction strategies disclosed here can be applied to a variety of known or as-yet-undiscovered chemokines.

Chemokines have a distinct folding pattern with three beta-strands and one alpha helix. Chemokines fold as monomers and, in some but not all cases, then dimerize after folding. For all chemokines, the folding pattern of the monomer subunit is identical and the overall structures are extremely similar. For example, the three dimensional structures of Interleukin-8, Platelet factor 4, Melanoma growth stimulating activity (MGSA), Macrophage inflammatory protein, MIP, RANTES (regulated upon activation, normal T-cell expressed and secreted), Monocyte chemoattractant protein-1 (MCP-1, MCAF), Eotaxin, Monocyte chemoattractant protein-3 (MCP-3), Chemokine domain of fractalkine, Neutrophil-activating peptide-2 (NAP-2), Stromal cell-derived factor-1 (SDF-1), Macrophage inflammatory protein-2, Chemokine hcc-2 (macrophage inflammatory protein-5), Gro beta, Cytokine-induced neutrophil chemoattractant, and CINC/Gro have been determined by X-ray crystallography and/or NMR methods; all of these structures show the same fold and are generally similar. Because the chemokines have the same folding pattern, the methods described herein for lymphotactin also apply to other chemokine proteins.

A free N-terminus of a chemokine is often important for its function. Therefore, it is advantageous in some embodiments to construct fusions in which a second cytokine, antibody moiety, or other protein moiety may be fused to the C-terminus of the chemokine. To construct a protein complex containing two active chemokines, it is useful, for example, to fuse the two different chemokines to the N-termini of an antibody's heavy and light chains. Some chemokines, such as IL-8, are dimeric under physiological conditions. For certain applications, it is useful to coexpress a multiple cytokine antibody fusion, such as an IL-8-antibody-cytokine fusion, along with an unfused IL-8 moiety or an IL-8 moiety with a different fusion partner that does not interact with the antibody moiety. In this way, the different IL-8 moieties can heterodimerize without spatial constraints or polymerization that might result if all IL-8 moieties were fused to an antibody chain. The desired multiple cytokine fusion protein can then be separated on the basis of size or on the basis of binding to an antibody-binding protein such as Staphylococcus A protein.

For multiple cytokine fusion proteins comprising a chemokine, it is a preferred embodiment that the fusion protein also comprises a localizing function, such as an antibody moiety that binds to an antigen. Without wishing to be bound by theory, it is generally thought that body-wide distribution of a chemokine will have no effect or lead to a general desensitization of cells toward that chemokine. In addition, it is thought that the chemoattractant function of a chemokine can only be manifested when there is a concentration differential of the chemokine.

A preferred embodiment is a lymphokine-antibody-interleukin-2 fusion protein. Another preferred embodiment is one in which both the chemokine and the second cytokine promote a Th1 response. For example, a fusion protein comprising IP-10 and IL-12 is one highly preferred embodiment.

Extending the Half-life of Multiple Cytokines with Short Serum Half-lives

The invention also describes fusion proteins comprising two cytokines, both with a short serum half-life, fused to a third moiety with a long serum half-life. For example, when stimulation of dendritic cells is desired, it is useful to combine the activities of IL-4 and GM-CSF (Thurner, J Immunol. Methods [1999] 223:1-15; Palucka, et al. [1998] J. Immunol. 160:4587-4595). Because both IL-4 and GM-CSF are small molecules with short serum half-lives, it is useful to construct a fusion protein comprising an Fc region, IL-4, and GM-CSF. The resulting molecule is a powerful stimulant of dendritic cell proliferation and activity. Likewise, both IL-4 and GM-CSF could be fused to a targeting component such as an antibody for the purpose of delivering the combined cytokine activities to the site of cells expressing a predetermined antigen.

The Fc region, alone or as part of an intact antibody, can confer several properties to multiple cytokine fusions that may be advantageous or disadvantageous, depending on the specific application. These properties include dimerization, extension of serum half-life, ability to fix complement, ability to mediate antibody-dependent cell-mediated cytotoxicity (ADCC), and binding to Fc receptors. If extension of serum half-life is a primary desired feature and immunological properties of the Fc region are unimportant or undesirable, it is preferable to use an Fc region that is a natural variant or mutant lacking one or more immunological properties. For example, if it is desirable to equalize and extend the serum half-lives of two or more cytokines with short serum half-lives, it is preferable to construct a multiple cytokine fusion protein comprising an Fc region from human IgG2 or IgG4, which respectively have reduced or no affinity for Fc receptors, or to use an Fc region carrying a mutation in the Fc receptor binding site. In fact, it has already been shown that fusion of some cytokines to antibodies increases the affinity of the fusion protein to Fc receptors and that this results in faster rates of clearance in animals. The use of Fc regions with reduced affinity for Fc receptors was shown to greatly improve the serum half-life of these molecules (Gillies et al. [1999] Cancer Res. 59:2159-2166). Under some circumstances and depending on the cytokines used, an Fc region that binds to the Fc receptor will result in internalization of the multiple cytokine fusion protein and degradation of one or more cytokine moieties.

Targeting

The invention also describes fusion proteins in which two or more cytokines are attached to a protein that is capable of localizing the cytokines to a particular target molecule, cell, or bodily location. The preferred molecule with localizing capability is an antibody or a moiety comprising the antigen-binding variable regions of an antibody. However, other localizing molecules, or domains thereof, may be used, such as specific ligands or receptors, naturally occurring binding proteins, enzymes that bind to particular substrates, artificially generated peptides that have been selected for a particular binding or localizing capability, peptides with distinctive physico-chemical properties that result in a targeting capability, proteins that possess a targeting capability by virtue of binding to another molecule that is targeted, or other types of proteins. In the case of fusing two cytokines to a targeting molecule, a preferred first cytokine is IL-12. When IL-12 is used, a preferred second cytokine is IL-2 or GM-CSF.

In the case of an antibody, there are a large number of ways in which two or more cytokines can be fused, because there are several possible sites of attachment For example, an IgG antibody consists of two heavy and two light chains. The two cytokines may be fused to each other and then fused to an N- or C-terminus of either the heavy or the light chain. Alternatively, each cytokine may be fused separately to one of the N- or C-termini on the antibody molecule.

FIG. 3 illustrates a subset of ways in two cytokines may be fused to an antibody molecule. For example, referring to FIG. 3A, a fusion protein 44 of the invention could be fused to the C-terminus of an immunoglobulin heavy chain 46, which is associated with an immunoglobulin light chain 48. As in FIG. 2, fusion protein 44 can have a variety of structures, including, for example, the structures of fusion proteins 10, 16, 24, 26, 28, 30, 32, 34, or 36 depicted in FIGS. 1A-1I. As shown in FIG. 3B, a fusion protein 44 could be fused to the N-terminus of an immunoglobulin heavy chain 46 associated with an immunoglobulin light chain 48. In the embodiments shown in FIGS. 3C and 3D, fusion protein 44 is fused to the N-terminus (FIG. 3C) or the C-terminus (FIG. 3D) of an immunoglobulin light chain 48 associated with an immunoglobulin heavy chain 46. As shown in FIGS. 3E and 3F, a first cytokine 12 may be fused to an immunoglobulin light chain 48 associated with an immunoglobulin heavy chain 46 fused to a second cytokine 14. The cytokines 12 and 14 may be fused to the N-termini (FIG. 3E) or the C-termini (FIG. 3F) of the immunoglobulin chains. Alternatively, as in FIG. 3G, first cytokine 12 may be fused to the N-terminus of the immunoglobulin light chain 48 while the second cytokine 14 is fused to the C-terminus of the immunoglobulin heavy chain 46.

Fusions to Single-Chain Antibodies

It is sometimes convenient to express antibodies as single-chain molecules. The invention also provides fusion proteins in which two or more cytokines are fused to a single-chain antibody. This has the advantage of reducing the number of the DNA constructs used when expressing the desired fusion protein, which may be especially useful in gene therapy. In particular, if the cytokines are single-chain molecules, then fusion of the cytokines to the single-chain antibody will allow expression of the fusion protein as a single protein chain.

Figure 4A:
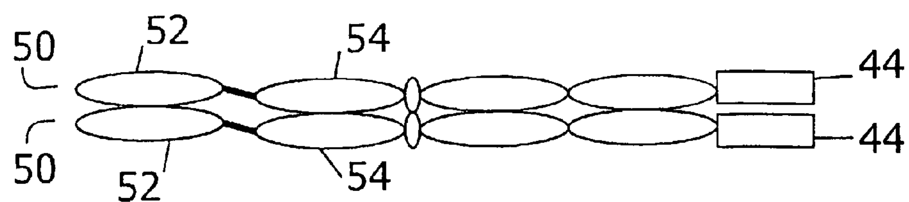
FIGS. 4A-4C schematically show how a first cytokine and a second cytokine may be fused to a "single-chain" antibody in which the variable light and variable heavy chains are fused, and the protein is expressed as a single polypeptide that then homodimerizes. Specifically, a multiple cytokine fusion may be placed at the C-terminus (FIG. 4A), or the N-terminus (FIG. 4B). In addition, the a first cytokine and second cytokine need not be directly attached, but can be connected through the single-chain antibody moiety (FIG. 4C).
Figure 4B:
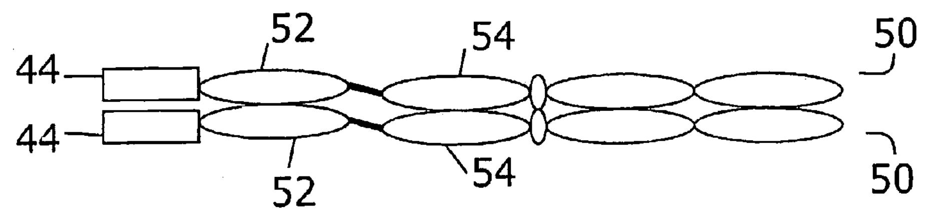
Figure 4C:
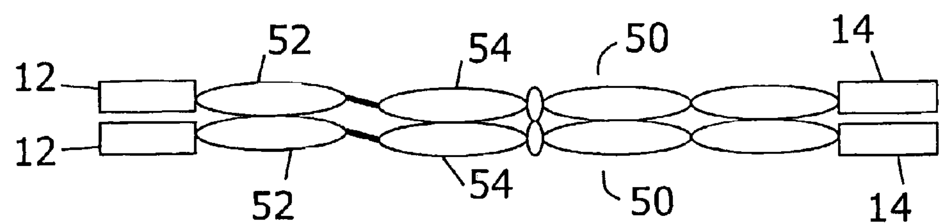

As shown in FIGS. 4A-4C, in some embodiments, cytokines can be fused to the single-chain antibody at its N-terminus, its C-terminus, or at both termini. For example, as shown in FIG. 4A, fusion protein 44 can be fused to the C-terminus of single-chain antibody 50 having light chain variable region 52 and heavy chain variable region 54. As shown in FIG. 4B, fusion protein 44 can also be fused to the N-terminus of single-chain antibody 50. In the embodiment shown in FIG. 4C, a first cytokine 12 is fused to the N-terminus of single-chain antibody 50, and a second cytokine 14 is fused to the C-terminus of single-chain antibody 50.

A preferred embodiment comprises a fusion of IL-12 and a second cytokine to the single-chain antibody. A more preferred embodiment comprises IL-2 or GM-CSF as the second cytokine.

The constant regions of antibodies have the potential to mediate a variety of effector functions. For example IgG1 mediates complement fixation, ADCC, and binding to Fc receptor. The position at which the cytokine is fused may alter the antibody constant region's effector function, which is useful if modulation of these effector functions is desired.

In some cases it may be desirable to construct a fusion of two or more cytokines to a moiety with the targeting region of an antibody, but without the constant regions. Such a fusion protein is smaller than a fusion of a complete antibody to two or more cytokines, which may be advantageous for certain purposes. In addition, such a fusion protein will lack one or more of the effector functions of an intact antibody, but will retain the targeting capability of an antibody.

The invention therefore features fusion proteins in which two or more cytokines are fused to a single-chain Fv region.

Figure 5A:
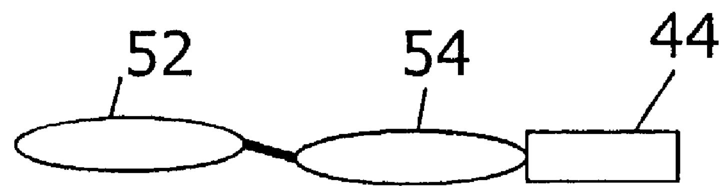
FIGS. 5A-5C schematically show how a first cytokine and a second cytokine may be fused to a single-chain Fv region consisting of the fused variable regions from a heavy chain and a light chain. Specifically, a first cytokine-cytokine fusion may be placed at the C-terminus (FIG. 5A), or the N-terminus (FIG. 5B). In addition, the first cytokine and second cytokine need not be directly attached, but can be connected through the single-chain Fv moiety (FIG. 5C).
Figure 5B:
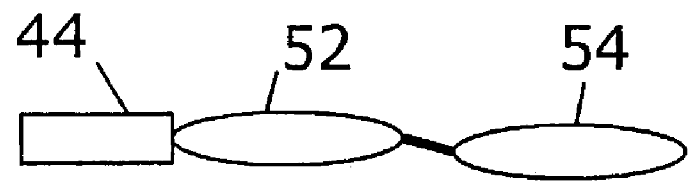
Figure 5C:
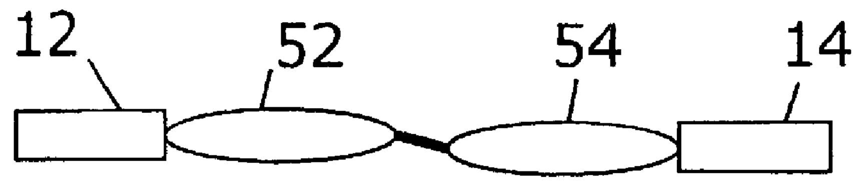

As shown in the embodiments depicted in FIGS. 5A-5C, two cytokines may be fused to the N-terminus or the C-terminus of the Fv region, or one cytokine to each terminus. For example, as shown in FIG. 5A, a fusion protein 44 of the invention may be fused to the C-terminus of a single-chain Fv region containing an immunoglobulin light chain variable region 52 and an immunoglobulin heavy chain variable region 54. A fusion protein 44 may also be fused to the N-terminus of an Fv region as shown in FIG. 5B. As shown in FIG. 5C, a first cytokine 12 may be fused to the N-terminus of an Fv region, and a second cytokine 14 may be fused to the C-terminus of the Fv region.

Antibodies as Heterodimeric Vehicles for Multiple Cytokines

In some circumstances, it is desirable to construct a fusion of two or more cytokines in which, for two of the cytokines, the same end of the protein is essential for activity. For example, it may be that the naturally occurring N-terminus of two different cytokines is essential for the activity of each cytokine. It is not possible to construct a single polypeptide chain fusion protein in which both cytokine moieties would be active.

Figure 3A:
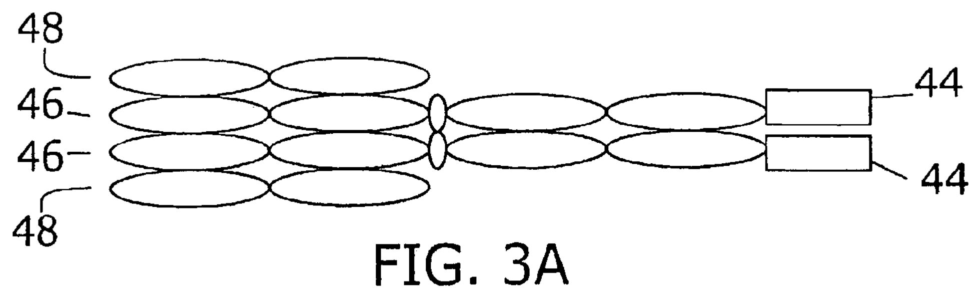
FIGS. 3A-3G schematically show a subset of the ways in which a multiple cytokine fusion protein may be further fused to an intact immunoglobulin such as an IgG. The heavy chain V region is shown as an oval labeled $V_H$, the light chain V region is shown as an oval labeled $V_L$, and constant regions are blank ovals. A multiple cytokine fusion, as illustrated in FIG. 1, may be placed at the C-terminus of the heavy chain (FIG. 2A), the N-terminus of the heavy chain (FIG. 2B), the N-terminus of the light chain (FIG. 2C), or the C-terminus of the light chain (FIG. 2D). In addition, there are many ways in which a first and second cytokine could be separately attached at the N- and C-termini of the heavy and light chains; three of these are shown in FIGS. 3E-3G.
Figure 3B:
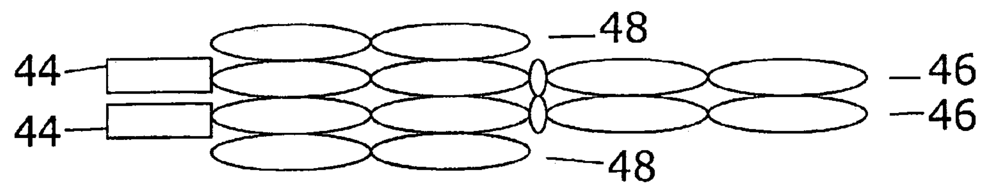
Figure 3C:
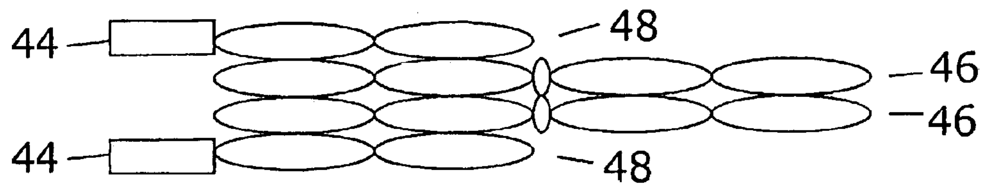
Figure 3D:
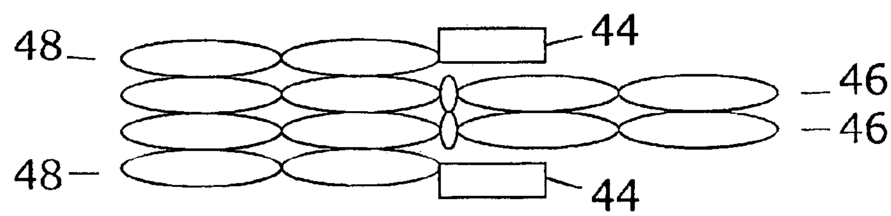
Figure 3E:
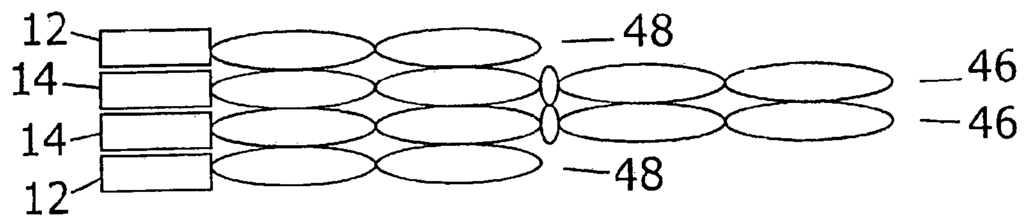
Figure 3F:
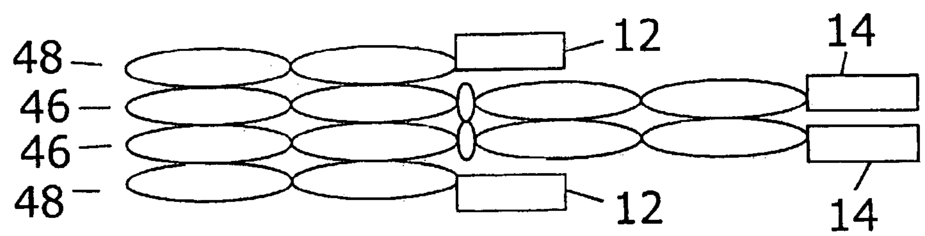

Antibodies are heterodimeric proteins consisting of heavy and light chains that are covalently linked by disulfide bonds. If it is desired to construct a multiple cytokine fusion protein with two cytokine moieties that both require an intact, unfused N-terminus, it is preferable to separately fuse the two cytokines to the N-termini of the heavy and light chains of an antibody (FIG. 3E). Similarly, if it is desired to construct a multiple cytokine fusion protein with two cytokine moieties that both require an intact, unfused C-terminus, it is preferable to separately fuse the two cytokines to the C-termini of the heavy and light chains of an antibody (FIG. 3F). If the antibody is used solely as a vehicle to connect two cytokines in this manner, it may be useful to mutate or delete those portions of the antibody that confer additional properties related to immune function. For example, it may be preferable to use an Fab region as a vehicle, since the Fab region retains the heterodimerization feature of an antibody but lacks the functions characteristic of the Fc region. It may also be useful to use an antibody or antibody fragment in which the antigen combining site is non-functional.

Fusions of multiple cytokines to antibodies combine many of the novel features of the invention. In antibody-multiple cytokine fusions, the serum half-life of the cytokines is equalized and extended; the activity of both cytokines is localized to a target and the especially toxic effects due to systemic administration of multiple, synergistically acting cytokines are avoided; each cytokine is effectively dimerized or multimerized; and the cytokines do not need to be directly fused but may be fused to different sites on the heavy and light chains of the antibody molecule.

In designing a fusion protein comprising multiple cytokines and an antibody, there are a number of options and configurations that can be distinguished by routine experimentation. Structural biology considerations are also useful. For example, many cytokines fall into a class termed 4-helix bundles. These structures consist of four alpha helices and have the N-terminus and C-terminus in the same vicinity. In general, the face of a cytokine around the N- and C-terminus is not used in binding to a cytokine receptor, so either terminus can be used for fusion to and antibody or to a second cytokine. However, it is sometimes difficult to directly fuse both the N- and C-terminus of a 4-helix bundle cytokine to different moieties, for steric reasons. When it is desirable to fuse two different 4-helix bundle cytokines to an antibody, it is therefore useful to fuse each cytokine to a different site on the antibody. Alternatively, if it is necessary to construct a polypeptide chain of the form Ig chain-cytokine-cytokine, one or more flexible linkers may be used to overcome the steric problems.

Instead of an antibody, it is also possible to use other secreted heterodimeric molecules to carry multiple cytokines. For example, a complex including prostate-specific antigen and the protease inhibitor with which it complexes, the IgA heavy chain and the J chain, members of the TGF-beta family and their astacin-like binding partners, or IL-12 could be used.

Nucleic Acids

The invention also features nucleic acids capable of expressing each of the above types of proteins. These include nucleic acids encoding fusion proteins comprising two or more cytokines, fusions comprising two or more cytokines and a dimerization domain such as an Fc region, fusions comprising two or more cytokines fused to an antibody, and two or more cytokines fused to an Fv region. Preferred forms of the nucleic acids are DNA vectors from which the fusion proteins can be expressed in either bacteria or mammalian cells. For fusion proteins that comprise multiple polypeptide chains, more than one encoding nucleic acid may be used. Alternatively, it may be useful to place two or more fusion protein coding sequences on a single nucleic acid molecule. The Examples illustrate particular forms of the featured nucleic acids encoding multiple cytokines.

The nucleic acids of the invention are particularly useful for expression of multiple cytokine fusion proteins, for either the production of these proteins or for gene therapy purposes.

Methods for synthesizing useful embodiments of the invention, as well as assays useful for testing their pharmacological activities, are described in the Examples.

The present invention also provides pharmaceutical compositions and methods of their use in treatment and prevention of a wide variety of diseases, including but not limited to treatment of various infections and cancer, and vaccination against various diseases.

Multiple cytokine fusion proteins can be used to treat bacterial, parasitic, fungal, or viral infections, or cancer. For example, IL-12 is known to have a protective effect in many types of infections, including but not limited to infections with the bacterium *Listeria monocytogenes*; the parasites *Toxoplasma gondii, Leishmania major*, and *Schistosoma mansoni*; the fungus *Candida albicans*; and the viruses choriomeningitis virus and cytomegalovirus. Since cytokines generally act in combination, it is often useful to use fusion proteins comprising two or more cytokines that are known to act synergistically. For example, since IL-2 potentiates the effects of IL-12, it is useful to combine these cytokines in treatment of bacterial, parasitic, fungal and viral diseases.

A preferred method of treatment of infectious disease is to use multiple cytokine fusion proteins that are further fused to a targeting agent that places the multiple cytokine at the site of infection. Various targeting strategies are described below.

The pharmaceutical compositions of the invention may be used in the form of solid, semisolid, or liquid dosage forms, such as, for example, pills, capsules, powders, liquids, suspensions, or the like, preferably in unit dosage forms suitable for administration of precise dosages. The compositions will include a conventional pharmaceutical carrier or excipient and, in addition, may include other medicinal agents, pharmaceuticals agents, carriers, adjuvants, etc. Such excipients may include other proteins, such as, for example, human serum albumin or plasma proteins. Actual methods of preparing such dosage forms are known or will be apparent to those skilled in the art. The composition or formulation to be administered will, in any event, contain a quantity of the active component(s) in an amount effective to achieve the desired effect in the subject being treated.

Administration of the compositions hereof can be via any of the accepted modes of administration for agents that exhibit such activity. These methods include oral, parenteral, or topical administration and otherwise systemic forms. Injection is a preferred method of administration.

The amount of active compound administered will, of course, be dependent on the subject being treated, the severity of the affliction, the manner of administration, and the judgment of the prescribing physician.

As described above, cytokines such as IL-2, IL-12, GM-CSF, IL-4, and others have been investigated for treatment of cancer. Under some circumstances it is advantageous to use a multiple cytokine fusion protein in treatment of cancer, for reasons of simpler administration, increased serum half-life of one of the component cytokines, and/or superior modulation of the relative activities of the two cytokines.

A preferred method of treatment of cancer is to target the cytokines to a particular organ or tissue, so the effect of the cytokines may be concentrated and the side effects of systemic distribution may be avoided. For example, fusions of multiple cytokines to an Fc region are expected to be concentrated to the liver, which may be useful in treatment of cancer limited to the liver. A more preferred method is to use a multiple cytokine fusion protein that is further fused to a targeting agent such as an antibody. In particular, the antibodies KS-1/4 and 14.18 are directed against tumor-specific antigens (Varki N M et al., Cancer Res [1984] 44:681-7; Gillies et al., Journal of Immunological Methods 125:191 [1989]; U.S. Pat. Nos. 4,975,369 and 5,650,150). When using antibody-multiple cytokine fusion, it is often useful to investigate the type of tumor and choose an antibody directed against an antigen that is likely to be present on that type of tumor. For example, it may be useful to characterize the tumor by FACS analysis, Western blot, examination of the tumor's DNA, or simply identifying the type of the tumor cell. Such methods of tumor characterization are well known to those skilled in the art of tumor characterization, such as oncologists and tumor biologists. It is also possible to target multiple cytokine fusion proteins by a variety of other means, such as fusion to specific ligands or receptor moieties, fusion to peptide aptamers with pre-selected binding activities, chemical conjugation to small molecules with localizing characteristics, and so on. These targeting methods may also be used for treatment of other diseases, such as infections.

Treatment of Cancer and Other Cellular Disorders by Gene Therapy

The nucleic acids of the invention may be used as gene therapy agents for treatment of cancer and other diseases in which it is desirable to target the immune system to a specific cell type. For example, cancer cells are withdrawn from a human or animal, one or more nucleic acids encoding a multiple cytokine fusion protein are transfected into the cancer cells, and the cancer cells are then reintroduced into the human or animal. Alternatively, the DNA may be introduced into the cancer cell in situ. The human or animal then mounts an immune response to the cancer cells, which may cure or lessen the severity of the cancer. A multiple cytokine gene fusion, coupled to appropriate regulatory elements to promote expression in mammalian cells, may be transfected into the cancer cells by any of a variety of techniques, include the calcium phosphate method, a 'gene gun', adenovirus vectors, cationic liposomes, retroviral vectors, or any other efficient transfection method. The nucleic acid may encode a multiple cytokine fusion protein that is further fused to other moieties.

Anti-cancer gene therapy with a nucleic acid expressing a fusion of more than one fused cytokine, may be combined with other cancer treatments, such as treatments that may augment the immune-stimulating properties of the fused cytokine protein. For example, the nucleic acid of the invention may also express other protein moieties that may aid in the development of an immune response to antigens expressed by the cancer cells, or may be co-transfected with other nucleic acids expressing such protein moieties. In particular, nucleic acids expressing the B7 costimulatory surface protein may be cotransfected into the cancer cells [Robinson et al., U.S. Pat. No. 5,738,852]. Transfection of cancer cells with a nucleic acid expressing multiple cytokine fusion may also be accompanied by treatment with an antibody or immunocytokine that targets the cancer cells [Lode et al. (1998) Proc. Nat. Acad. Sci. 95:2475]. Transfection of cancer cells with a nucleic acid expressing multiple cytokine fusion may also be accompanied by treatment with an angiogenesis blocker [Lode et al. (1999) Proc. Nat Acad. Sci. 9:1591].

Therapies using additional immune stimulators and/or angiogenesis blockers may also be combined with systemic treatment with multiple cytokine fusion proteins. An advantage of co-treatment with additional immune stimulators or angiogenesis blockers is that these treatments, unlike DNA-damaging agents and cell-cycle blockers, do not kill immune cells that may be dividing due to stimulation by the multiple cytokine fusion protein.

A preferred embodiment of this gene therapy method is to introduce one or more nucleic acids encoding IL-12 and a second cytokine into cancer cells, and then reintroduce the cancer cells into the human or animal. The second cytokine is preferably IL-2 or GM-CSF.

The present invention provides novel vaccine compositions and methods of adjuvantation of vaccines intended to provide a protective cell-mediated immune response in vaccinated host mammals against certain pathogens, using as an adjuvant two or more cytokines that have been fused. For example, if a Th1 immune response is desired, multiple Th1-promoting cytokines may be fused and the resulting fusion protein administered to an animal in combination with an antigen.

In particular, IL-12 and IL-2 may be fused and administered with an antigen. Alternatively, IL-12 and IL-2 may be further fused to an antigenic protein itself and used to stimulate an immune response. In this case, the invention is directed to vaccines that rely on the host's cell-mediated immunity, i. e. the elicitation of cytotoxic T lymphocytes and activated phagocytes to provide protection against infection by a particular pathogen. It is especially useful to perform vaccinations with fusion proteins comprising IL-12, IL-2, and the antigen, as this combination directs a Th1 response against the antigen. Conventional adjuvants used in humans, such as alum, tend to induce a Th2 response.

If a Th2 immune response is desired, fused combinations of Th2-promoting cytokines may be used. For example, it may be useful to fuse IL-4 and IL-10 to form a single molecule, and the resulting fusion protein used as an adjuvant. In particular, if it is desired to recruit dendritic cells in an animal, fused combinations of IL-4 and GM-CSF may be further fused with either an Fc region to promote binding to antigen-presenting cells, or further fused to an antibody capable of directing the fused cytokines to a target tissue such as a tumor.

The present invention also provides novel therapeutic compositions and methods of adjuvanting intended to provide a synergistic effect with certain therapeutic compositions, including so-called 'cancer vaccines,' which may include a selected antigen occurring on a cancer cell. For example, a protein comprising two or more fused cytokines may be administered directly by an appropriate route, along with appropriately treated cancer cells.

EXAMPLES

Example 1

Construction of Gene Fusions Capable of Expressing Cytokine-Cytokine Fusion Proteins To create multifunctional proteins having a plurality of cytokines, gene fusions between IL-12's p40 and IL-2, and between IL-12's p40 and GM-CSF were synthesized. In addition, the coding sequence for mature murine p35 (SEQ ID NO:1) was fused to a promoter and leader sequence that allow high levels of expression and efficient secretion. Coding sequences of murine p40-IL-2 and p40-GM-CSF are shown in SEQ ID NO:2 and SEQ ID NO:3, respectively. A human p40-IL-2 fusion was also constructed (SEQ ID NO:4). Fusions of a mouse Fc region of IgG2a to mouse p35 (SEQ ID NO:5) and of human p35 to a human Fc region of IgG1 (SEQ ID NO:6) were constructed, using expression plasmids previously disclosed (Lo et al. Protein Engineering 11:495-500 [1998]; Lo et al., U.S. Pat. No. 5,726,087).

Fusion of mature mouse and human p35 to the C-terminus of the KS-1/4 antibody heavy chain is described by Gillies et al. (J. Immunology [1998] 160:6195-6203). Fusions of mature mouse and human p35 to the C-terminus of the 14.18 antibody heavy chain were constructed in an analogous manner (PCT International Publication WO99/29732).

The type of strategy discussed here to fuse p40 to IL-2 and to GM-CSF is generally applicable to the fusion of two or more cytokines. Specifically, the coding sequence of the most N-terminal moiety comprises a signal sequence for secretion, while the C-terminal moieties does not require a signal sequence. In some circumstances, it may be useful to place a coding sequence for a short peptide linker, preferably 10-15 amino acids long and rich in glycine and serine, between the coding sequences for the two cytokines. The DNA manipulations involved in generating all such types of fusions are within the level of skill in the art.

For example, details of the construction of a fusion between the murine IL-12 p40 subunit and murine IL-2 were as follows. Full length cDNA of the p40 subunit of murine IL-12 was cloned by PCR from mouse spleen cells activated with Concavalin A (5 μg/ml in culture medium for 3 days). The forward primer had the sequence AA GCT AGC ACC ATG TGT CCT CAG AAG CTA ACC (SEQ ID NO:7), in which a NheI site GCTAGC (residues 3-8 of SEQ ID NO:7) was placed upstream of the translation initiation codon ATG, and the reverse primer had the sequence CTC GAG CTA GGA TCG GAC CCT GCA GGG (SEQ ID NO:8), in which an XhoI site CTCGAG (residues 1-6 of SEQ ID NO:8) was placed immediately downstream of the translation stop codon TAG (anticodon CTA). After sequence verification, the NheI-XhoI fragment containing the mu-p40 cDNA with its native leader was ligated to the XbaI-XhoI digested expression vector pdCs [Lo et al. (1998) Protein Engineering 11:495-500]. The restriction sites NheI and XbaI have compatible sticky ends, and NheI site was used for the cloning of mu-p40 because mu-p40 has an internal XbaI site.

For the construction of DNA encoding mu-p40-muIL-2, an oligonucleotide linker was used to join the mu-p40 DNA via its PstI site (C TGC AG) to a SmaI-XhoI fragment containing the cDNA of mature murine IL-2. The DNA sequence at the junction of the fusion protein was C TGC AGG GTC CGA TCC CCG GGT AAA GCA CCC (SEQ ID NO:9), where C TGC AG (residues 1-6 of SEQ ID NO:9) is the PstI site, C CCG GG (residues 15-20 of SEQ ID NO:9) is the SmaI site, TCC is the C-terminal amino acid residue of murine p40, and GCA is the N-terminal residue of mature murine IL-2.

The DNA encoding single-chain muIL12-muGMCSF was derived from the DNA construct encoding single-chain muIL12-muIL2 above by replacing the muIL2 cDNA by the muGMCSF cDNA at the SmaI site. The DNA sequence at the junction of single-chain muIL12 and muGMCSF was C TGC AGG GTC CGA TCC CCG GGA AAA GCA (SEQ ID NO:10), where C TGC AG (residues 1-6 of SEQ ID NO:10) is the PstI site, C CCG GG (residues 17-22 of SEQ ID NO: 10) is the SmaI site, TCC is the C-terminal amino acid residue of murine p40, and GCA is the N-terminal residue of mature murine GMCSF.

Example 2

Expression of IL-12Fusion Proteins

IL-12-IL-2 fusion proteins were expressed as follows. Different combinations of the individual vectors encoding p40 fusions and vectors encoding proteins comprising p35 were co-transfected into human 293 epidermal carcinoma cells for transient expression of fusion proteins. DNA was purified using preparative kits (Wizard, Promega Inc.), ethanol-precipitated for sterilization and resuspended in sterile water.

For expression of biologically active IL-12 fusion protein heterodimers, different combinations of the individual vectors encoding fusion and non-fusion forms of the subunits were transiently expressed by co-transfection of human 293 epidermal carcinoma cells. DNA was purified using preparative kits (Wizard, Promega Inc.), ethanol precipitated for sterilization and resuspension in sterile water. Calcium phosphate precipitates were prepared by standard methods using 10 μg of DNA per ml (5 μg of each when two plasmids were co-transfected) and 0.5 ml/plate were added to cultures of 293 growing in 60 mm plates at approximately 70% confluency (MOLECULAR CLONING: A LABORATORY MANUAL, 2nd Ed., Sambrook, Fritsch and Maniatis, eds., Cold Spring Harbor Laboratory Press, 1989). After 16 hr, the medium containing the precipitate was removed and replaced with fresh medium. After 3 days, the supernatant was removed and analyzed for production of transfected gene expression by ELISA, biological determination of IL12 activity, or immunoprecipitation and analysis on SDS gels of radioactively labeled proteins. For labeling, medium without methionine was used to replace the growth medium on the second day of culture and $^{35}$S-methionine (100 μCi/ml) was added. After an additional 16 hr incubation, the media was harvested, clarified by centrifugation (5 min at 13,000 rpm in a table top microcentrifuge) and incubated with protein A Sepharose beads (10 μl of bead volume per ml of culture supernatant). After 1 hr at room temperature, the beads were washed by repeated centrifugation and resuspension in PBS buffer containing 1% Nonidet-P40 (NP-40). The final pellet was resuspended in SDS-containing gel buffer and boiled for 2 min. After removing the beads by centrifugation, the supernatant was divided into two aliquots. Reducing agent (5% 2-mercaptoethanol) was added to one sample and both samples were boiled for 5 min prior to loading on an SDS polyacrylamide gel. After electrophoresis the gel was exposed to X-ray film (autoradiography).

Transfections using the following expression plasmids were performed: mu.p35 plus mu.p40-IL-2, KS-1/4-mu.p35 plus mu.p40, KS-1/4-mu.p35 plus mu.p40-IL-2, 14.18-mu.p35 plus mu.p40-IL-2, hu.Fc-.p35 plus hu.p40-IL-2, KS-1/4-hu.p35 plus hu.p40-IL-2, and 14.18-hu.p35 plus hu.p40-IL-2, where "mu" refers to murine proteins and "hu" refers to human proteins.

When cells were metabolically labeled with $^{35}$S-methionine and secreted proteins examined by reducing SDS gel electrophoresis and autoradiography, high level expression was observed in each case. Molecular weights of reduced fusion proteins were predicted based on the molecular weights of component proteins, as follows: p35 of IL-12, 35 kD; p40 of IL-12, 40 kD; IL-2, 16 kD; Fc, 32 kD; Ig heavy chain, 55 kD; and Ig light chain, 28 kD. Proteins migrating with approximately the predicted molecular weights were observed.

Stably transfected cell lines expressing multiple cytokine fusion proteins were also isolated. In the case of heterodimeric constructs, IL-12 p40-IL-2 or IL-12 p40-GM-CSF fusion protein encoding expression vectors as described earlier for the IL-12 p40 subunit alone (Gillies et al. [1998] J. Immunol. 160: 6195-62030). Transfected cell lines expressing the p40 fusion proteins were transfected a second time with expression vectors encoding either the IL-12 p35 subunit, an Fc-p35 fusion protein or an antibody-p35 fusion protein expression vector as described (Gillies et al. [1998] J. Immunol. 160: 6195-62030).

Supernatant from stably transfected cells expressing human Fc-IL-12-IL-2 (i.e. expressing KS-p35 and p40-IL-2) was collected and the products were purified by binding to and elution from protein A Sepharose according to the manufacturer's procedures (Repligen, Needham, Mass.). The pure proteins were assayed by ELISA for IL-12 and IL-2 content. The results showed that the individual cytokine contents were approximately 4-fold different by mass which correlates to the 4-fold difference in molecular weight between IL-12 and IL-2. Similarly, assay of the products of transfected cells expressing human KS-IL-12-IL-2 by ELISA for IL-12 and IL-2 levels gave similar values of IL-12 and IL-2. Thus, within the accuracy of the ELISAs, the measured values indicate that IL-12 and IL-2 are being produced in about a 1:1 molar ratio. The same results were obtained with the IL-12-GM-CSF fusion proteins made either with the Fc or whole antibody.

Example 3

Synergistic Activity of Fusion Proteins in an IFN-γ Induction Assay

Biological activity of IL-12-IL-2 fusion proteins was measured in an IFN-γ induction assay using either resting or mitogen-activated human peripheral blood mononuclear cells (PBMCs) from human volunteers (FIG. 6). IFN-γ production was measured by ELISA.

Human peripheral blood mononuclear cells (PBMCs) were obtained from healthy volunteers and were purified by centrifugation on a Ficoll-Hypaque (Pharmacia) gradient (1700 rpm for 20 min). The "buffy" coat containing the PBMC was diluted with serum-free culture medium (SF-RPMI) to a volume of 50 ml and collected by centrifugation at 1500 rpm for 5 min. After gradient centrifugation, cells were resuspended in cell culture medium containing 10% fetal bovine serum (RPMI-10) with or without phytohemagglutinin (PHA; 10 μg/ml) at a density of $5\times10^6$ cells/ml and were cultured for 3 days at 37° C. in a humidified $CO_2$ incubator. The cells were collected by centrifugation, washed three times with an equal volume of SF-RPMI and resuspended in fresh RPMI-10 ($1\times10^6$ cells/ml). Aliquots (100 μl) were dispensed into the wells of multiple 96-well plates to give a final cell number of $10^5$ per well. Test samples from culture medium were serially diluted in fresh culture medium and added to wells of the 96-well plate. Control wells received IL-12 (FIG. 6A) or an equimolar mixture of commercial IL-2 and IL-12 (FIG. 6B; cytokines purchased from R & D Systems). The plates were incubated for 48 hr at 37° C. in a $CO_2$ incubator at which time aliquots (20 μl) were removed for analysis of IFN-γ concentration by ELISA, following the instructions of the manufacturer (Endogen, Inc., Woburn, Mass. USA).

Figure 6A:
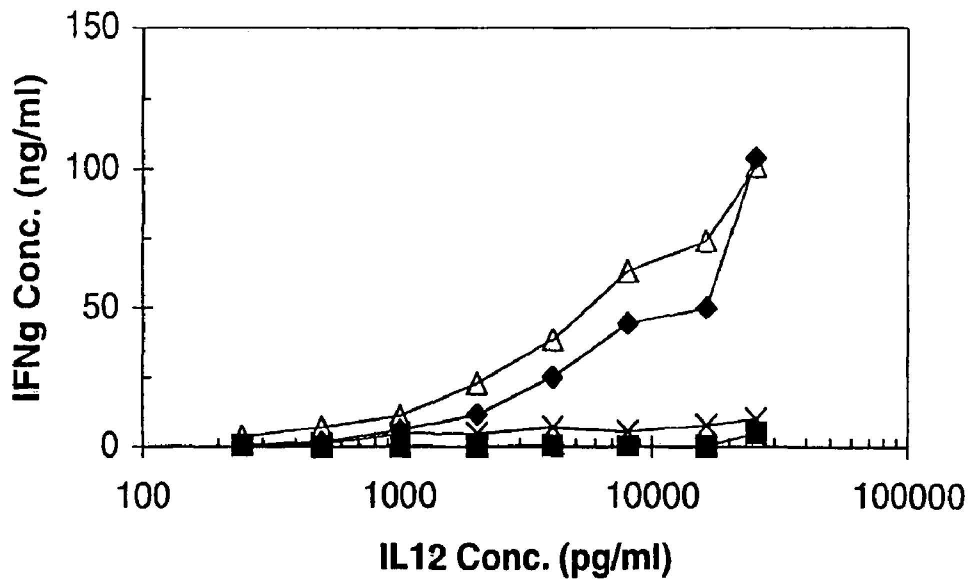
FIGS. 6A and 6B show the synergy between IL-12 and IL-2 in the induction of IFN-γ by human peripheral blood mononuclear cells (PBMCs) in response to the separate cytokines or fusion proteins.
Figure 6B:
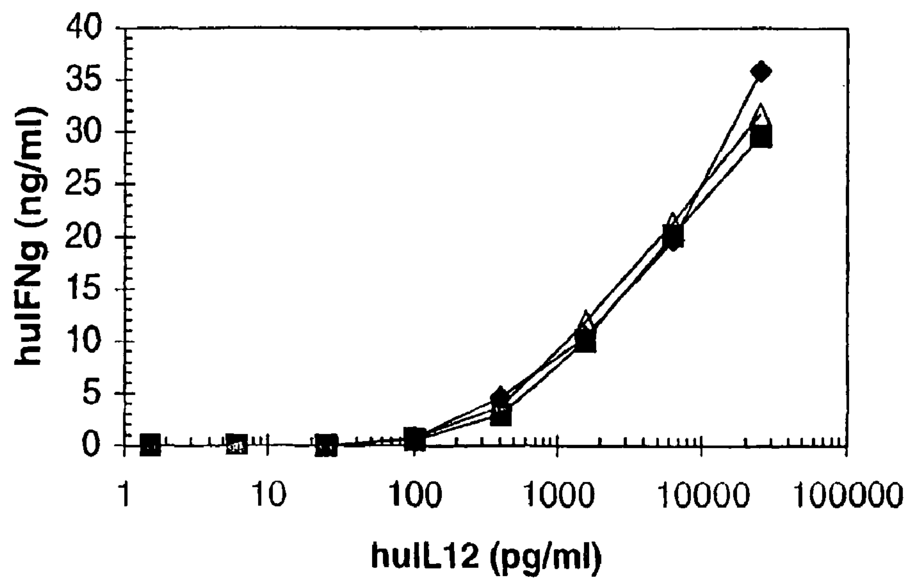

In FIG. 6A, the activities of the human IL-12-IL-2 fusion protein were compared with IL-12 alone. The results illustrate that IL-12 alone induced IFN-γ to moderate levels, while the IL-12-IL-2 fusion protein strongly induced IFN-γ synthesis. Since IL-2 is also known to be insufficient for IFN-γ synthesis, these results indicate that the IL-12 and IL-2 moieties are both functional within the fusion protein and function synergistically.

Next, the activities of an Fc-IL-12-IL-2 fusion protein, a KS-IL-12-IL-2 fusion protein, and a mixture consisting of 1:1 molar ratio of IL-12 to IL-2 were compared for their ability to induce IFN-γ. The results in FIG. 6B indicate that the Fc-IL-12-IL-2 fusion protein and KS-IL-12-IL-2 fusion protein have about the same activity as an equimolar mixture of IL-12 and IL-2. The same results were obtained when the mouse forms of IL-2 and IL-12, constructed in the manner just described in Example 1 for the human forms, were used for the construction of fusion proteins.

Example 4

IL-2 and IL-12 Bioactivity of IL-12-IL-2 Fusion Proteins

Figure 7:
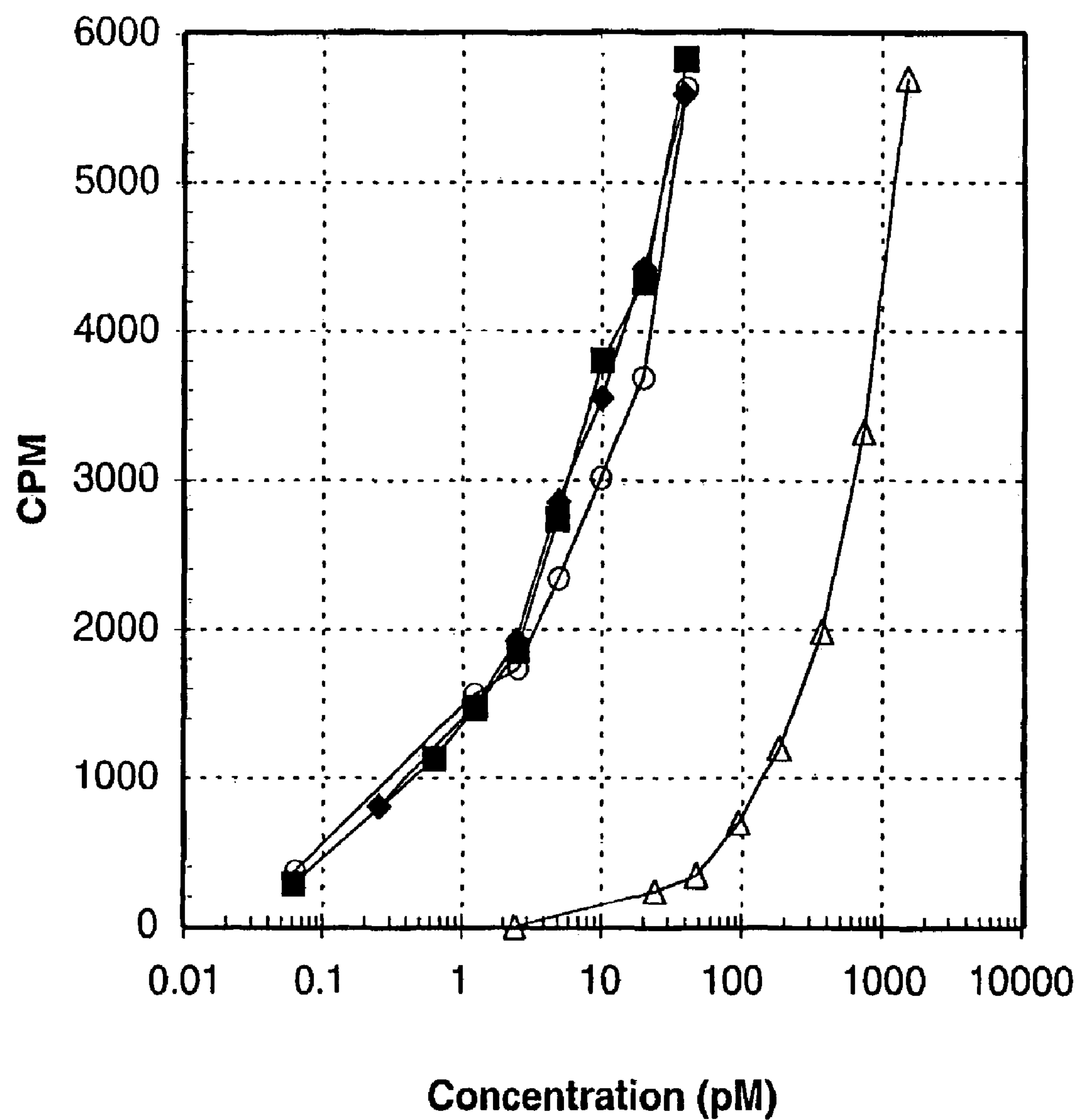
FIG. 7 shows a typical IL-12 bioassay that separately measures activity of a fusion protein and compares it to that of a non-fused IL-12 molecule. What is depicted is the stimulation of $^3$H-thymidine uptake of human PBMCs in response to murine IL-12 (white circles), to a mixture of murine IL-12 plus IL-2 added in a 1:1 molar ratio (black squares), to murine IL-2 (white triangles), and to an antibody-murine IL-12-IL-2 fusion protein (black diamonds). The X axis indicates the concentration (pM) of monomeric cytokine(s), whether present as an intact protein or as a fusion protein; the y-axis indicates cpm of tritiated thymidine incorporation.

The activities of IL-2 and IL-12 in the fusion proteins were compared to the free cytokines in proliferation-based assays. The activity of a murine antibody 14.18-IL-12-IL-2 molecule was tested in a typical IL-12 proliferation assay. Human PBMCs were obtained from volunteers and cultured with 5 micrograms/ml of phytohemagglutinin-P for three days, washed with Hank's HBSS, and plated into microtiter plates at $10^5$ cells per well, according to a standard procedure (Gately, M. K., Chizzonite, R., and Presky, D. H. *Current Protocols in Immunology [*1995] pp. 6.16.1-6.16.15). Cells were incubated in the presence of various test proteins for 48 hours, and 0.3 microCuries of $^3$H-thymidine were added ten hours before determining levels of radioactive incorporation. IL-12 and an equimolar mixture of IL-12 and IL-2 stimulated incorporation of $^3$H-thymidine into cells in a dose-dependent manner, and the 14.18-IL-12-IL-2 fusion protein was about equally effective in stimulating incorporation of $^3$H-thymidine. IL-2 stimulated incorporation of $^3$H-thymidine only at higher molar concentrations, indicating that the observed incorporation of $^3$H-thymidine stimulated by the 14.18-IL-12-IL-2 fusion protein is due primarily to its IL-12 activity. Results are shown in FIG. 7.

Figure 8:
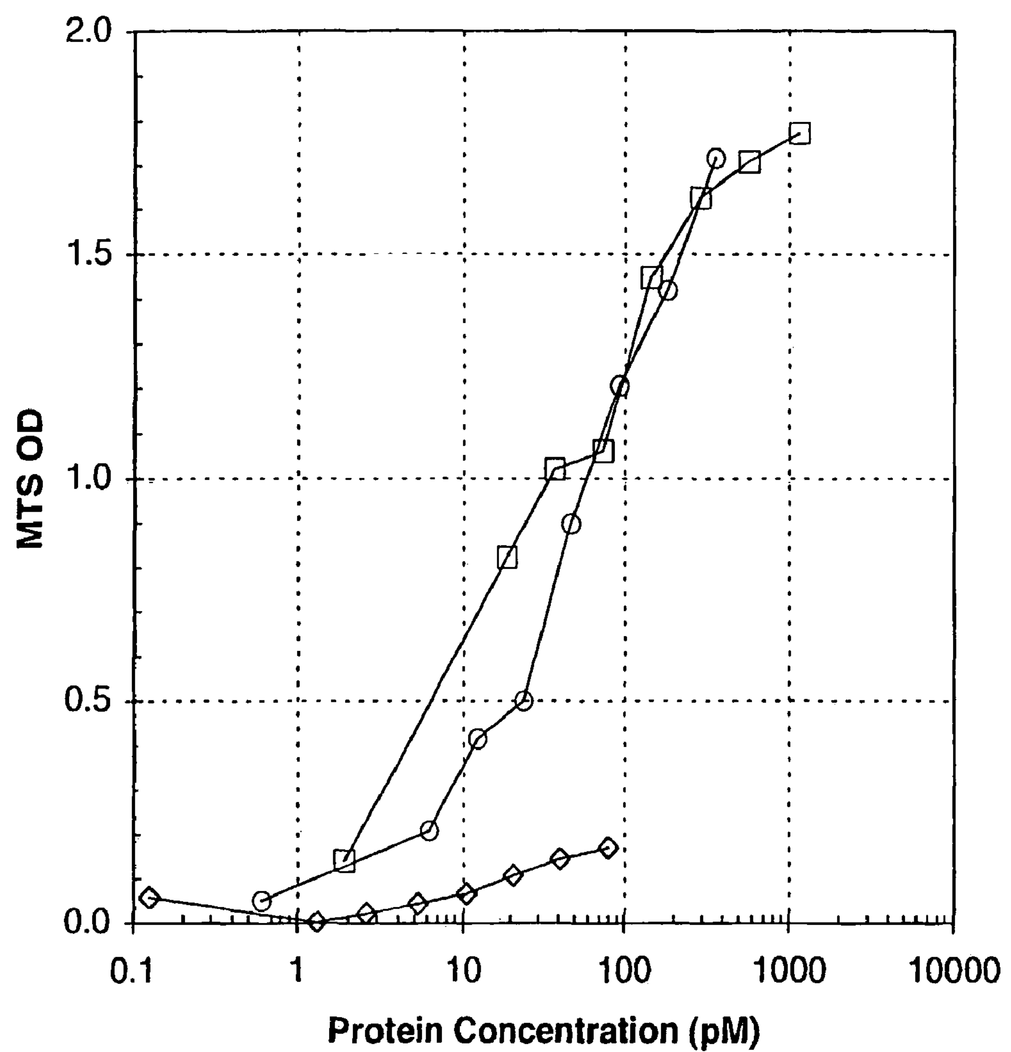
FIG. 8 shows a standard IL-2 bioactivity assay. The graph shows the stimulation of mouse CTLL cell proliferation, in response to murine IL-2 (circles), to an antibody-murine IL-12-IL-2 fusion protein (diamonds), and murine IL-12 (squares). The x axis indicates the concentration (pM) of monomeric cytokine(s), whether present as an intact protein or as a fusion protein. Cells were incubated in medium containing various amounts of cytokine or fusion protein for 48 hours, then assayed for viable cell number using the MTT/MTS assay. The y-axis indicates the absorbance at 490 nanometers in units of optical density (OD).

In addition, the biological activity of the IL-2 moiety was tested in a different cell proliferation assay, following a standard procedure (Davis, L. S., Lipsky, P. E., and Bottomly, K. *Current Protocols in Molecular Immunology [*1995] p. 6.3.1-6.3.7). The mouse CTLL-2 cell line depends on IL-2 for proliferation. The CTLL-2 cell line can also proliferate in response to IL-4, but is not responsive to IL-12. CTLL-2 cells in active log-phase growth were washed twice in medium lacking IL-2 and plated at about $1\times10^4$ cells per well in microtiter wells in the presence of various amounts of commercial murine IL-2, murine 14.18-IL-12-IL-2 fusion protein, or commercial murine IL-12, and grown for 48 hours. At the end of the growth period, the number of viable cells was quantitated using the MTT/MTS assay. FIG. 8 shows an experiment in which levels of IL-2, IL-12, or 14.18-IL-12-IL-2 fusion protein were varied. The results indicate that murine IL-2 and murine 14.18-IL-12-IL-2 fusion protein are about equally potent in stimulating proliferation, while increasing amounts of murine IL-12 caused no detectable stimulation of cell proliferation. This result indicates that the stimulation of CTLL-2 cell proliferation by 14.18-IL-12-IL-2 fusion protein is due to the IL-2 moiety and not the IL-12 moiety.

Example 5

Construction and Expression of Single-chain and Multiple Chain IL-12-IL-2 Fusion Proteins With and Without Antibody Moieties A single-chain murine IL-12-IL-2 fusion protein was constructed as follows. A p40-IL-2 coding sequence fusion was constructed by methods analogous to those used in construction of the human p40-IL-2 fusion in example 1. To connect the DNAs encoding the p35 and p40 subunits of IL-12 and generate a single coding sequence, a DNA encoding a linker was synthesized with an XhoI site at the 5' end and a BamHI site at the 3' end. The 5' end of the mature p40-IL-2 coding sequence was modified to introduce a restriction site, and then ligated to the 3' end of the linker. The 3' end of the murine p35 coding sequence was modified to generate a restriction site and ligated to the XhoI site of the linker. The cDNAs encoding single-chain muIL12 and mu-p40-muIL2, described in Example 1, were combined by using a convenient restriction site in p40, to give a third DNA construct encoding single-chain muIL12-muIL2. These steps were carried out using various vectors and DNA fragment isolations as needed. The sequence of the resulting murine p35-linker-p40-IL-2 coding region is SEQ ID NO: 11.

At the same time, a corresponding single-chain murine IL-12 coding sequence was constructed by corresponding methods. The coding sequence is SEQ ID NO:12.

In addition, we further constructed a DNA sequence that encodes a murine IgG2a Fc region fused to the N-terminus of p35-linker-p40-IL-2. The coding sequence is SEQ ID NO:13.

Cultured 293 cells were transfected with expression plasmids encoding the murine single-chain Fc-IL-12-IL-2 and Fc-IL-12 proteins. Expression of fusion proteins was assayed as described in Example 2. Fc fusion proteins were purified by their binding to protein A Sepharose, and high levels of expression of Fc-IL-12-IL-2 and Fc-IL-12 were observed. Proteins were synthesized intact, as inferred by the apparent molecular weights from migration on SDS gels: Fc-IL-12-IL-2, 123 kD; and Fc-IL-12, 107 kD.

The KS-scIL12-IL2 fusion protein described in Example 1 is a tetramer with two different polypeptide chains: the KS-1/4 light chain and the KS-1/4 heavy chain with the scIL12-IL2 moiety at the C-terminus. To investigate which sites on an antibody molecule are suitable for attachment of cytokine moieties, a second fusion protein was constructed in which the KS-1/4 antibody, IL-12, and IL-2 moieties were in a configuration distinct from the KS-IL12-IL2 configuration in Example 1. This second protein was tetrameric and consisted of two different polypeptides. One polypeptide consisted of the light chain of the KS-1/4 antibody. The other polypeptide consists of a single-chain muIL12 fused to the mature N-terminus of the heavy chain of the KS 1/4 antibody, followed by murine IL-2 at the carboxyl terminus of the heavy chain.

The cDNA encoding the p35 subunit of murine IL-12 was cloned by PCR from mouse spleen cells activated with Concanavalin A (5 μg/ml in culture medium for 3 days). The forward primer has the sequence AAGCTT GCTAGCAGC ATG TGT CAA TCA CGC TAC (SEQ ID NO:14), where a HindIII site AAGCTT (residues 1-6 of SEQ ID NO:14) is placed upstream of the translation initiation codon ATG, and the reverse primer has the sequence CTCGAG CTT TCA GGC GGA GCT CAG ATA GCC (SEQ ID NO:15), where an XhoI site CTCGAG (residues 1-6 of SEQ ID NO:15) is placed downstream of the translation stop codon TGA (anticodon TCA).

The DNA encoding the single-chain IL-12 comprises of the mup35 DNA joined to oligonucleotides encoding a linker rich in glycine and serine residues, followed by mup40 DNA. The resultant construct has the following sequence at the oligonucleotide junction:

```
             Ser Ser Gly Gly Ser Gly Gly Gly Gly Ser Gly Gly Gly Gly Ser Ala          (SEQ ID NO:17)
G AGC TCC GCG TCG AGC GGG GGC AGC GGG GGC GGA GGC AGC GGC GGG GGC GGA TCC GCC ATG     (SEQ ID NO:16)
```

where G AGC TC (residues 1-6 of SEQ ID NO: 16) is a SacI restriction site just upstream of the murine p35 translation stop codon, GCG encodes the C-terminal amino acid residue of murine p35, GGA TCC (residues 50-55 of SEQ ID NO:16) is a BamHI restriction site introduced to facilitate ligation, and ATG encodes the N-terminal residue of mature mu-p40.

The DNA encoding single-chain muIL12-KS Heavy chain-muGMCSF has the following sequence at the junction of mup40and the mature N-terminus of KS heavy chain:

```
                                                                                   (SEQ ID NO:19)
                     Pro Gly Ser Gly Gly Ser Gly Gly Gly Gly Ser Gly Gly Gly Gly Ser Leu Ser
                                                                                   (SEQ ID NO:18)
C TGC AGG GTC CGA TCC CCG GGA TCC GGA GGT TCA GGG GGC GGA GGT AGC GGC GGA GGG GGC TCC TTA AGC CAG
```

where C TGC AG (residues 1-6 of SEQ ID NO:18) is a PstI site just upstream of the murine p40 translation stop codon, TCC encodes the C-terminal amino acid residue of murine p40, and CAG encodes the N-terminal residue of mature KS heavy chain. The resultant DNA encoding single-chain muIL12-KS Heavy chain-muIL2 was then coexpressed with the KS light chain.

To further investigate which ends of an antibody molecule are available for the generation of fusion junctions and to investigate how many distinct polypeptides can be assembled into a multiple cytokine fusion protein, a third protein containing KS-1/4, IL-12, and IL-2, namely IL12-KS(Light chain)+KS(heavy chain)-IL2, was expressed and tested for activity. This fusion protein is hexameric and comprises three different polypeptides. One polypeptide consists of the murine p35 fused to the light chain of the KS1/4 antibody. A second polypeptide consists of the heavy chain of the KS1/4 antibody fused to human IL-2 [Gillies et al. (1992) Proc. Natl. Acad. Sci. 89:1428], and a third polypeptide is the murine p40. Upon expression, two light chains and two heavy chains are disulphide bonded to form the tetrameric antibody-cytokine structure. In addition, the p35 at the N-terminus of the light chain also is disulphide bonded with the p40.

The DNA encoding the mup35-KS light chain has the following sequence at the junction:

```
            Ser Ser Gly Gly Ser Gly Gly Gly Gly Ser Gly Gly Gly Gly Ser Leu Ser     (SEQ ID NO:21)
G AGC TCC GCG TCG AGC GGG GGC AGC GGG GGC GGA GGC AGC GGC GGG GGC GGA TCC TTA AGC GAG  (SEQ ID NO:20)
```

where G AGC TC (residues 1-6 of SEQ ID NO:20) is a SacI restriction site just upstream of the murine p35 translation stop codon, GCG encodes the C-terminal amino acid residue of murine p35, GGA TCC (residues 50-55 of SEQ ID NO:20) is a BamHI restriction site introduced to facilitate ligation, and GAG encodes the N-terminal amino acid residue of the light chain.

For expression of this hexameric fusion protein, a murine p40-expressing cell line was generated by transfection with an expression vector containing a neomycin resistance gene and selection by G418. The murine p40-expressing cell line was then transfected with an expression vector containing both the light chain and heavy chain transcription units and a dihydrofolate reductase selection marker, which allowed selection by methotrexate [Gillies et al. (1998) 3. Immunol. 160:6195].

Example 6

Activity of Murine Single-chain IL-12-IL-2Fusion Proteins

The same methods used in Example 4 were used to test the activity of murine single-chain IL-12-IL-2 produced by transient expression. The amount of each cytokine in the cell culture supernatant was first determined by ELISA and used to set up a dose-response curve. The activities closely corresponded to what was found with the Fc and antibody IL-12-IL-2 fusion proteins and described above.

Figure 9:
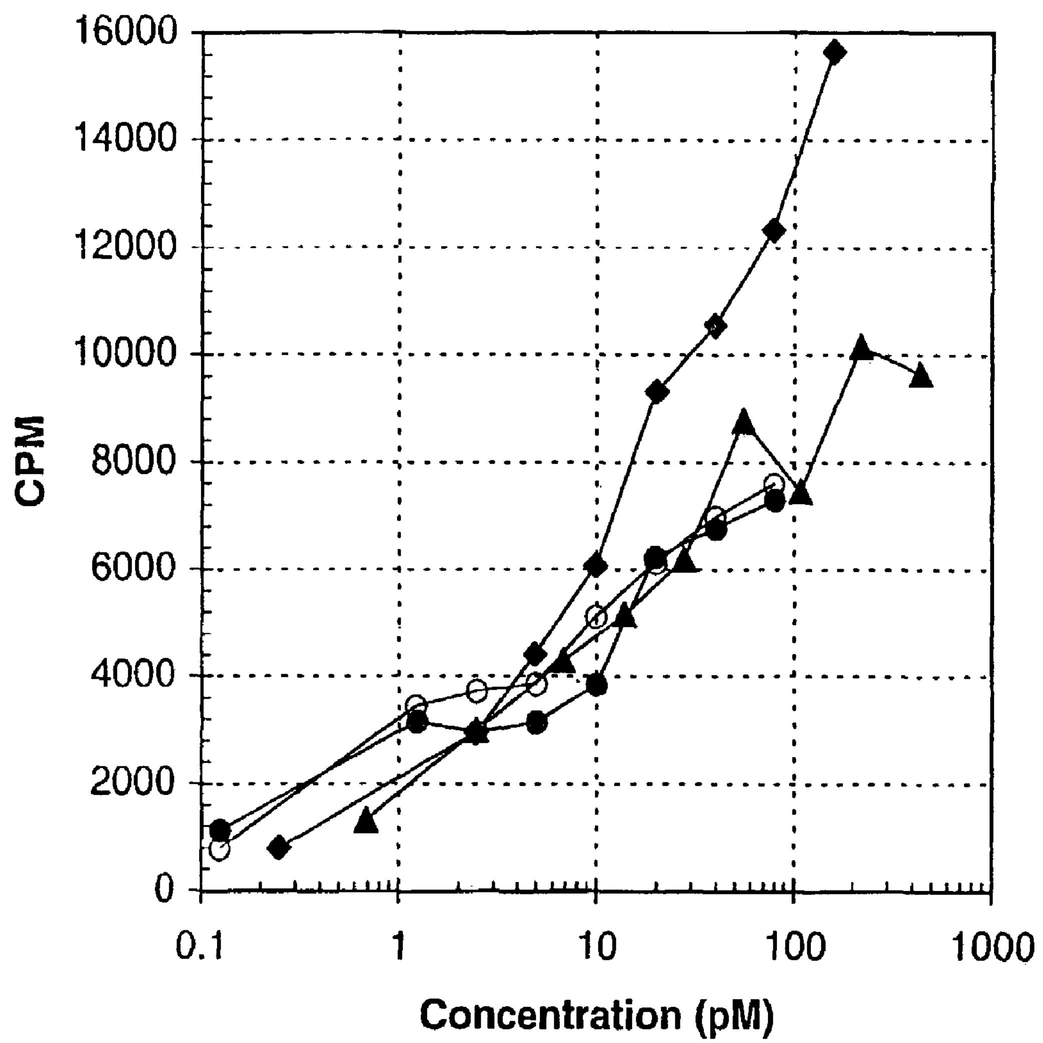
FIG. 9 shows the stimulation of $^3$H-thymidine uptake by human PBMCs in response to murine IL-12 (white circles), to a mixture of murine IL-12 plus IL-2 added in a 1:1 molar ratio (black circles), to a murine Fc-single-chain-IL-12-IL-2 fusion protein (black triangles), and to murine single-chain IL-12 fused to murine IL-2 (black diamonds). The x axis indicates the concentration (pM) of monomeric cytokine(s), whether present as an intact protein or as a fusion protein; the y-axis indicates cpm of tritiated thymidine incorporation.

Specifically, the IL-12 activity of a murine single-chain (sc) IL-12-IL-2 and murine Fc-scIL-12-IL-2 molecules were tested in the human PBMC cell proliferation assay described in Example 4. IL-12 and an equimolar mixture of IL-12 and IL-2 stimulated incorporation of $^3$H-thymidine into cells in a dose-dependent manner. On a per mole basis, both scIL-12-IL-2 and Fc-scIL-12-IL-2 fusion proteins were about as effective as IL-12 in stimulating incorporation of $^3$H-thymidine (FIG. 9). As described in Example 4, IL-2 stimulates incorporation of $^3$H-thymidine only at a much higher molar concentrations, indicating that the observed incorporation of $^3$H-thymidine stimulated by the scIL-12-IL-2 fusion proteins is due primarily to their IL-12 activity.

In addition, the biological activity of the IL-2 moiety in the scIL-12-IL-2 fusion proteins was tested in a cell based assay, and was found to be about the same as commercial IL-2 on a per mole basis, to within the accuracy of the assay. The biological activity of the IL-2 moiety was tested in the CTLL-2 cell proliferation assay, as described in Example 4. The results indicate that murine IL-2, murine scIL-12-IL-2, and murine Fc-IL-12-IL-2 fusion protein were about equally potent in stimulating proliferation. Murine IL-12 causes no detectable stimulation of CTLL-2 cell proliferation. These results indicate that the stimulation of CTLL-2 cell proliferation by scIL-12-IL-2 fusion proteins was due to the IL-2 moiety and not the IL-12 moiety.

The IL-12 and IL-2 activities of the Fc-IL12-IL2, IL12-KS-IL2, and IL12-KS(Light chain)+KS(Heavy chain)-IL2 proteins described in Example 5 were also tested in cell-based assays. Using the PBMC cell proliferation/tritiated thymidine incorporation assay, the Fc-IL12-IL2, IL12-KS-IL2, and IL12-KS(Light chain)+KS(Heavy chain)-IL2 proteins all showed potent IL-12 activity. Similarly, using the CTLL-2 cell proliferation assay, the Fc-IL12-IL2, IL12-KS-IL2, and IL12-KS(Light chain)+KS(Heavy chain)-IL2 proteins all showed potent IL-2 activity. In addition, in an ELISA, the IL12-KS-IL2 and IL12-KS(Light chain)+KS(Heavy chain)-IL2 proteins both bound tightly to the EpCAM antigen, even though the heavy and light chain V regions, respectively, are fused to other proteins at their N-termini.

Example 7

Activity of Murine IL-12-GM-CSF Fusion Proteins

Figure 10:
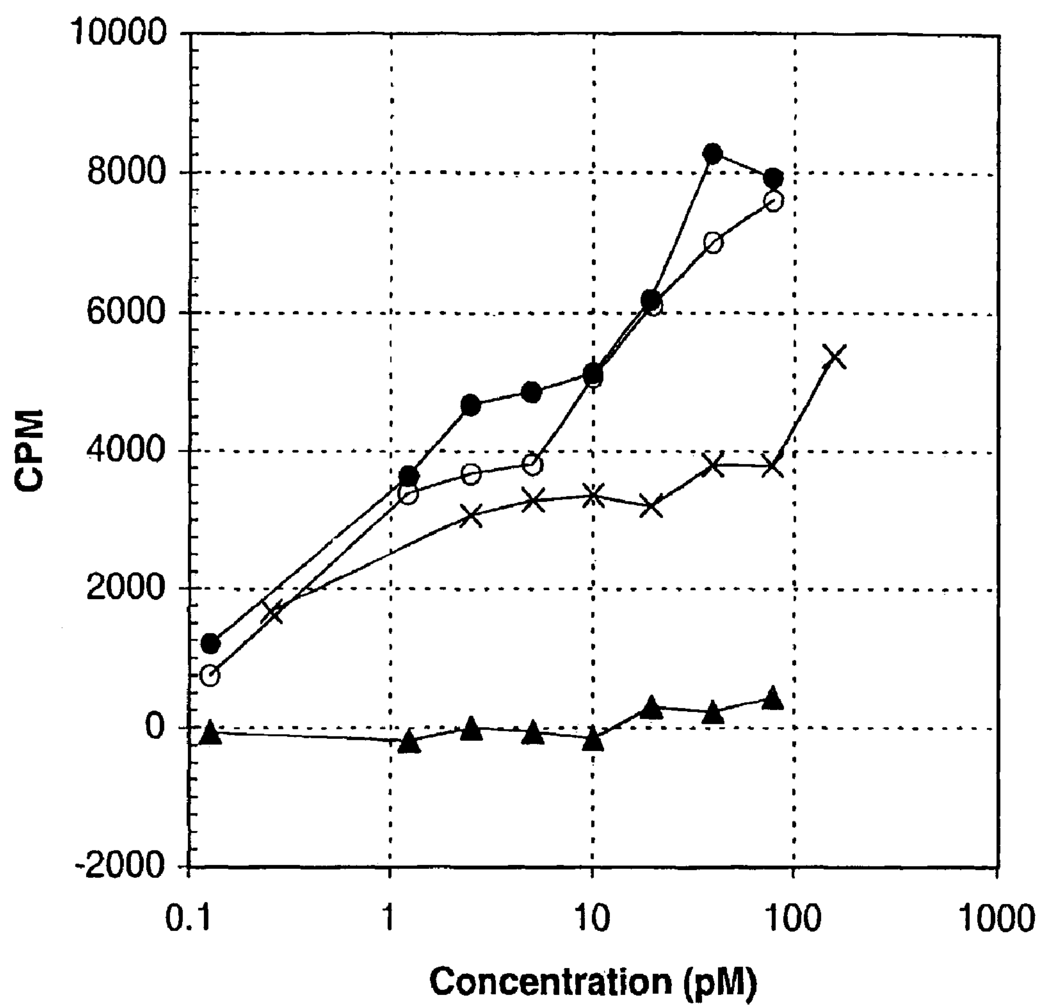
FIG. 10 shows the stimulation of $^3$H-thymidine uptake by human PBMCs in response to murine IL-12 (white circles), to a mixture of murine IL-12 plus GM-CSF added in a 1:1 molar ratio (black circles), to murine GM-CSF (black triangles), and to an murine Fc-murine IL-12-GM-CSF fusion protein (X's). The x axis indicates the concentration (pM) of monomeric cytokine(s), whether present as an intact protein or as a fusion protein; the y-axis indicates cpm of tritiated thymidine incorporation.

The IL-12 activity of a murine Fc-IL-12-GM-CSF molecule was tested in a cell proliferation assay (FIG. 10). Human PBMCs were obtained from three volunteers and cultured with 5 micrograms/ml phytohemagglutinin-P for three days, washed with Hank's HBSS, and plated into microtiter plates at $10^5$ cells per well, according to a standard procedure (Gately, M. K., Chizzonite, R., and Presky, D. H. *Current Protocols in Immunology [*1995] p. 6.16.1-6.16.15). Cells were incubated in the presence of various test proteins for 48 hours, and 0.3 microCuries of $^3$H-thymidine was added ten hours before determining levels of radioactive incorporation. IL-12 and an equimolar mixture of IL-12 and GM-CSF stimulated incorporation of $^3$H-thymidine into cells in a dose-dependent manner, and the 14.18-IL-12-GM-CSF fusion protein was about equally effective in stimulating incorporation of $^3$H-thymidine. GM-CSF did not stimulate incorporation of $^3$H-thymidine at the concentrations tested, indicating that the observed incorporation of $^3$H-thymidine stimulated by the 14.18-IL-12-GM-CSF fusion protein was due primarily to its IL-12 activity.

In addition, the biological activity of the GM-CSF moiety of various IL-12-Gm-CSF fusion proteins is tested in cell based assays. It is found that the GM-CSF moiety is active, with an activity per mole in the same general range as commercial GM-CSF. For example, the biological activity of the GM-CSF moiety is tested in a different cell proliferation assay, following a procedure known to those practiced in the art of molecular immunology (Cooper, S. C., and Broxmeyer, H. E. *Current Protocols in Molecular Immunology [*1996] p. 6.4.1-6.4.20). The mouse 32D(GM) cell line depends on GM-CSF for proliferation; this line has been adapted from the original 32D cell line, described by Cooper and Broxmeyer, to be particularly sensitive to GM-CSF (Faas et al., Eur. J.

Immunol. [1993] 23:1201-14). The 32D(GM) cell line is not responsive to IL-12. 32D(GM) cells in active log-phase growth are washed twice in medium lacking GM-CSF and plated at about $5\times10^3$ cells per well in microtiter wells in the presence of various amounts of commercial murine GM-CSF or murine IL-12-GM-CSF fusion protein and grown for 48 hours. 0.3 microCuries of $^3$H-thymidine are added sixteen hours before determining levels of radioactive incorporation. There is a dose responsive increase in incorporation of $^3$H-thymidine with increasing levels of IL-12-GM-CSF fusion protein, indicating that the GM-CSF moiety of the IL-12-GM-CSF fusion protein is active. Moreover, the GM-CSF biological activity of the fusion protein, calculated on a molar basis, is comparable to that of commercial murine GM-CSF.

Example 8

Treatment of Colon Carcinoma in an Immune-proficient Mammal with a Multiple Cytokine Fusion Protein To test whether a multiple cytokine-antibody fusion protein could be used to treat colon carcinoma in a mammal with an intact immune system, the following experiments were performed. CT26 is a colon carcinoma cell line derived from Balb/C mice. By standard genetic engineering techniques, this cell line was engineered to express the human epithelial cell adhesion molecule (EpCAM), which is the antigen recognized by the KS-1/4 antibody; these cells are termed CT26/KSA cells.

Balb/C mice were subcutaneously inoculated with $2\times10^6$ CT26/KSA cells. When tumors reached a volume of about 100-200 cubic millimeters, mice were randomized into three groups of 9 mice for further study. Beginning at day 0, tumor-bearing mice were treated with PBS, about 3.4 micrograms of KS-IL2 mixed with about 5.3 micrograms of KS-IL12, or about 6 micrograms of KS-IL2-IL12. These doses are designed to deliver an equal number of IL-12 and IL-2 molecules to each set of mice. Mice were injected intratumorally, once per day for five days. Tumor sizes were measured with calipers.

Figure 11:
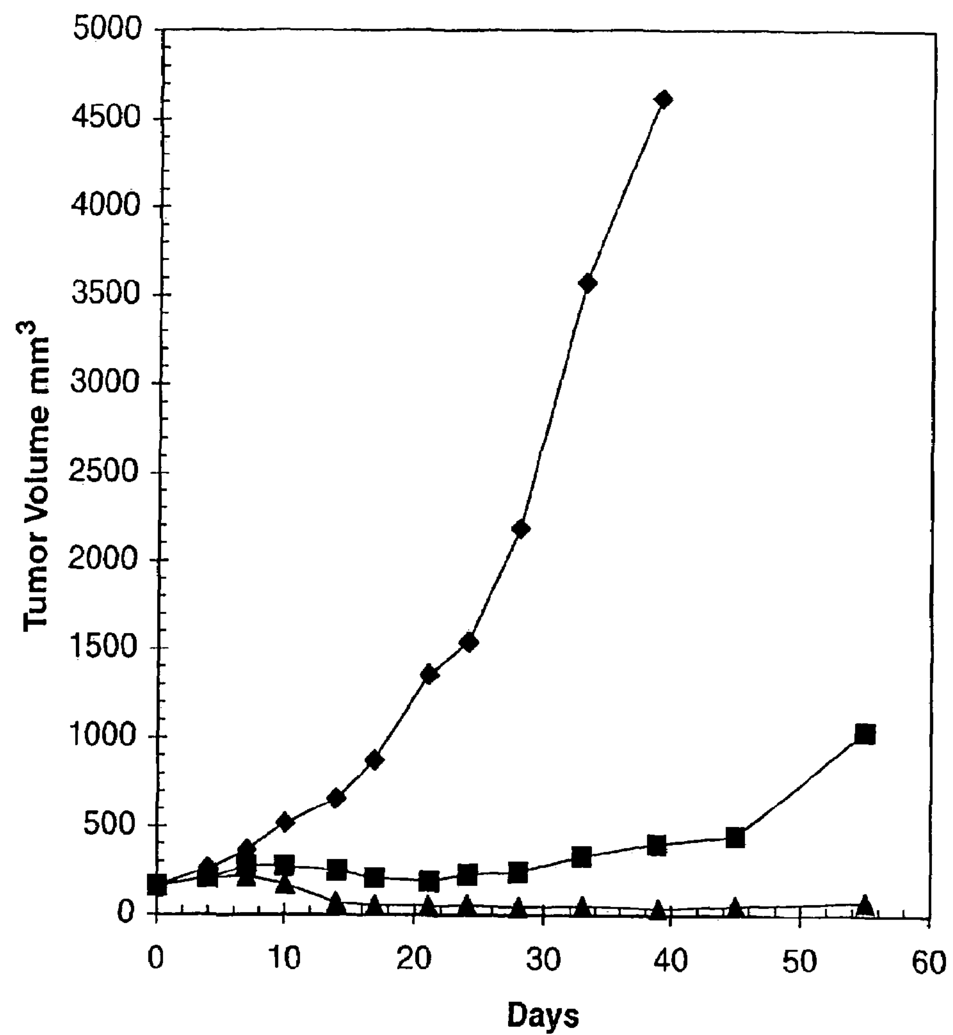
FIG. 11 shows the effect of antibody-cytokine-cytokine fusion protein treatment of Balb/C mice bearing subcutaneous tumors derived from CT26 colon carcinoma cells that were engineered to express human EpCAM, the antigen for KS-1/4. Black diamonds indicate average tumor volumes in mice that were injected with PBS as controls on days 0, 1, 2, 3, and 4. Triangles indicate average tumor volumes in mice treated with 6 micrograms of KS-IL-12-IL-2. Squares indicate average tumor volumes in mice treated with 3.4 micrograms of KS-IL2 and 5.3 micrograms of KS-IL12. Intratumoral injections were performed. The x-axis indicates the number of days elapsed following the first injection; the y-axis indicates the average tumor volume in cubic milliliters.

The results of one such experiment are shown in FIG. 11. In this experiment, KS-IL12-IL2 caused a profound inhibition of tumor growth. The mixture of KS-IL12 and KS-IL2 also caused a significant inhibition of tumor growth, but not as complete as KS-IL12-IL2. In the group of mice treated with KS-IL12-IL2, six of nine mice were apparently cured of their tumors: these six mice survived until day 93, when the experiment was terminated; and the tumors in these mice shrank and disappeared, so that no subcutaneous tumor could be detected from day 39 to day 93. The other three mice had tumors whose growth was delayed such that the tumor volumes exceeded 4,000 cubic millimeters only after day 87.

Of the mice treated with a mixture of KS-IL12 and KS-IL2, two mice were apparently cured of their subcutaneous tumors and survived until the end of the experiment. The tumors in the remaining seven mice did not disappear and eventually grew to volumes of 1,000 cubic millimeter (1 mouse) or greater than 4,000 cubic millimeters (6 mice).

The fact that KS-IL12-IL2 is more effective that an equimolar mixture of KS-IL12 and KS-IL2 is surprising. The doses in this experiment deliver about 15 picomoles of fusion protein per dose, which corresponds to about $9\times10^{12}$ molecules. At the start of treatment, each tumor has a volume of about 160 cubic millimeters, which corresponds to about 160 million cells. Each cell expresses about $10^6$ molecules of EpCAM, so there are about $1.6\times10^{14}$ EpCAM antigen molecules to which the KS antibody might bind. Thus, when KS-IL12 and KS-IL2 were mixed and injected into mice bearing such tumors, it is unlikely that these two immunocytokine fusion proteins competed with each other for antigen binding sites. Thus, the effective dose of IL-12 and IL-2 at the tumor site should have been at least as high for the mixture of KS-IL12 and KS-IL2 as for KS-IL12-IL2.

Example 9

Treatment of Colon Carcinoma in an Immunodeficient Mammal with a Multiple Cytokine Fusion Protein Many forms of cancer therapy have the effect of killing dividing cells, including cells of the immune system. As a result, cancer patients often become immunosuppressed. To address whether multiple cytokine fusion proteins can be used to treat a mammal with a suppressed immune system, SCID mice bearing CT26/KSA tumors were treated with KS-IL12-IL2, a mixture of KS-IL12 and KS-IL2, or PBS. SCID mice are deficient in both B cells and T cells and depend on branches of the innate immune system, such as NK cells, for their ability to fight infections.

Figure 12:
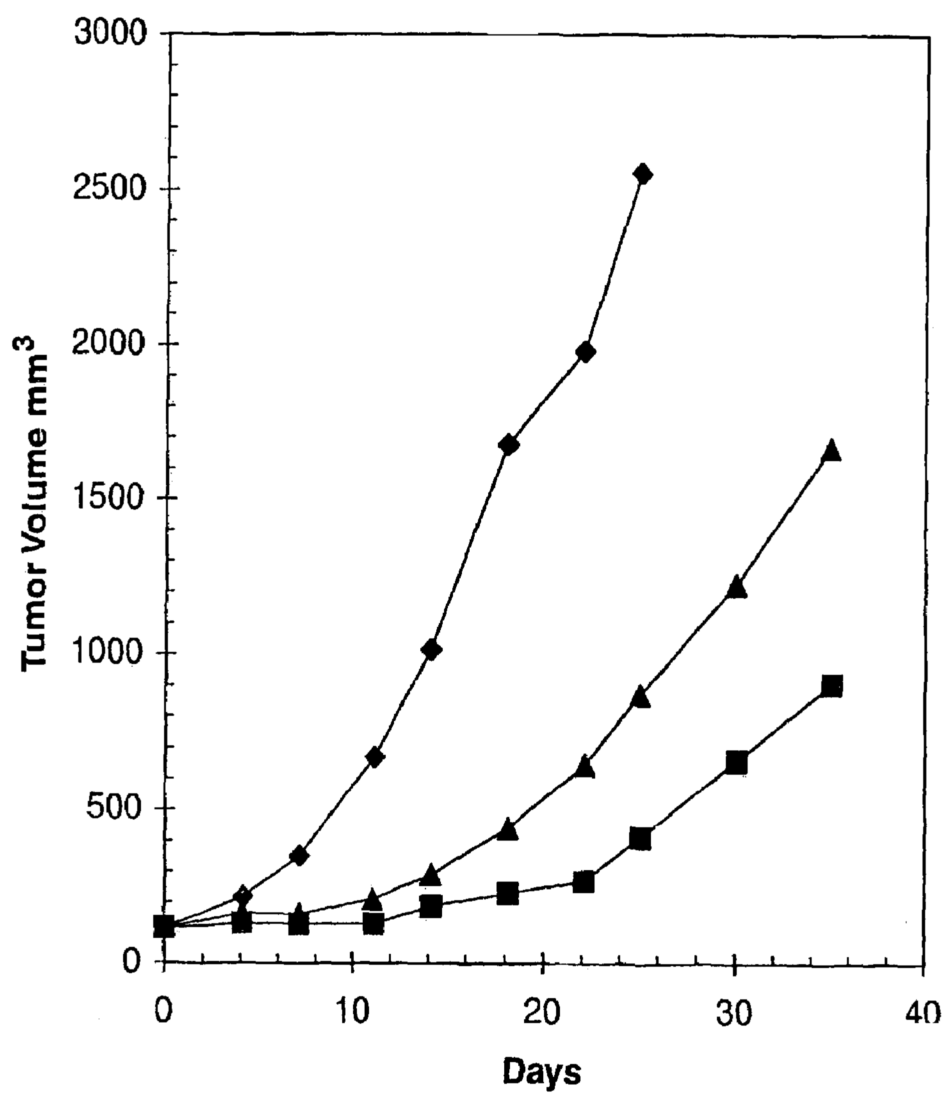
FIG. 12 shows the effect of antibody-cytokine-cytokine fusion protein treatment of SCID mice bearing subcutaneous tumors derived from CT26 colon carcinoma cells that were engineered to express human EpCAM. Diamonds indicate average tumor volumes in mice that were injected with PBS as controls on days 0, 1, 2, 3, and 4. Triangles indicate average tumor volumes in mice treated with 6 micrograms of KS-IL-12-IL-2. Squares indicate average tumor volumes in mice treated with 3.4 micrograms of KS-IL2 and 5.3 micrograms of KS-IL12. Intratumoral injections were performed. The x-axis indicates the number of days elapsed following the first injection; the y-axis indicates the average tumor volume in cubic milliliters.

Mice with subcutaneous CT26/KSA tumors were generated as described in Example 8. Three groups of 8 mice each, bearing tumors of about 100 to 200 cubic millimeters, were treated by intratumoral injection with the same dosing and schedule as in Example 8. Results are shown in FIG. 12. In this case, the KS-IL12-IL2 fusion protein and the mixture of KS-IL12 and KS-IL2 were about equally effective: five of eight mice were cured in each group by day 25. However, in the mice that were not cured, five of six tumors began to grow at a rate characteristic of tumors in untreated animals, with an effective delay of about 14 to 21 days. This is in contrast to tumors in immune-proficient mice in Example 8: even when tumors were not completely eliminated by treatment with KS-IL12-IL2, the tumors did not begin to grow aggressively until about 60 days after the beginning of the experiment.

These experiments demonstrate that a multiple-cytokine antibody fusion protein can be used to treat cancer in an immunosuppressed animal.

Example 10

Treatment of Lung Carcinoma by Intratumoral Injection of a Multiple Cytokine Fusion Protein: Comparison with Treatment by Individual Immunocytokines To address the effectiveness of multiple cytokine fusion proteins and immunocytokines carrying single cytokine moieties against a lung cell-derived cancer, the following experiment was performed.

Lewis Lung Carcinoma (LLC) is an aggressive tumor derived from C57BL/6 mice. An LLC cell line expressing the human EpCAM protein was constructed by standard genetic engineering techniques; the cell line was termed LLC/KSA.

C57BL/6 mice with subcutaneous LLC/KSA tumors were generated as described in Example 8 (check # of cells with KML). Four groups of 5 mice each, bearing tumors of about 100 to 200 cubic millimeters, were treated by intratumoral injection for five days. Mice were injected with PBS, about 20 micrograms of KS-IL12, about 20 micrograms of KS-IL12, or about 20 micrograms of KS-IL12-IL2.

Figure 13:
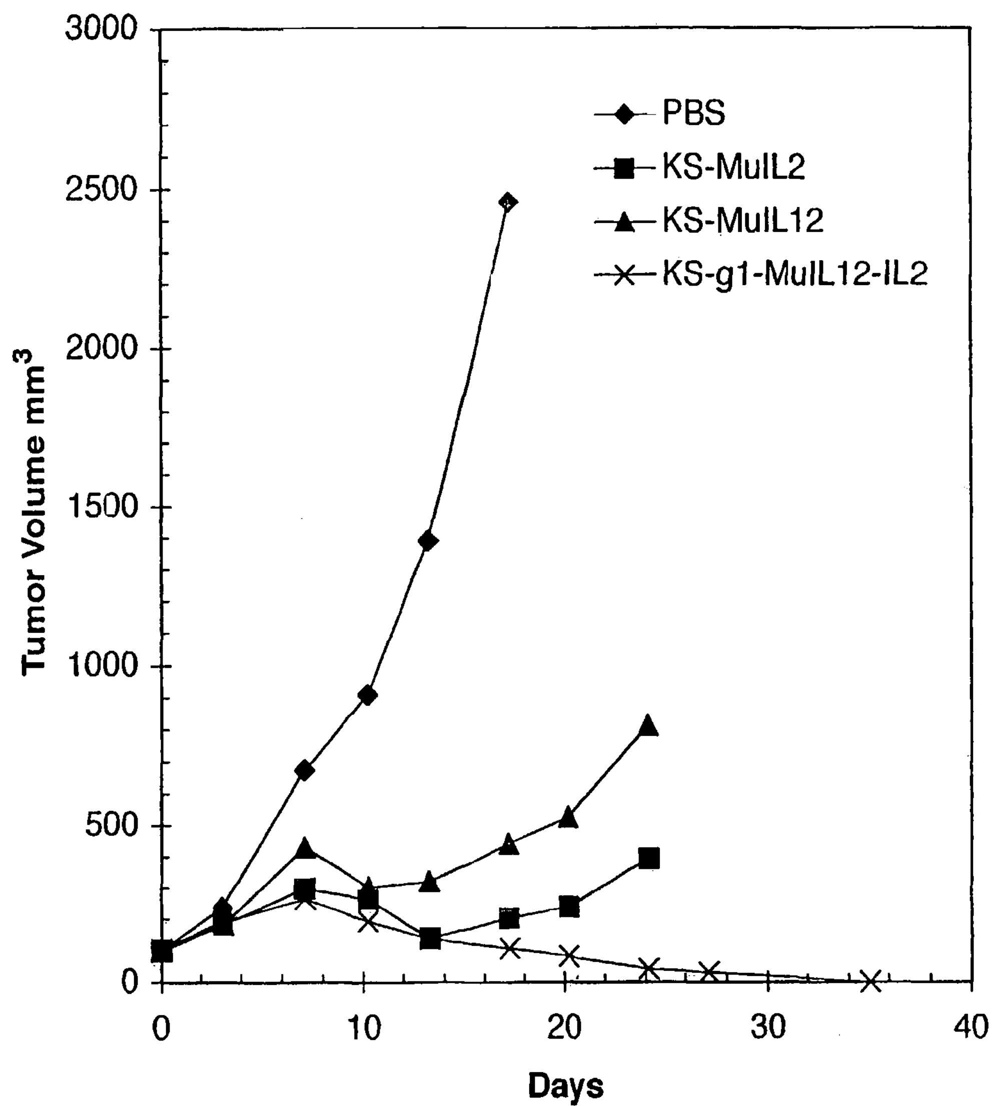
FIG. 13 compares the effect of antibody-cytokine and antibody-cytokine-cytokine fusion protein treatment of mice bearing subcutaneous tumors of Lewis lung carcinoma (LLC) cells that were engineered to express human EpCAM. Diamonds indicate average tumor volumes in mice that were injected intratumorally with PBS as controls on days 0, 1, 2, 3, and 4. Squares indicate average tumor volumes in mice injected intratumorally with 20 micrograms of KS-IL2 on days 0, 1, 2, 3, and 4. Triangles indicate average tumor volumes in mice injected intratumorally with 20 micrograms of KS-IL12 on days 0, 1, 2, 3, and 4. X's indicate average tumor volumes in mice injected intratumorally with 20 micrograms of KS-IL-12-IL-2 on days 0, 1, 2, 3, and 4. The x-axis indicates the number of days elapsed following the first injection; the y-axis indicates the average tumor volume in cubic milliliters.

Results are shown in FIG. 13. In this case, the KS-IL12-IL2 fusion protein was much more effective than either KS-IL12 or KS-IL2. In all of the mice treated with the KS-IL12-IL2 fusion protein, the tumors disappeared by day 27. On day 74, these mice were used in a lung metastasis assay as described in Example 14; the original subcutaneous tumors did not reappear in the intervening period or during the second experiment. In contrast, treatment with either KS-IL2 or KS-IL12 resulted in some apparent tumor shrinkage and a significant delay in tumor growth, but the tumors did eventually grow. A comparison of the results in this example and previous examples indicates that, for certain diseases and modes of administration, treatment with a mixture of immunocytokines carrying different cytokine moieties is superior to treatment with a single type of immunocytokine.

Example 12

Treatment of Lung Carcinoma by Intratumoral Injection of a Multiple Cytokine Fusion Protein: Comparison with Treatment by a Mixture of Immunocytokines To address the effectiveness of multiple cytokine fusion proteins and mixtures of immunocytokines carrying different cytokine moieties against a lung cell-derived cancer, the following experiment was performed.

C57BL/6 mice with subcutaneous LLC/KSA tumors were generated as described in Example 11. Three groups of 7 mice each, bearing tumors of about 100 to 200 cubic millimeters, were treated by intratumoral injection for five days. Mice were injected with PBS, a mixture of about 18 micrograms of KS-IL12 and about 11.5 micrograms of KS-IL12, or about 20 micrograms of KS-IL12-IL2.

Figure 14:
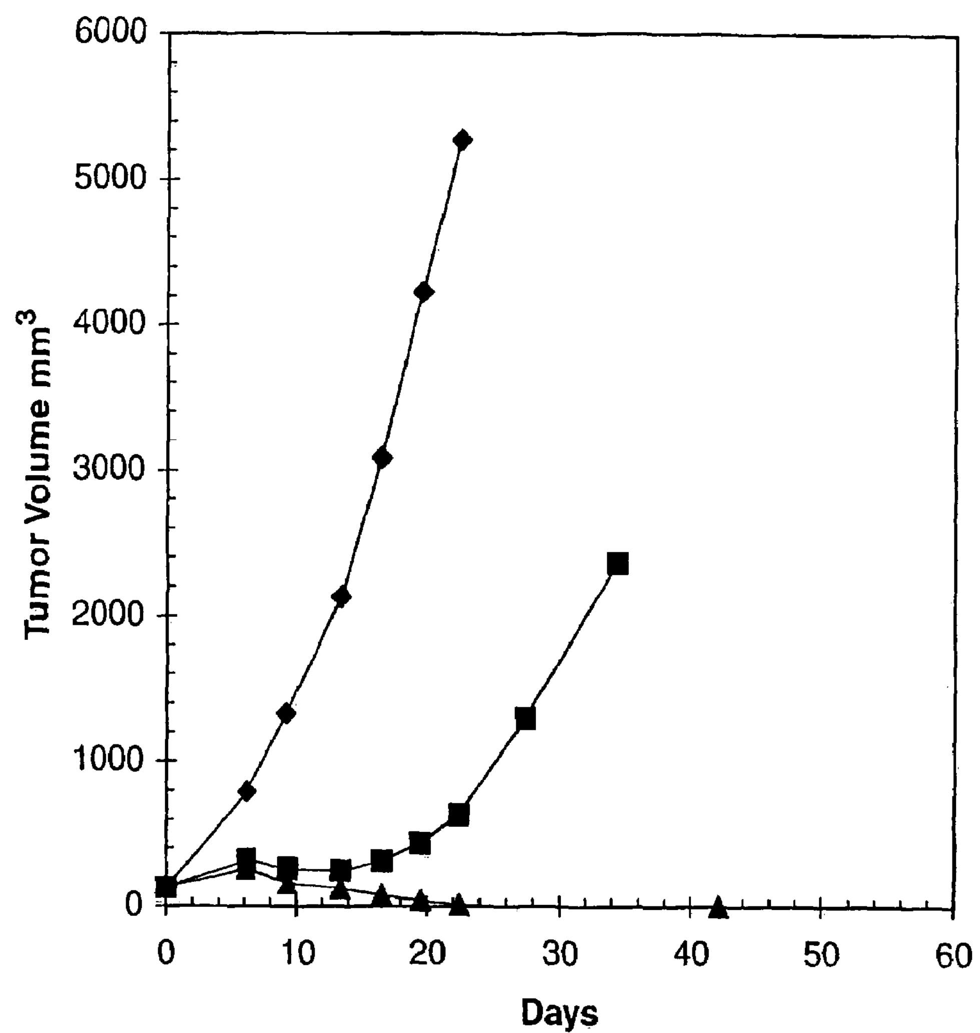
FIG. 14 shows the effect of antibody-cytokine-cytokine fusion protein treatment of mice bearing subcutaneous tumors derived from Lewis lung carcinoma cells that were engineered to express human EpCAM. Diamonds indicate average tumor volumes in mice that were injected with PBS as controls on days 0, 1, 2, 3, and 4. Triangles indicate average tumor volumes in mice treated with 20 micrograms of KS-IL-12-IL-2. Squares indicate average tumor volumes in mice treated with 11.5 micrograms of KS-IL2 and 18 micrograms of KS-IL12. Intratumoral injections were performed. The x-axis indicates the number of days elapsed following the first injection; the y-axis indicates the average tumor volume in cubic milliliters.

Results are shown in FIG. 14. In this case, the KS-IL12-IL2 fusion protein was much more effective than the mixture of KS-IL12 and KS-IL2. In all of the mice treated with the KS-IL12-IL2 fusion protein, the tumors disappeared by day 27. In contrast, treatment with the mixture of KS-IL12 and KS-IL2 resulted in some apparent tumor shrinkage and a significant delay in tumor growth, but all of the tumors in this treatment group did eventually regrow.

Example 13

Antigen-dependence of Anti-tumor Activity of a Multiple Cytokine-antibody Fusion Protein To address the whether the effectiveness of a multiple cytokine-antibody fusion protein in treatment of a tumor was dependent on the tumor-specific expression of the antigen recognized by the antibody, the following experiment was performed.

A set of seven C57BL/6 mice with subcutaneous LLC/KSA tumors and a second set of nine mice with tumors derived from the parental LLC cell line were generated as described in Example 11. These two groups of mice, bearing tumors of about 100 to 200 cubic millimeters, were treated by intratumoral injection for five days. Mice were injected with about 20 micrograms of KS-IL12-IL2.

Figure 15:
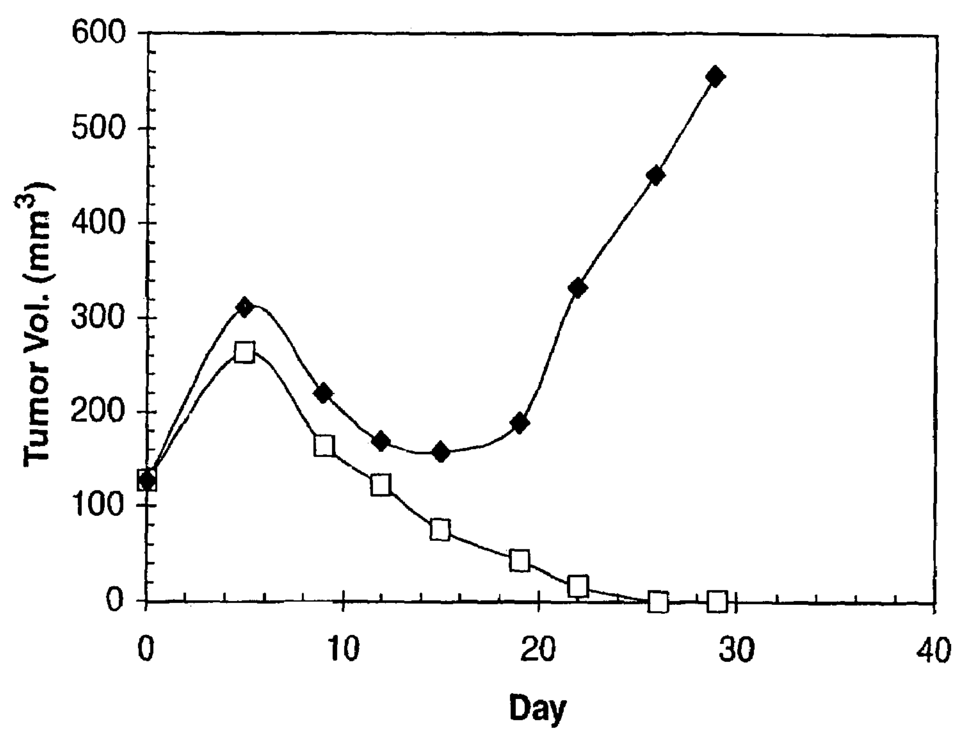
FIG. 15 shows the effect of antibody-cytokine-cytokine fusion protein treatment of mice bearing subcutaneous tumors derived from Lewis lung carcinoma cells that either do or do not express human EpCAM. Black squares indicate average tumor volumes in mice bearing LLC/KSA-derived tumors. Black diamonds indicate average tumor volumes in mice bearing LLC-derived tumors. Mice were treated with 20 micrograms of KS-IL12-IL2 on days 0, 1, 2, 3, and 4. Intratumoral injections were performed. The x-axis indicates the number of days elapsed following the first injection; the y-axis indicates the average tumor volume in cubic milliliters.

Results are shown in FIG. 15. In this case, the mice bearing the LLC/KSA tumors all were completely cured of their tumors. In contrast, only two of the mice bearing the LLC tumors were cured; the other LLC tumor-bearing mice all enjoyed a transient reduction in their tumor volumes, but their tumors eventually grew to large volumes.

These results indicate that the recognition of the EpCAM surface antigen promotes the adherence of KS-IL12-IL2 to the surface of LLC/KSA tumor cells, and the resulting immune response is enhanced. Some anti-tumor effect was observed against LLC-derived tumors as well; without wishing to be bound by theory, the antitumor effect of KS-IL12-IL2 in this case may be due to the fact that the fusion protein was injected directly into the tumor and was therefore transiently localized to the tumor.

Example 14

Generation of an Immune Memory Against a Tumor Cell Type

The development of metastases is a major problem in treatment of cancer. To test whether treatment with a multiple cytokine antibody fusion protein could lead to formation of a long-lasting immune memory against a tumor cell type and could prevent the establishment of metastases, the following experiment was performed.

Five C57BL/6 mice from Example 11 had been treated with KS-IL12-IL2, and had apparently been cured of their subcutaneous tumors. On day 74 relative to the initiation of treatment as described in Example 14, these five mice were injected i. v. with $10^6$ LLC/KSA cells. As a control, eight C57BL/6 mice were also injected i. v. with $10^6$ LLC/KSA cells.

On day 28, the mice were sacrificed and the lungs were examined for metastases. The lungs of the eight control mice were 70% to 100% covered with metastases, with an average of 85% lung surface coverage. The mean lung weight for these mice was 0.86 grams. In contrast, there were no metastases found on the surface of lungs from the five pre-treated mice, and the average lung weight was 0.28 grams, which corresponds to the weight of a normal mouse lung. These results indicated that the treatment of the original tumor cells resulted in a long-lasting immune memory against the tumor cells; this memory prevented the establishment of metastases of this tumor cell type.

TABLE X

Protection of "regressed" mice from LLC-KSA pulmonary metastases

| Prior Treatment | Metastatic Score | Lung Weight (g) |
|---|---|---|
| None | 4, 4, 4, 4, 4, 4, 3, 3 | 0.88 +/− 0.27 |
| KS-IL12/IL2 | 0, 0, 0, 0, 0 | 0.27 +/− 0.03 |

The average lung weight of the control group, without tumor, was 0.2 g. Metastatic scores are based on % surface coverage of fused metastatic nodules where 0=no metastases; 1=1-25% coverage; 2=25-50% coverage; 3=50-75% coverage; and 4=75-100% coverage A second experiment to test for immune memory formation used six of the seven mice from Example 12 that had been injected with LLC/KSA tumor cells, had developed subcutaneous tumors, and had had those tumors disappear. Sixty-two days after the initiation of the treatment in Example 12, six pre-treated mice and 10 naïve, untreated C57BL/6 control mice were injected s. c. with $10^6$ LLC cells. These cells do not express the human KS antigen, EpCAM.

Figure 16:
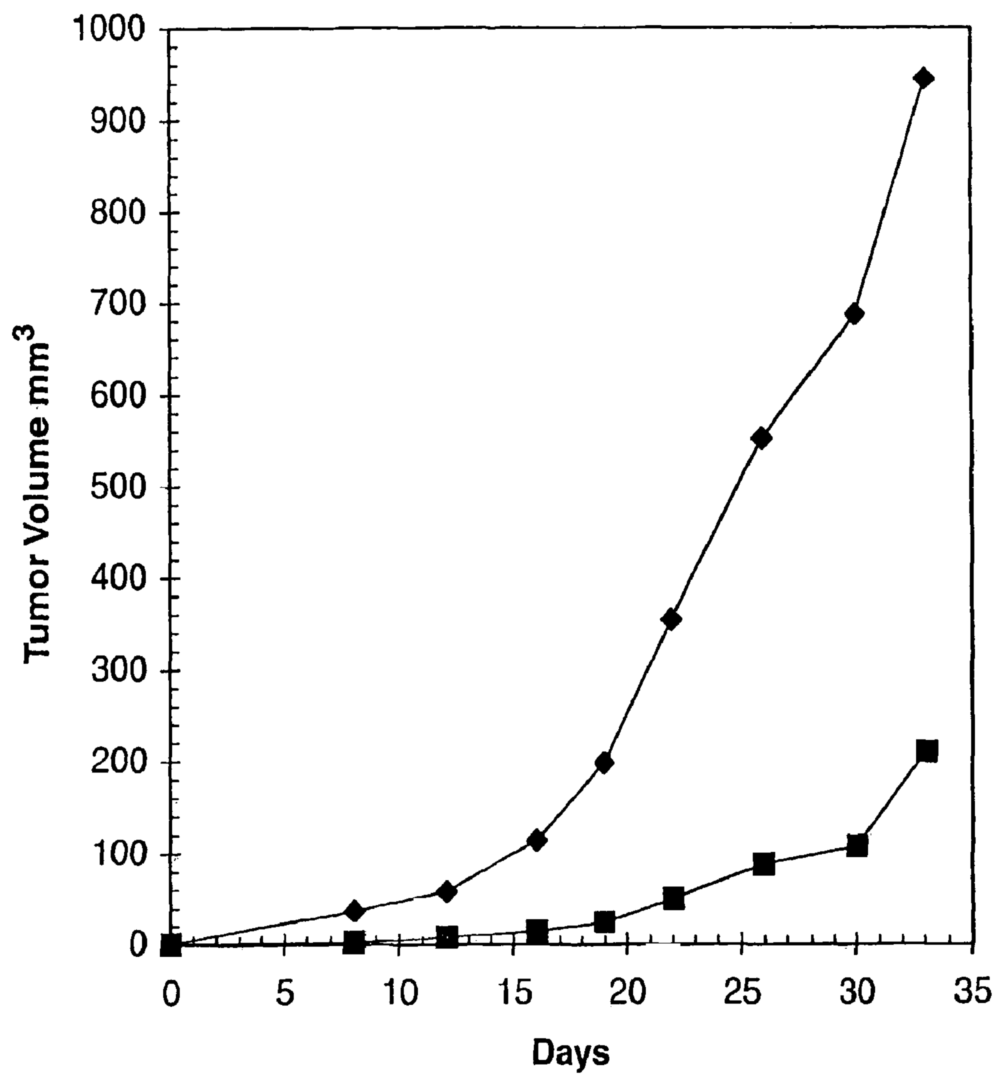
FIG. 16 shows the effect of antibody-cytokine-cytokine fusion protein treatment of mice bearing subcutaneous tumors derived from Lewis lung carcinoma cells. About $10^6$ cells were injected subcutaneously on Day 0. Diamonds indicate average tumor volumes in naïve mice. Squares indicate average tumor volumes in mice that had previously had subcutaneous tumors derived from Lewis lung carcinoma cells that were engineered to express human EpCAM, and had been cured of these tumors by treatment with KS-IL12-IL2. The x-axis indicates the number of days elapsed following the injection; the y-axis indicates the average tumor volume in cubic milliliters.

In the naïve mice, the injected LLC cells formed tumors that grew at a rapid rate in all mice. In contrast, the tumors in the pre-treated mice grew much more slowly, and in one mouse, no subcutaneous tumor was detected. The results are shown in FIG. 16. Because the human KS antigen, EpCAM, is not expressed on LLC cells, the immune response to the LLC cells was based on other antigens expressed by these cells.

Example 15

Multiple Cytokine Fusion Proteins as Vaccines

Multiple cytokine fusion proteins may be used as vaccines when fused to an antigen protein. The particular order of moieties from N-terminus to C-terminus, or whether the fusion protein is a single polypeptide chain or an oligomer, may vary depending on convenience of construction of the expressing plasmids. The protein may be administered by a variety of routes, such as intravenous, subcutaneous, intraperitoneal, and so on. Similarly, the dose and frequency of administration generally need to be empirically determined, as is standard practice for human vaccines and as is well known to those skilled in the art of vaccine development.

For example, a fusion protein of the form antigen-IL-12-cytokine is administered to a mouse, where the cytokine in the fusion protein is a second cytokine different from IL-12. Control mice receive the same amount of antigen-cytokine, antigen-IL-12, or antigen alone. At various times during and/or after administration of the antigen fusion protein, blood samples are collected by retro-orbital bleeding and plasma is prepared and analyzed for the presence of antibodies directed against the antigen. It is found that antibodies are generated against the antigen. Moreover, the nature of the immune response to the antigen is characteristic of a Th1 response. The antibody response is stronger and the type of antibodies produced are different than in certain control immunizations.

More specifically, a humanized antibody-murine IL-12-IL-2 fusion protein in PBS buffer, is injected into Balb/c mice intravenously (5 μg/day×5). Control mice receive the same antibody, in the same amounts, but with no attached IL-12-IL-2. Neither injection solution contains any other type of adjuvant. On day 10, blood samples are collected into microcentrifuge tubes by retro-orbital bleeding and plasma is prepared by collecting blood samples in plastic tubes containing sodium citrate, followed by centrifugation at full speed in an Eppendorf tabletop microcentrifuge. ELISA plates (96-well) are coated with the humanized antibody protein, which contains the human constant region and is used to capture any mouse antibodies made in response to the immunization. After washing away unbound material, the bound mouse antibodies are detected with goat anti-mouse Fc antibody (Jackson ImmunoResearch) coupled to horse-radish peroxidase. Any bound antibodies could be directed to either the human constant regions or the variable region, both of which are shared between the humanized antibody and the fusion proteins.

There is little or no reactivity to the humanized antibody without fused IL-12-IL-2. The fusion protein, on the other hand, induces a strong antibody response in the absence of exogenous adjuvants and despite the fact that the intravenous route of administration is highly unfavorable for inducing such responses, compared to either subcutaneous or intraperitoneal administration. Antibodies of the IgG2a isotype, which are typical of IL-12-enhanced responses, are seen in the antibody-IL-12-IL-2 injected group but not the group injected with the humanized antibody.

The immunogenicity of antigen-IL-12 multiple cytokine fusion proteins administered by various routes is tested by injecting a solution of the fusion protein (such as that described above) in PBS or other biocompatible buffer, or a known adjuvant such as Freund's incomplete or complete adjuvant. For example, single or multiple subcutaneous, intradermal or intraperitoneal injections can be given every two weeks. Alternatively, the fusion protein can be administered first by subcutaneous injection and then followed by intraperitoneal injection. Freund's adjuvant cannot be used for human use, due to the irritation at the injection site. Alternative adjuvants such as precipitates of aluminum hydroxide (Alum) are approved for human use and can be used in the present invention. New organic chemical adjuvants based on squalenes and lipids can also be used for injections into the skin.

Example 16

Gene Therapy with Multiple Cytokine Fusion Proteins

The anti-cancer activity of multiple cytokine fusion proteins delivered by gene therapy methods was also demonstrated for treatment of lung cancer. Lewis Lung Carcinoma cells were stably transfected using the viral vector system described above (pLNCX-scIL-12-IL-2 or pLNCX-scIL-12 DNA transfected into the PA317 packaging cell line). These constructs encode a single-chain version of IL-12, in which the p35 and p40 subunits have been connected with a linker. Clones were selected in vitro using G418-containing medium, and clones stably expressing about 50 to 60 ng/ml of IL-12 were identified by ELISA (R & D Systems).

Figure 17A:
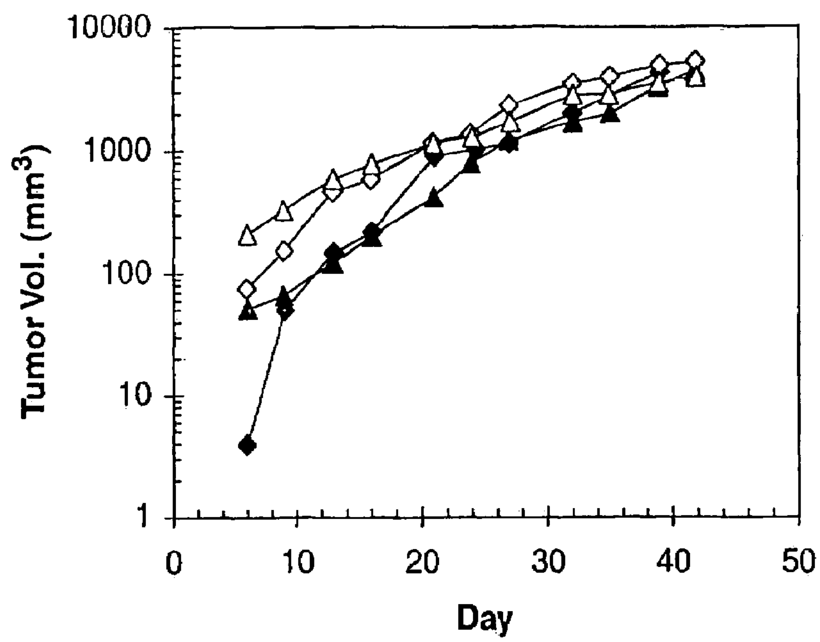
FIGS. 17A and 17B show the effect of single- or multiple-cytokine protein secretion by tumor cells on the ability of the cells to form tumors in an animal with a normal immune system.
Figure 17B:
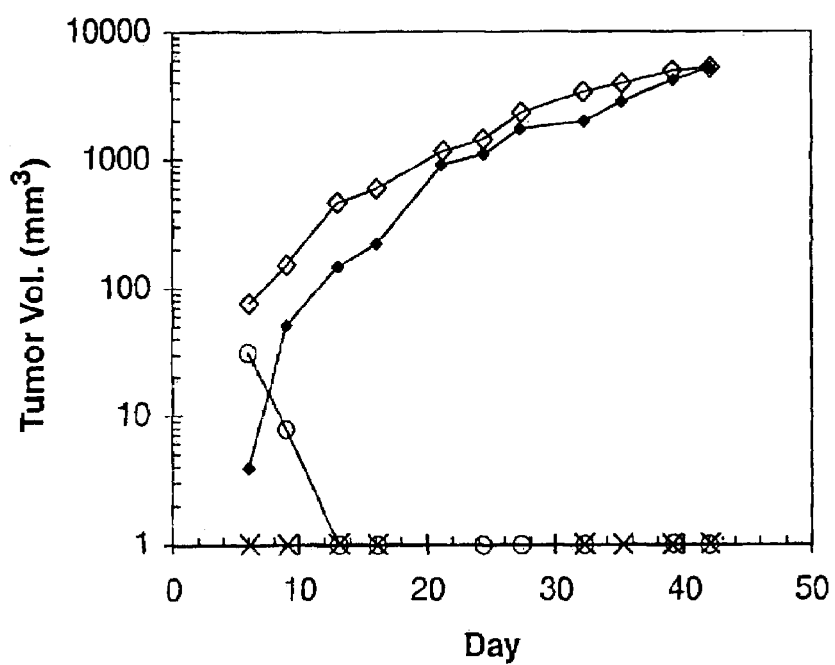
Figure 18:
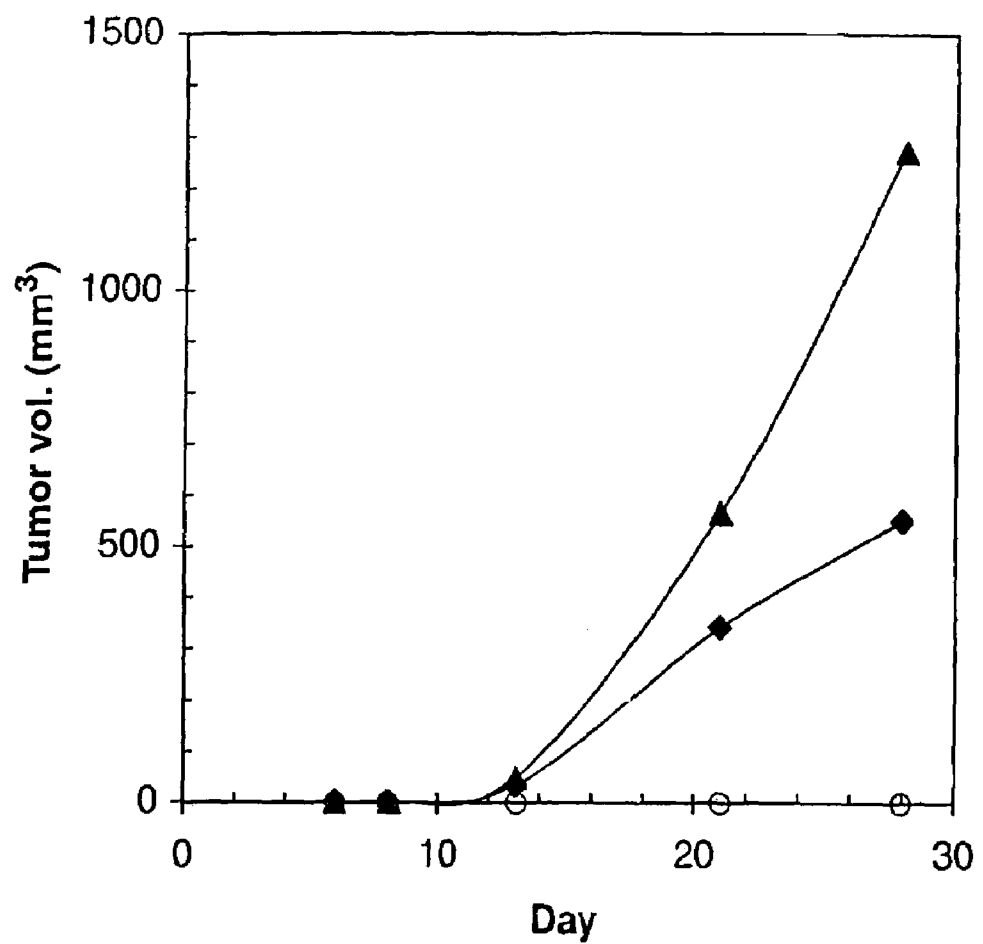
FIG. 18 shows the effect of single- or multiple-cytokine protein secretion by tumor cells on the ability of the cells to form tumors in an immune-deficient animal. This Figure compares SCID mice injected s. c. with $1\times10^6$ LLC tumor cells (black diamonds); SCID mice injected s. c. with $1\times10^6$ LLC tumor cells expressing scIL-12 (black triangles); and SCID mice injected s. c. with $1\times10^6$ LLC tumor cells expressing scIL-12 (white circles). The x-axis indicates the number of days after injection of the tumor cells. The y-axis indicates the tumor volume in cubic millimeters.

About $1\times10^6$ and about $5\times10^6$ LLC cells expressing scIL-12 or scIL-12-IL-2 were injected s.c. into C57BL/6 mice and also into SCID mice. As a control, $2\times10^6$ LLC cells were injected into C57BL/6 mice and also into SCID mice. The LLC cells expressing IL-12 form tumors that grow at about the same rate as tumors derived from LLC cells that have not been engineered to express cytokines. However, in both C57BL/6 mice and also in SCID mice, LLC cells expressing scIL-12-IL-2 either did not form subcutaneous tumors or formed tumors that subsequently shrank and disappeared (FIGS. 17 and 18).

Example 17

Construction of Multiple Cytokine Fusion Proteins Containing IL-4 and GM-CSF

The cytokines IL-4 and GM-CSF, when used in combination, are potent activators of dendritic cells. A multiple cytokine-antibody fusion protein containing IL-4 and GM-CSF activity was constructed as follows. The coding sequence for GM-CSF was fused in-frame to the 3' end of the KS-1/4 antibody heavy chain coding sequence, which was preceded by a leader sequence. In addition, the coding sequence for IL-4, including a leader sequence, was fused in-frame with a linker to the 5' end of the coding sequence for the mature KS-1/4 antibody light chain.

Specifically, to construct DNA encoding a fusion protein of murine IL-4 and the light chain of the KS-1/4 antibody, the murine IL-4 cDNA was adapted by PCR using the forward primer TCTAGACC ATG GGT CTC AAC CCC CAG C (SEQ ID NO:22), in which an XbaI site TCTAGA (residues 1-6 of SEQ ID NO:22) had been placed upstream of the translation initiation codon ATG, and the reverse primer C GGA TCC CGA GTA ATC CAT TTG CAT GAT GCT CTT TAG GCT TTC CAG G (SEQ ID NO:23), which contains a BamHI site GGA TCC (residues 2-7 of SEQ ID NO:23) immediately 3' to the TCG codon (anticodon CGA) encoding the C-terminal amino acid residue of murine IL-4. After cloning of the PCR fragment and sequence verification, the XbaI-BamHI fragment containing the murine IL-4 cDNA was ligated to an BamHI-AflII oligonucleotide duplex encoding a flexible peptide linker rich in glycine and serine residues. The AflII end was in turn joined to an artificially placed AflII site preceding the N-terminus of the mature KS-1/4 light chain. The DNA and protein sequences at the junctions resulting from the two ligations are given below.

```
DNA:     TCG GGA TCC GGA GGT TCA GGG GGC GGA GGT AGC GGC GGA GGG GGC TCC TTA AGC GAG    (SEQ ID NO:24)
Protein: (Ser) Gly Ser Gly Gly Ser Gly Gly Gly Gly Ser Gly Gly Gly Gly Ser Leu Ser (Glu)   (SEQ ID NO:25)
```

In this DNA sequence, GGATCC (residues 4-9 of SEQ ID NO:24) and CTTAAG (residues 48-53 of SEQ ID NO:24) are the two restriction sites BamHI and AflII, respectively, used for reconstruction; TCG encodes the C-terminal serine residue of murine IL-4; GAG encodes the mature N-terminus of the KS-1/4 light chain; and the amino acid sequence of the GlySer-rich peptide linker is shown below the DNA sequence. Auxiliary sequences for high-level expression including strong promoters were placed appropriately around the DNA segments encoding both fusion polypeptides, using techniques described in previous examples and other standard techniques of molecular biology.

The DNA sequences encoding the IL4-KS(light chain) and KS(heavy chain)-GM-CSF fusion proteins were transfected into NS/0 cells and the corresponding polypeptides were expressed at high levels. SDS-PAGE under reducing conditions showed a diffuse band at about 80 kD corresponding to the heavy chain-GM-CSF polypeptide and multiple bands at about 50 kD corresponding to the IL4-light chain fusion. The appearance of diffuse and multiple bands were due to the variable glycosylation of IL-4 and GM-CSF, respectively.

Figure 3G:
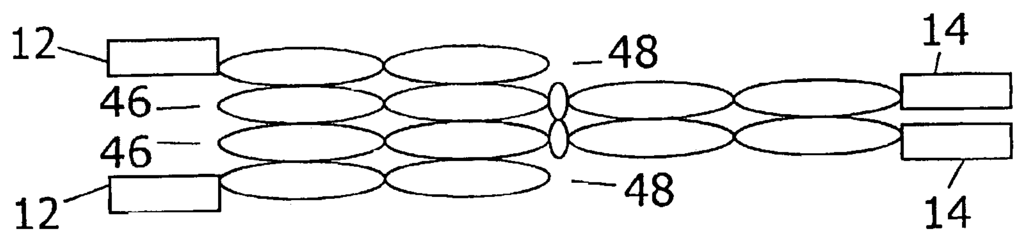

The subunits assembled into a disulfide-bonded tetrameric protein with a structure corresponding to the generic structure in FIG. 3G. This protein had the antigen-binding activity of KS-1/4, the ability to bind to Staph A protein via its Fc regions, and the cytokine activities of IL-4 and GM-CSF. IL-4 activity was measured by IL-4-dependent stimulation of tritiated thymidine incorporation in CTLL-2 cells. GM-CSF activity was measured by the GM-CSF-dependent stimulation of tritiated thymidine incorporation in 32(D) GM cells. On a molar basis, the IL-4 activity and the GM-CSF activity of KS-IL4-GMCSF were similar to purified IL-4 and GM-CSF.

A fusion of the cytokines IL-4 and GM-CSF, without associated antibody sequences, was constructed as follows. Murine IL-4 was cloned by PCR from RNA of murine spleen cells. The forward primer had the sequence TCTAGACC ATG GGT CTC AAC CCC CAG C (SEQ ID NO:26), in which an XbaI site TCTAGA (residues 1-6 of SEQ ID NO:26) was placed upstream of the translation initiation codon ATG, and the reverse primer had the sequence CGA TAT CCC GGA CGA GTA ATC CAT TTG CAT GAT GCT CTT TAG GCT TTC CAG G (SEQ ID NO:27), which placed an EcoRV site GAT ATC (residues 2-7 of SEQ ID NO:27) immediately 3' of the TCG codon (anticodon CGA) encoding the C-terminal amino acid residue of murine IL-4. After sequence verification, the XbaI-EcoRV fragment containing the muIL-4 cDNA with its native leader was ligated to the SmaI-XhoI fragment containing muGM-CSF cDNA to give the following sequence at the junction of the fusion between muIL-4 and muGM-CSF: ATG GAT TAC TCG TCC GGG ATG GGA AAA GCA CCC GCC CGC (SEQ ID NO:28), where the C-terminal sequence of muIL4 and the N-terminal sequence of muGM-CSF are in bold, and the G ATG GG (residues 17-22 of SEQ ID NO:28) is the sequence resulting from the ligation of an EcoRV blunt end to a SmaI blunt end. The resultant DNA encoding muIL4-muGMCSF was then cloned into an expression vector. The expressed protein was analyzed by SDS-PAGE and found to run as a diffuse band with an apparent molecular weight of 45 to 50 kD. On a molar basis, the IL-4 activity and the GM-CSF activity of IL4-GMCSF were similar to purified IL-4 and GM-CSF.

Example 18

Construction of DNA Encoding Lymphotactin-KS-IL2 and Expression of the Lymphotactin-KS-IL2 Protein Chemokines are a distinct class of cytokines that are thought to form gradients and mediate chemotaxis of immune cells. In addition, like other cytokines, chemokines may induce expression of specific genes in target cells. One characteristic of chemokines is that the free N-terminus is often required for activity, which could place limits on the ways that fusion proteins could be constructed.

A cytokine-antibody-cytokine fusion protein was constructed consisting of the cytokine lymphotactin, which is a chemokine, the antibody KS-1/4, and the cytokine IL-2. This fusion protein was tetrameric and comprised two different polypeptides. One polypeptide consisted of murine lymphotactin fused to the N-terminus of the heavy chain of the KS-1/4 antibody, followed by IL-2 at the C-terminus. The fusion of the KS-1/4 heavy chain with IL-2 at the C-terminus, the "KS-IL2 heavy chain," has been described previously [Gillies et al. (1992) Proc. Natl. Acad. Sci. USA 89:1428]. The other polypeptide consisted of the light chain of the KS 1/4 antibody.

The complete coding sequence of murine lymphotactin was published by Kelner and Zlotnik (Science 266:1395 [1998]). To construct DNA encoding a fusion protein of murine lymphotactin and the heavy chain of the KS-IL2, the murine lymphotactin cDNA was adapted by PCR using the forward primer TCTAGAGCCACC ATG AGA CTT CTC CTC CTG AC (SEQ ID NO:29), in which an XbaI site TCTAGA (residues 1-6 of SEQ ID NO:29) was placed upstream of the translation initiation codon ATG, and the reverse primer GGA TCC CCC AGT CAG GGT TAC TGC TG (SEQ ID NO:30), which placed a BamHI site GGA TCC (residues 1-6 of SEQ ID NO:30) immediately 3' of the GGG codon (anticodon CCC) encoding the C-terminal amino acid residue of murine lymphotactin. After cloning of the PCR fragment and sequence verification, the XbaI-BamHI fragment containing the murine lymphotactin cDNA was ligated to an BamHI-AflII oligonucleotide duplex encoding a flexible peptide linker rich in glycine and serine residues. The AflII end was in turn joined to an artificial AflII site preceding the mature N-terminus of the KS-IL2 heavy chain. The DNA sequence at the junctions resulting from the two ligations is given below:

Gly Ser Gly Gly Ser Gly Gly Gly Gly Ser Gly Gly Gly Gly Ser Leu Ser (SEQ ID NO:32)

CCC *GGA TCC* GGA GGT TCA GGG GGC GGA GGT AGC GGC GGA GGG GGC TCC *TTA AGC* CAG (SEQ ID NO:31)

where GGATCC (residues 4-9 of SEQ ID NO:31) and CTTAAG (residues 48-53 of SEQ ID NO: 31) are the two restriction sites BamHI and AflII, respectively, used for reconstruction; CCC encodes the C-terminal amino acid residue of murine lymphotactin; CAG encodes the mature N-terminus of the KS-IL2 heavy chain; and the amino acid sequence of the GlySer-rich peptide linker is shown above the DNA sequence. The DNA encoding the murine lymphotactin-KS-IL2 heavy chain was then cloned into an expression vector and then coexpressed with the KS1/4 light chain.

The expressed lymphotactin-KS-IL2 fusion protein is tested for lymphotactin activity in a Boyden chamber migration assay using T cells (Leonard et al., [1999] Current Protocols in Immunology p. 6.12.3). Alternatively, NK cells are used. Alternatively, lymphotactin activity is observed in a standard cellular assay for calcium flux in response to the activation of a G-protein coupled receptor (Maghazachi et al., FASEB J. [1997]; 11:765-74). In addition, the lymphotactin-KS-IL2 fusion protein is tested and found to be active in assays for the ability to bind to EpCAM and is also active in assays for IL-2 activity, such as the CTLL-2 cell proliferation assay.

Incorporation By Reference

All publications mentioned hereinabove are incorporated by reference into this application in their entirety.

Equivalents

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A method of targeting a first cytokine (C1) and a second, different cytokine (C2) in a mammal, the method comprising:

administering to the mammal a multifunctional fusion protein comprising a C1, a C2, and an immunoglobulin region (Ig) capable of targeting said fusion protein in the mammal, wherein C1 comprises IL-12 and C2 comprises a chemokine or a four-helix bundle cytokine.

2. The method of claim 1, wherein said Ig comprises an immunoglobulin heavy chain variable region domain immunologically reactive with an antigen in the mammal.

3. The method of claim 2, wherein said antigen is a cancer-specific antigen or a viral antigen.

4. The method of claim 1, wherein said Ig comprises an immunoglobulin heavy chain constant region capable of binding an immunoglobulin Fc receptor.

5. The method of claim 1, wherein said mammal is a human.

6. The method of claim 1, wherein said C2 is selected from the group consisting of IL-2 and GM-CSF.

* * * * *